(12) United States Patent
Bovin et al.

(10) Patent No.: US 10,781,235 B2
(45) Date of Patent: Sep. 22, 2020

(54) MULTIVALENT LIGAND-LIPID CONSTRUCTS

(71) Applicants: Nicolai Vladimirovich Bovin, Moscow (RU); Stephen Micheal Henry, Auckland (NZ); Elena Korchagina, Moscow (RU); Alexander Borisovich Tuzikov, Moscow (RU); Ludmila Baidakova Pushchino, Rodionov, Moscow Region (RU)

(72) Inventors: Nicolai Vladimirovich Bovin, Moscow (RU); Stephen Micheal Henry, Auckland (NZ); Elena Korchagina, Moscow (RU); Igor Leonidovich Rodionov, Moscow Region (RU); Alexander Borisovich Tuzikov, Moscow (RU)

( * ) Notice: Subject to any disclaimer, the term of this patent is extended or adjusted under 35 U.S.C. 154(b) by 0 days.

(21) Appl. No.: 16/665,016

(22) Filed: Oct. 28, 2019

(65) Prior Publication Data
US 2020/0048309 A1 Feb. 13, 2020

Related U.S. Application Data

(63) Continuation of application No. 15/528,732, filed as application No. PCT/NZ2015/050197 on Nov. 23, 2015, now Pat. No. 10,457,706.

(30) Foreign Application Priority Data

Nov. 21, 2014 (AU) .................... 2014904722
Nov. 11, 2015 (AU) .................... 2015904654

(51) Int. Cl.
| | | |
|---|---|---|
| *C07K 9/00* | (2006.01) | |
| *A61K 31/685* | (2006.01) | |
| *A61K 31/7004* | (2006.01) | |
| *A61K 31/702* | (2006.01) | |
| *A61K 31/7016* | (2006.01) | |
| *C07K 7/06* | (2006.01) | |
| *A61K 47/54* | (2017.01) | |
| *C07K 14/00* | (2006.01) | |
| *C07K 7/08* | (2006.01) | |
| *A61K 38/00* | (2006.01) | |

(52) U.S. Cl.
CPC .............. *C07K 9/00* (2013.01); *A61K 31/685* (2013.01); *A61K 31/702* (2013.01); *A61K 31/7004* (2013.01); *A61K 31/7016* (2013.01); *A61K 47/555* (2017.08); *C07K 7/06* (2013.01); *C07K 7/08* (2013.01); *C07K 14/001* (2013.01); *A61K 38/00* (2013.01)

(58) Field of Classification Search
CPC .......... C07K 9/00; C07K 14/001; C07K 7/08; C07K 7/06; A61K 47/555; A61K 31/7016; A61K 31/685; A61K 31/702; A61K 31/7004; A61K 38/00

See application file for complete search history.

(56) References Cited

U.S. PATENT DOCUMENTS

| 4,639,512 A | 1/1987 | Audibert et al. |
| 2010/0227402 A1 | 9/2010 | Carter et al. |
| 2011/0257081 A1* | 10/2011 | Bovin ............... A61K 47/641 514/3.7 |

FOREIGN PATENT DOCUMENTS

| WO | WO 2005/090368 | 9/2005 |
| WO | WO 2007/035116 | 3/2007 |
| WO | WO 2009/048343 | 4/2009 |
| WO | WO 2010/043230 | 4/2010 |
| WO | WO 2012/118388 | 9/2012 |
| WO | WO 2015/170121 | 11/2015 |

OTHER PUBLICATIONS

International Search Report issued in PCT/NZ2015/050197 dated Feb. 8, 2016.
International Preliminary Report on Patentability issued in PCT/NZ2015/050197 dated Mar. 9, 2017.
Barr et al (2014) *Mapping the fine specificity of ABO monoclonal reagents with A and B type-specific function-spacer-lipid constructs in kodecytes and inkjet printed on paper* Transfusion, 54, 2477-2484.
Bar et al (2015) *Monoclonal anti-A activity against the FORS1(Forssman) antigen* Transfusion, 55, 129-136.
Blake et al (2011) *FSL Constructs: A Simple Method for Modifying Cell/Virion Surfaces with a Range of Biological Markers Without Affecting their Viability* J. Vis. Exp., 54, e3289; DOI: 10.3791/3289.
Bovin et al (1993) *Synthesis of polymeric neoglycoconjugates based on N-substituted polyacrylamides* Glycoconjugate Journal 10, 142-151.
Frame et al (2007) *Synthetic glycolipid modification of red blood cell membranes* Transfusion, 47, 876-882.
Galanina et al (1997) *Further Refinement of the Description of the Ligand-binding Characteristics for the Galactoside-binding Mistletoe Lectin, a Plant Agglutin with Immunomodulatory Potency* Journal of Molecular Recognition, 10, 139-147.
Georgakopoulos et al (2012) *An improved Fc function assay utilizing CMV antigen-coated red blood cells generated with synthetic function-spacer-lipid constructs* Vox Sanguinis, 102, 72-78.
Grogan et al; "Synthesis of Lipidated Green Fluorescent Protein and Its Incorporation in Supported Lipid Bilayers "*J. Am. Chem. Soc.*, 2005, 127, 14383-14387.
Harrison et al (2010) *A synthetic globotriaosylceramide analogue inhibits HIV-1 infection in vitro by two mechanisms* Glycoconj. J., 27, 515-524.
Henry (2009) *Modification of red blood cells for laboratory quality control use* Curr. Opin. Hematol., 16, 467-472.

(Continued)

*Primary Examiner* — Sudhakar Katakam
(74) *Attorney, Agent, or Firm* — Nixon & Vanderhye P.C.

(57) ABSTRACT

Water dispersible, multivalent ligand-lipid constructs that spontaneously and stably incorporate into membranes are disclosed.

8 Claims, 2 Drawing Sheets
Specification includes a Sequence Listing.

(56) References Cited

OTHER PUBLICATIONS

Hult et al (2012) *Flow cytometry evaluation of red blood cells mimicking naturally occurring ABO subgroups after modification with variable amounts of function-spacer-lipid A and B constructs* Transfusion, 52, 247-251.

Karelin et al (2010) *Synthesis of 3, 6-branched oligomannoside fragments of the mannan from Candida albicans cell corressonding to the antigenic factor 4* Carbohdrate Research 345, 1283-1290.

Korchagina et al (2009) *Block synthesis of blood group tetrasaccharides B (types 1,3 and 4)* Mendeleev Commun., 19, 152-154.

Korchagina et al (2012) *Toward creating cell membrane glycollandscapes with glycan lipid constructs* Carbohydr. Res., 356, 238-246.

Korchagina et al (2015) *Synthetic Glycolipid-Like Constructs as Tools for Glycobiology Research, Diagnostics, and as Potential Therapeutics* Biochemistry (Moscow), vol. 80, No. 7, 857-871.

Lee et al (1997) *Facile Synthesis of a High-Affinity Ligand for Mammalian Hepatic Lectin Containing Three Terminal N-Acetylgalactosamine Residues* Bioconjugate Chem., 8, 762-765.

Litherland et al (1938) *The Amino-derivatives of Pentaerythritol Part I. Preparation* Journal of the Chemical Society, 1588-1595.

Ma et al., "Lipid Membrane Adhesion and Fusion Driven by Designed, Minimally Multivalent Hydrogen-Bonding Lipids" *J. Am. Chem. Soc.*, 2009, 131, 16919-16926.

Ma et al., "Directed Peptide Assembly at the Lipid-Water Interface Cooperatively Enhances Membrane Binding and Activity" *Langmuir*, 2011, 27(4), 1480-1486.

Ma et al., "Stabilization of vesicular and supported membranes by glycolipid oxime polymers" *Chem. Commun*., 2011, 47, 2853-2855.

McNaught (1996) *Nomenclature of carbohydrates* Pure & App. Chem., 68, No. 10, 1919-2008.

Nifant'ev et al (1996) *Selectin-receptors 4: synthesis of tetrasaccharides sialyl Lewis A and sialyl Lewis X containing a spacer group*[1,2] J. Carbohydrate Chemistry, 15(8), 939-953.

Oliver et al (2011) *Modeling transfusion reactions and predicting in vivo cell survival with kodecytes* Transfusion, 51, 1723-1730.

Oliver et al (2011) *In vivo neutralization of anti-A and successful transfusion of A antigen incompatible red cells in an animal model* Transfusion, 51, 2664-2675.

Paulsen et al (1978) *Darstellung selektiv blockierter 2-azido-2-desoxy-$_d$-gluco-und-$_d$-galactophyranosylhalogenide: Reaktivität und $^{13}$C-NMR-Spekfren*Carbohydrate Research, 64, 339-364.

Pazynina et al (2003) *Synthesis of complex 2-3 sialooligosaccharides, including sulfated and fucosylated ones, using Neu5Aca2-3Gal as a building block* Mendeleev Commun, 13(6), 245-248.

Pazynina et al (2008) *The synthesis of linear trilactosamine* Russian Journal of Bioorganic Chemistry, vol. 34, No. 5, 625-631.

Perry et al (2013) *Teaching the recognition of hemolysis by controlling antibody mediated in vitro hemolysis with kodecytes* Transfusion, 53 (Suppl.), 182A.

Perry et al. (2015) *Training students in serologic reaction grading increased perceptions of self-efficacy and ability to recognize serologic reactions but decreased grading accuracy* Transfusion, Jan. 7, DOI: 10.1111/trf.12985 [Epub ahead of print].

Rhyzhov et al (2012) *Block synthesis of A tetrasaccharides ( types 1, 3 and 4 ) related to the human ABO blood group system* Carbohydrate Research 351, 17-25.

Sherman et al (2001) *Synthesis of Neu5Ac- and Neu5Gc-a-(2→6')-lactosamine 3-aminopropyl glycosides* Carbohydrate research 330, 445-458.

Svensson et al (2013) *Forssman expression on human erythrocytes: biochemical and genetic evidence of a new histo-blood group system* Blood, 121, 1459-1468.

Vodovozova et al (2000) *Antitumour activity of cytotoxic liposomes equipped with s electin ligand SiaLe$_X$, in a mouse mammary adenocarcinoma model* European Journal of Cancer, 36, 942-949.

Yashunsky et al (2016) *Synthesis of 3-aminopropyl glycosides of linear β-(1→3)-D-glucooligosaccharides* Carbohydrate Research 419, 1-10.

\* cited by examiner

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial sequence
<220> FEATURE:
<223> OTHER INFORMATION: Synthetic peptide

<400> SEQUENCE: 1

Ser Gln Thr Asn Asp Lys His Lys Arg Asp Thr Tyr Pro Cys
1               5                   10
```

MULTIVALENT LIGAND-LIPID CONSTRUCTS

This application is a continuation of U.S. application Ser. No. 15/528,732 filed May 22, 2017 (now U.S. Pat. No. 10,457,706), which is the U.S. national phase of International Application No. PCT/NZ2015/050197 filed Nov. 23, 2015 which designated the U.S. and claims priority to Australian Patent Application Nos. 2014904722 filed Nov. 21, 2014, and 2015904654 filed Nov. 11, 2015, the entire contents of each of which are hereby incorporated by reference.

This application contains a Sequence Listing which has been filed electronically in ASCII format.

TECHNICAL FIELD

The invention relates to water dispersible, multivalent ligand-lipid constructs that spontaneously and stably incorporate into membranes and the use of such constructs in diagnostic, prognostic, prophylactic and therapeutic applications. In particular, the invention relates to the use of the multivalent ligand-lipid constructs in the preparation of kodecytes with increased avidity for ligand binding proteins.

BACKGROUND ART

The publication of Bovin et al (2005) discloses synthetic molecules that spontaneously and stably incorporate into lipid bilayers, including cell membranes. The synthetic molecules consist of a functional moiety (F), such as a mono-, di-, tri- or oligosaccharide, covalently linked to a lipid moiety (L), such as phosphatidylethanolamine, via a spacer (S). The spacer is selected to provide synthetic molecules that readily disperse in water without the use of detergents or solvents and may be used to effect qualitative and quantitative changes in the expression of cell surface antigens. The publication discloses the use of these synthetic molecules in a method of preparing red blood cells expressing controlled amounts of blood group-related glycans. These modified or transformed cells (now referred to as 'kodecytes') may be used as positive controls in the quality assurance of blood group typing reagents.

The publication of Bovin et al (2009) discloses functional lipid constructs consisting of a functional moiety (F) covalently linked to a lipid (L) moiety via an elongate spacer (S). In common with the synthetic molecules disclosed in the publication of Bovin et al (2005), the constructs spontaneously incorporate into cell membranes despite being readily dispersible in water. The constructs provide the additional advantage that the functional moiety (F) is presented at a distance from the surface of the cell membrane. The publication of Bovin et al (2010) discloses constructs where the functional moiety (F) is a ligand for a receptor. The publication discloses multiligand constructs of a tri- or tetra-antennary structure. The inter-ligand spacing of the constructs is intended to promote multivalent interactions between the ligands and the ligand-binding protein or receptor.

Ligand binding proteins include glycan binding proteins (GBPs). These proteins play important roles in mechanisms of immunity and microbe-host interactions. GBPs are present in the sera of all individuals. The immune system depends largely on the presence of a competent and well-equipped repertoire of these GBPs. Many of the GBPs are natural antibodies (NAbs) that bind to glycan ligands expressed in normal human tissues (auto-antibodies). However, NAbs may also be associated with a number of diseases, e.g. the antibodies to tumour-associated carbohydrate antigens (TACA). Transformation of cells from healthy to pre-malignant and malignant is associated with the appearance of abnormal glycosylation on proteins and lipids presented on the surface of the cells. Changes in the NAb profile of an individual can therefore be associated with the onset and progress of a number of diseases, including cancer.

It is an object of the present invention to provide multivalent ligand-lipid constructs for use in the preparation of kodecytes with increased avidity for ligand binding proteins. The preceding object is to be read in the alternative with the object at least to provide a useful choice.

DISCLOSURE OF INVENTION

In a first aspect the invention provides a multivalent ligand-lipid construct of the structure:

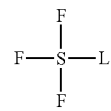

where F is a ligand, S is a tetraantennary spacer, and L is a conjugated phosphatidylethanolamide.

Preferably, S is a tetraantennary spacer of the structure:

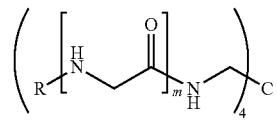

where m is the integer 1, 2 or 3 and R is of the structure:

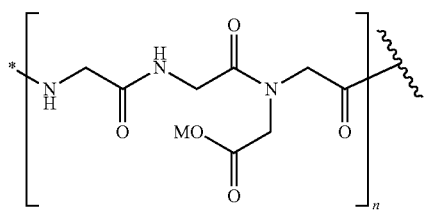

where M is a monovalent cation or substituent, n is the integer 2, 3, 4, 5, 6 or 7, and * is the point of attachment of F or L. Preferably, M is $H^+$ and n is the integer 5.

Preferably, L is a conjugated phosphatidylethanolamide of the structure:

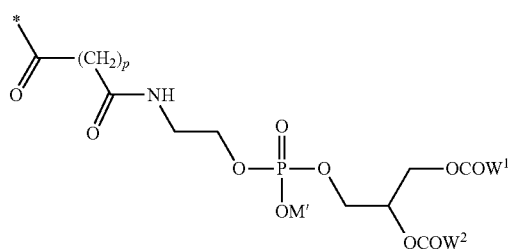

where M' is a monovalent cation, p is the integer 3, 4 or 5, $W^1$ and $W^2$ are independently selected from $C_{16-20}$-alkyl or mono- or di-unsaturated $C_{16-20}$-alkenyl groups and * is the point of attachment of S.

Preferably, the multivalent ligand-lipid construct comprises the partial structure:
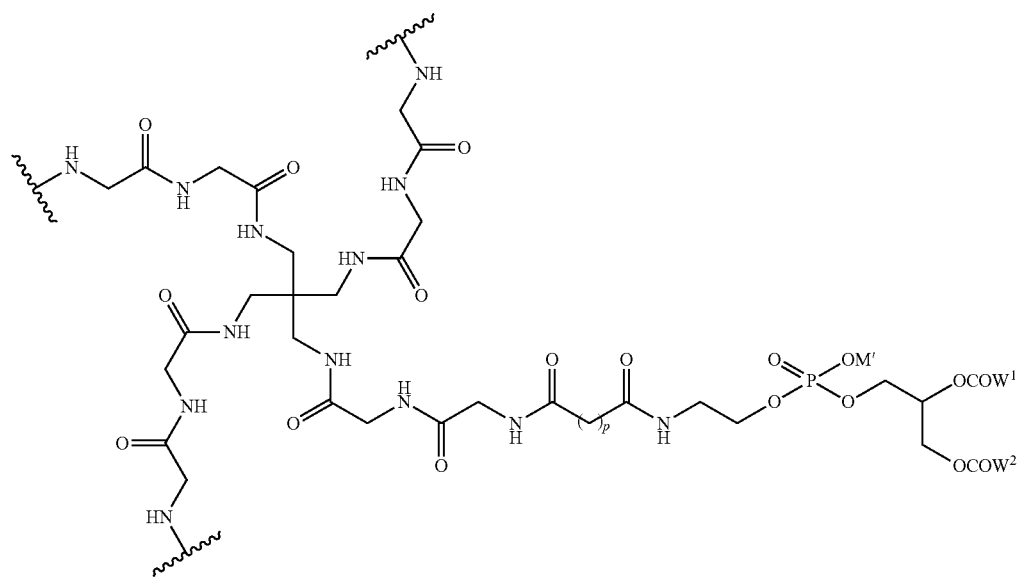
More preferably, the multivalent ligand-lipid construct comprises the partial structure:
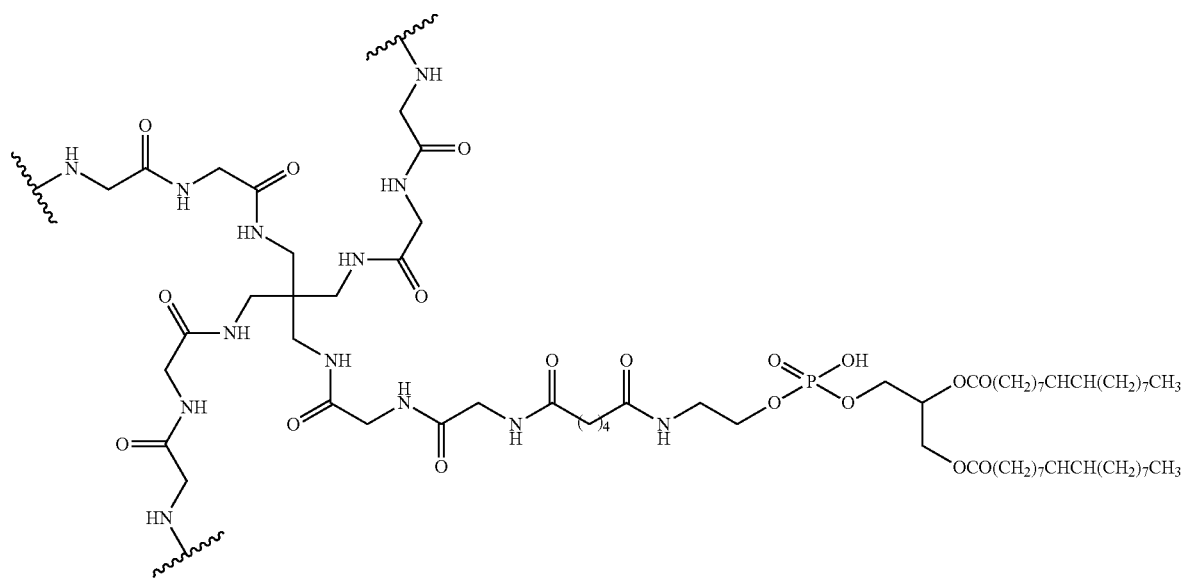

In a first embodiment of the first aspect of the invention F is an aminoalkylglycoside and the multivalent ligand-lipid construct is of the structure:

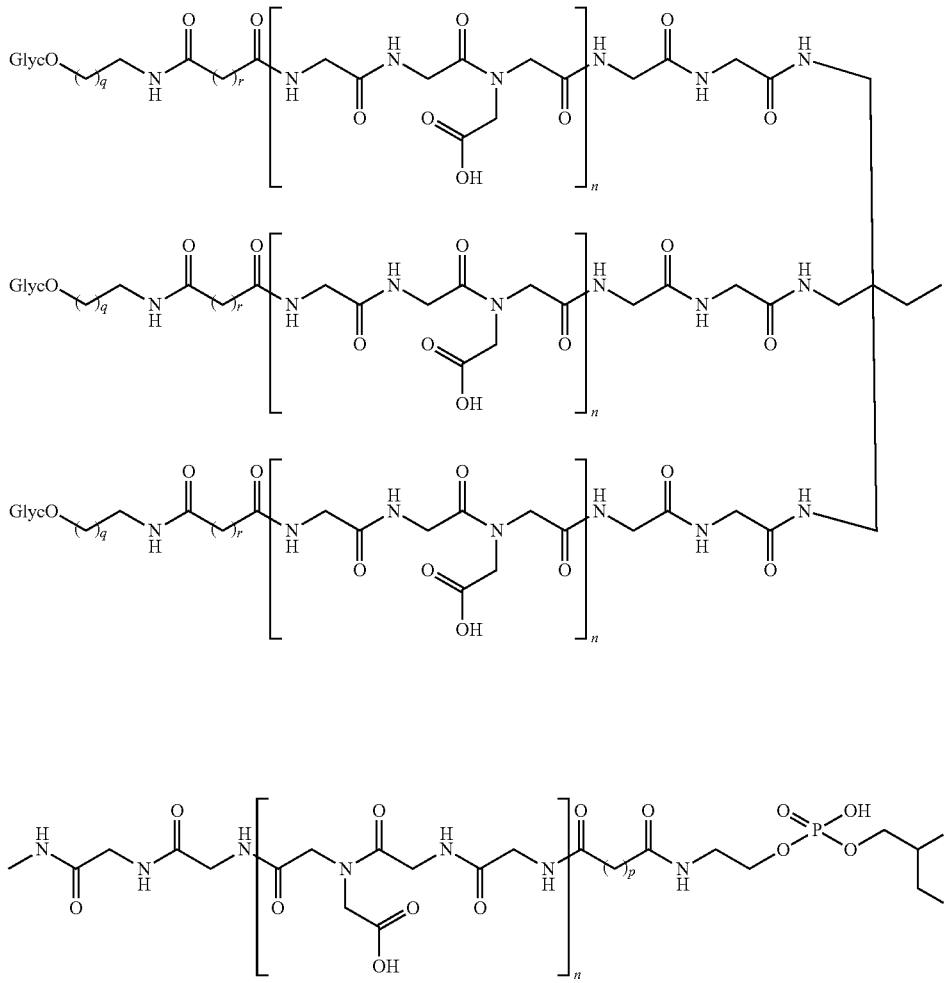

where Glyc is a glycan and q and r are integers independently selected from 1, 2, 3 and 4.

Preferably, Glyc is a glycan selected from the group consisting of: (Neu5Acα6Galβ4GlcNAcβ2Manα)$_2$3, 6Manβ4GlcNAcβ4GlcNAcβ (YDS); Fucα2Galβ (H$_{di}$); Fucα2Galβ3(Fucα4)GlcNAcβ (Le$^b$); Fucα2Galβ3GlcNAcβ3Galβ4Glcβ (LNFP I); Fucα2Galβ4(Fucα3)GlcNAcβ (Le$^y$); Fucα2Galβ4GlcNAcβ (H2); Galα; Galβ1-3(Fucα1-3)GlcNAc; Galβ1-3(Fucα1-4)GlcNAcβ1-4GlcNAc; Galβ1-3GlcNAcβ1-4GlcNAc; Galβ1-3GlcNAc; Galβ1-4(Fucα1-3)GlcNAcβ1-4GlcNAc; Galβ1-4(Fucα1-3) GlcNAc; Galβ1-4GlcNAcβ1-4GlcNAc; Galβ1-4GlcNAc; Galα3(Fucα2)Galβ (B$_{tri}$); Galα3(Fucα2)Galβ3(Fucα4) GlcNAcβ (Ble$^b$); Galα3(Fucα2)Galβ3GalNAcα (B3); Galα3(Fucα2)Galβ3GalNAcβ (B4); Galα3(Fucα2) Galβ3GlcNAcβ (B1); Galα3(Fucα2)Galβ4(Fucα3) GlcNAcβ (Ble$^y$); Galα3(Fucα2)Galβ4GlcNAcβ (B2); Galα3Galβ4GlcNAcβ (Galili); Galα4Galβ4GlcNAcβ (P1); Galα4Galβ4Glcβ (Gb3 (P$^k$)); Galα4GlcNAcβ (α-LN); GalNAcα3(Fucα2)Galβ (A$_{tri}$); GalNAcα3(Fucα2)Galβ3 (Fucα4)GlcNAcβ (ALe$^b$); GalNAcα3(Fucα2) Galβ3GalNAcα (A3); GalNAcα3(Fucα2)Galβ3GalNAcβ (A4); GalNAcα3(Fucα2)Galβ3GlcNAcβ (A1); GalNAcα3 (Fucα2)Galβ4(Fucα3)GlcNAcβ (ALe$^y$); GalNAcα3 (Fucα2)Galβ4GlcNAcβ (A2); GalNAcα3GalNAcβ (Fs2); GalNAcα3GalNAcβ3Galα4Galβ4Glcβ (Fs5); GalNAcα3Galβ (A$_{di}$); GalNAcα3Galβ4GlcNAcβ; GalNAcβ; GalNAcβ3Galα4Galβ4Glcβ (P); GalNH$_2$α3 (Fucα2)Galβ (AcqB); Galβ; Galβ3(Fucα4)GlcNAcβ (Le$^a$); Galβ3GalNAcα (TF); Galβ3GalNAcβ4Galβ4Glcβ (GA1); Galβ4(Fucα3)GlcNAcβ (Le$^x$); Galβ4GlcNAcβ3Galβ4GlcNAcβ (i(LN$_2$)); Galβ4GlcNAcβ3Galβ4Glcβ (LNnT); Galβ4Glcβ (Lac); GlcAβ3[GlcNAcβ4GlcAβ3]$_n$GlcNAc-aminoalditol (hyaluronate); Manα6(Manα3)Manβ (Man$_3$); Neu5Acα3Galβ4GlcNAcβ (Neu5Ac3'LN); Neu5Acα3Galβ4Glcβ (Neu5Ac3'Lac); Neu5Acα6GalNAcα (SiaTn); Neu5Acα6Galβ4GlcNAcβ

(Neu5Ac6'LN); Neu5Gcα3Galβ4GlcNAcβ (Neu5Gc3'LN); SAaβ1-3Galβ1-3(Fucα1-4)GlcNAcβ1-3Galβ1-4(Fucα1-3)Glc; SAβ2-3Galβ1-3(Fucα1-4)GlcNAcβ1-3Galβ1-4(Fucα1-3)GlcNAcβ1-3Galβ1-4Glc; SAa2-3Galβ1-3(Fucα1-4)GlcNAcβ1-3Galβ1-4(Fucα1-3)GlcNAcβ1-3Galβ1-4(Fucα1-3)Glc; SAa2-3Galβ1-3(Fucα1-4)GlcNAcβ1-3Galβ1-4(Fucα1-3)GlcNAc; SAa2-3Galβ1-3(Fucα1-4)GlcNAcβ1-3Galβ1-4Glc; SAa2-3Galβ1-3(Fucα1-4)GlcNAcβ1-4Gal; SAa2-3Galβ1-3(Fucα1-4)GlcNAcβ1-4GlcNAc; SAa2-3Galβ1-3(Fucα1-4)GlcNAc; SAa2-3Galβ1-3GlcNAcβ1-4Galβ1-4(Fucα1-3)GlcNAcβ1-3Galβ1-4(Fucα1-3)Glc; SAa2-3Galβ1-3GlcNAcβ1-4Galβ1-4(Fucα1-3)GlcNAcβ1-3Galβ1-4Glc; SAa2-3Galβ1-3GlcNAcβ1-4Galβ1-4(Fucα1-3)GlcNAc; SAa2-3Galβ1-3GlcNAcβ1-4GlcNAc; SAa2-3Galβ1-3GlcNAc; SAa2-3Galβ1-4(Fucα1-3)GlcNAcβ1-3Galβ1-3(Fucα1-4)Glc; SAa2-3Galβ1-4(Fucα1-3)GlcNAcβ1-3Galβ1-3(Fucα1-4)GlcNAcβ1-3Galβ1-4Glc; SAa2-3Galβ1-4(Fucα1-3)GlcNAcβ1-3Galβ1-3(Fucα1-4)GlcNAcβ1-3Galβ1-4(Fucα1-3)Glc; SAa2-3Galβ1-4(Fucα1-3)GlcNAcβ1-3Galβ1-4(Fucα1-3)Glc; SAa2-3Galβ1-4(Fucα1-3)GlcNAcβ1-3Galβ1-4Glc; SAa2-3Galβ1-4(Fucα1-3)GlcNAcβ1-3Galβ1-4(Fucα1-3)GlcNAcβ1-3Galβ1-4(Fucα1-3)Glc; SAa2-3Galβ1-4(Fucα1-3)GlcNAcβ1-3Galβ1-4Glc; SAa2-3Galβ1-4(Fucα1-3)GlcNAcβ1-4Gal; SAa2-3Galβ1-4(Fucα1-3)GlcNAcβ1-4GlcNAc; SAa2-3Galβ1-4(Fucα1-3)GlcNAc; SAa2-3Galβ1-4Glc; SAa2-3Galβ1-4GlcNAcβ1-3Galβ1-3(Fucα1-4)GlcNAcβ1-3Galβ1-4(Fucα1-3)Glc; SAa2-3Galβ1-4GlcNAcβ1-3Galβ1-4(Fucα1-3)GlcNAcβ1-3Galβ1-4Glc; SAa2-3Galβ1-4GlcNAcβ1-3Galβ1-4(Fucα1-3)GlcNAcβ1-3Galβ1-4(Fucα1-3)Glc; SAa2-3Galβ1-4GlcNAcβ1-3Galβ1-4GlcNAcβ1-3Galβ1-4Glc; SAa2-3Galβ1-4GlcNAcβ1-3Galβ1-4(Fucα1-3)GlcNAc; SAa2-3Galβ1-4GlcNAcβ1-4GlcNAc; SAa2-3Galβ1-4GlcNAc; SAa2-6Galβ1-3(Fucα1-4(GlcNAc; SAa2-6Galβ1-3(Fucα1-4)GlcNAcβ1-3Galβ1-4(Fucα1-3)Glc; SAa2-6Galβ1-3(Fucα1-4)GlcNAcβ1-3Galβ1-4(Fucα1-3)GlcNAcβ1-3Galβ1-4Glc; SAa2-6Galβ1-3(Fucα1-4)GlcNAcβ1-3Galβ1-4(Fucα1-3)GlcNAcβ1-3Galβ1-4(Fucα1-3)Glc; SAa2-6Galβ1-3(Fucα1-4)GlcNAcβ1-3Galβ1-4(Fucα1-3)GlcNAc; SAa2-6Galβ1-3(Fucα1-4)GlcNAcβ1-3Galβ1-4Glc; SAa2-6Galβ1-3GlcNAcβ1-4Galβ1-4(Fucα1-3)GlcNAcβ1-3Galβ1-4Glc; SAa2-6Galβ1-3GlcNAcβ1-4Galβ1-4(Fucα1-3)GlcNAc; SAa2-6Galβ1-4(Fucα1-3)GlcNAcβ1-3Galβ1-3(Fucα1-4)Glc; SAa2-6Galβ1-4(Fucα1-3)GlcNAcβ1-3Galβ1-3(Fucα1-4)GlcNAcβ1-3Galβ1-4(Fucα1-3)Glc; SAa2-6Galβ1-4(Fucα1-3)GlcNAcβ1-3Galβ1-4(Fucα1-3)Glc; SAa2-6Galβ1-4(Fucα1-3)GlcNAcβ1-3Galβ1-4(Fucα1-3)GlcNAcβ1-3Galβ1-4(Fucα1-3)Glc; SAa2-6Galβ1-4(Fucα1-3)GlcNAcβ1-3Galβ1-4(Fucα1-3)Glc; SAa2-6Galβ1-4(Fucα1-3)GlcNAcβ1-3Galβ1-4Glc; SAa2-6Galβ1-4GlcNAcβ1-3Galβ1-3(Fucα1-4)GlcNAcβ1-3Galβ1-4(Fucα1-3)Glc; SAa2-6Galβ1-4GlcNAcβ1-3Galβ1-3(Fucα1-4)GlcNAcβ1-3Galβ1-4Glc; SAa2-6Galβ1-4GlcNAcβ1-3Galβ1-4(Fucα1-3)GlcNAcβ1-3Galβ1-4(Fucα1-3)Glc; SAa2-6Galβ1-4GlcNAcβ1-3Galβ1-4(Fucα1-3)GlcNAcβ1-3Galβ1-4Glc; SAa2-6Galβ1-4GlcNAcβ1-3Galβ1-4(Fucα1-3)GlcNAcβ1-3Galβ1-4(Fucα1-3)Glc; SAa2-6Galβ1-4GlcNAcβ1-3Galβ1-4(Fucα1-3)GlcNAc; SAa2-6Galβ1-4GlcNAcβ1-3Galβ1-4GlcNAc; SAa2-6Galβ1-4GlcNAc; SAa2-3Galβ1-4(Fucα1-3)GlcNAcβ1-3Galβ1-3(Fucα1-4)GlcNAc; SAa2-3Galβ1-4GlcNAcβ1-3Galβ1-3(Fucα1-4)GlcNAc; SAa2-6Galβ1-4(Fucα1-3)GlcNAcβ1-3Galβ1-3(Fucα1-4)GlcNAc and SAa2-6Galβ1-4GlcNAcβ1-3Galβ1-3(Fucα1-4)GlcNAc. More preferably, Glyc is a glycan selected from the group consisting of: (Neu5Acα6Galβ4GlcNAcβ2Manα)$_2$3,6Manβ4GlcNAcβ4GlcNAcβ (YDS); Fucα2Galβ (H$_{di}$); Fucα2Galβ3(Fucα4)GlcNAcβ (Le$^b$); Fucα2Galβ3GlcNAcβ3Galβ4Glcβ (LNFP I); Fucα2Galβ4(Fucα3)GlcNAcβ (Le$^y$); Fucα2Galβ4GlcNAcβ (H2); Galα; Galα3(Fucα2)Galβ (B$_{tri}$); Galα3(Fucα2)Galβ3(Fucα4)GlcNAcβ (Ble$^b$); Galα3(Fucα2)Galβ3GalNAcα (B3); Galα3(Fucα2)Galβ3GalNAcβ (B4); Galα3(Fucα2)Galβ3GlcNAcβ (B1); Galα3(Fucα2)Galβ4(Fucα3)GlcNAcβ (Ble$^y$); Galα3(Fucα2)Galβ4GlcNAcβ (B2); Galα3Galβ4GlcNAcβ (Galili); Galα4Galβ4GlcNAcβ (P1); Galα4Galβ4Glcβ (Gb3 (P$^k$)); Galα4GlcNAcβ (α-LN); GalNAcα3(Fucα2)Galβ (A$_{tri}$); GalNAcα3(Fucα2)Galβ3(Fucα4)GlcNAcβ (ALe$^b$); GalNAcα3(Fucα2)Galβ3GalNAcα (A3); GalNAcα3(Fucα2)Galβ3GalNAcβ (A4); GalNAcα3(Fucα2)Galβ3GlcNAcβ (A1); GalNAcα3(Fucα2)Galβ4(Fucα3)GlcNAcβ (ALe$^y$); GalNAcα3(Fucα2)Galβ4GlcNAcβ (A2); GalNAcα3GalNAcβ (Fs2); GalNAcα3GalNAcβ3Galα4Galβ4Glcβ (Fs5); GalNAcα3Galβ (Ac); GalNAcα3Galβ4GlcNAcβ; GalNAcβ; GalNAcβ3Galα4Galβ4Glcβ (P); GalNH$_2$α3(Fucα2)Galβ (AcqB); Galβ; Galβ3(Fucα4)GlcNAcβ (Le$^a$); Galβ3GalNAcα (TF); Galβ3GalNAcβ4Galβ4Glcβ (GA1); Galβ4(Fucα3)GlcNAcβ (Le$^x$); Galβ4GlcNAcβ3Galβ4GlcNAcβ (i(LN$_2$)); Galβ4GlcNAcβ3Galβ4Glcβ (LNnT); Galβ4Glcβ (Lac); GlcAβ3[GlcNAcβ4GlcAβ3]$_n$GlcNAc-aminoalditol (hyaluronate); Manα6(Manα3)Manβ (Man$_3$); Neu5Acα3Galβ4GlcNAcβ (Neu5Ac3'LN); Neu5Acα3Galβ4Glcβ (Neu5Ac3'Lac); Neu5Acα6GalNAcα β (SiaTn); Neu5Acα6Galβ4GlcNAcβ (Neu5Ac6'LN) and Neu5Gcα3Galβ4GlcNAcβ (Neu5Gc3'LN). Most preferably, Glyc is a glycan selected from the group consisting of: Galα3Galβ4GlcNAcβ (Galili) and GalNAcα3Galβ4GlcNAcβ.

In a second embodiment of the first aspect of the invention F is an oligopeptide comprising an N-maleoyl-β-alanine conjugated Cys residue and the multivalent ligand-lipid construct is of the structure:

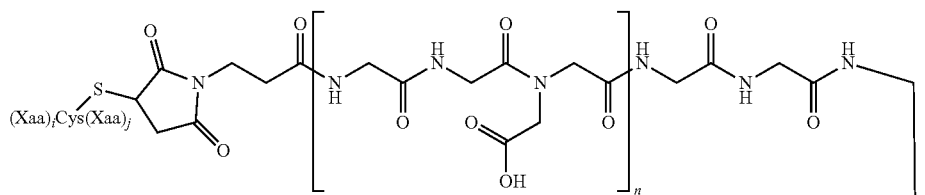

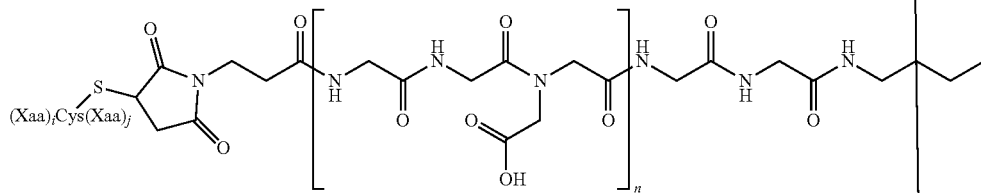

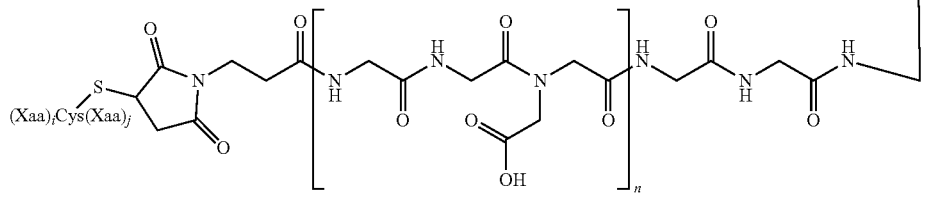

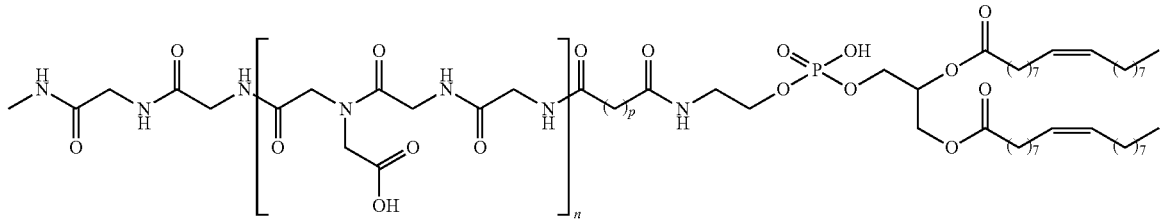

where Xaa is an amino acid residue and i and j are either zero or integers the sum of which is in the range 5 to 30 inclusive. Preferably, i is an integer in the range 5 to 30 inclusive and j is zero. More preferably, i is the integer 13 and j is zero. Most preferably, the oligopeptide is the peptide of SEQ ID NO: 01.

In a second aspect the invention provides an improved method of detecting the presence of a ligand binding protein in a biological sample obtained from a subject comprising the steps of:

contacting the biological sample with a first suspension of cells modified by incorporation into the membranes of the cells multivalent ligand-lipid constructs of the first aspect of the invention to provide a second suspension;

adding an amount of anti-subject binding protein to the second suspension and incubating at a temperature and for a time sufficient to permit agglutination of the cell; and determining the degree of agglutination, where the ligand binding protein binds to F of the ligand-lipid constructs of the first aspect of the invention.

The improvement in the improved method is an increase in avidity, sensitivity and/or specificity of the method of detecting the presence of a ligand binding protein in a biological sample relative to the use of a monovalent ligand-lipid construct.

In a third aspect the invention provides a method of determining the ability of a ligand to induce complement mediated cell lysis in the serum of a subject comprising the steps of:

contacting a sample of serum obtained from the subject with a suspension of O group red blood cells modified by incorporation into the membranes of the cells multivalent ligand-lipid constructs of the first aspect of the invention; and then monitoring the rate of haemolysis, where F is the ligand.

In a fourth aspect the invention provides a method of treating patients with tumours by intratumoural injection of a composition consisting essentially of a construct of one or more multivalent ligand-lipid constructs of the first aspect of the invention.

In the description and claims of this specification the following acronyms, symbols, terms and phrases have the meaning provided: "affinity" means the strength of the interaction between two entities, e.g. between enzyme and substrate or receptor and ligand; "avidity" means the strength of a binding interaction, e.g. the binding interaction of antibody with antigen; "biocompatible" means not harmful or toxic to living tissue; "comprising" means "including", "containing" or "characterized by" and does not exclude any additional element, ingredient or step; "consisting of" means excluding any element, ingredient or step not specified except for impurities and other incidentals; "consisting essentially of" means excluding any element, ingredient or step that is a material limitation; "diagnostic" means concerned with the diagnosis of illness or other problems; "DOPE" means 1,2-O-dioleoyl-sn-glycero-3-phosphatidylethanolamine; "glycan" means a mono-, di-, tri- or oligosaccharide; "kodecyte" means a cell modified by incorporation into the cell membrane of a construct; "PBS"

denotes phosphate buffered saline; "PCV" or "pcv" denotes packed cell volume; "plasma" means the colourless fluid part of blood or lymph, in which corpuscles or fat globules are suspended; "prognostic" means predicting the likely cause or occurrence of a disease or ailment; "prophylactic" means intended to prevent disease; "RBC" denotes red blood cell; "reaction product" means the product of a reaction prior to purification; "saline" means a solution of one or more salts; "serum" means the amber-coloured, protein-rich liquid which separates out when blood coagulates; "synthetic" means prepared by chemical synthesis; "therapeutic" means relating to the healing of disease; "water dispersible" means, in the context of describing the properties of constructs, a stable, single phase system is formed at a temperature of 25° C. when the construct is contacted with water at a concentration of at least 100 μg/mL and in the absence of organic solvents or detergents.

Amino acid residues are identified using the symbols provided in Table 3 of Appendix 2 of Annex C of the Administrative Instructions under the Patent Corporation Treaty (as in force from 1 Jul. 2015). "Functionally similar amino acid" means an amino acid with similar properties according to the following groupings: neutral-weakly hydrophobic (Ala, Gly, Pro, Ser, Thr); hydrophilic-acid amine (Asn, Asp, Gln, Glu); hydrophilic-basic (Arg, His, Lys); hydrophobic (Ile, Met, Leu, Val); hydrophobic-aromatic (Phe, Trp, Tyr) and cross-linking (Cys).

Saccharide residues and their derivatives are identified using the symbols provided in Table 2 and the appendix of the publication of McNaught (1996). Specifically, the following symbols have the meaning provided: "Abe" means abequose; "All" means allose; "Alt" means altrose; "Api" means apiose; "Ara" means arabinose; "dRib" means 2-deoxyribose; "Fru" means fructose; "Fuc" means fucose; "Fuc-ol" means fucitol; "Gal" means galactose; "Gal" means galactose; "GalN" means galactosamine; "GalNAc" means N-acetylgalactosamine; "Glc" means glucose; "GlcA" means glucuronic acid; "GlcN" means glucosamine; "GlcN3N" means 2,3-diamino-2,3-dideoxy-D-glucose; "GlcNAc" means N-acetylglucosamine; "Glc-ol" means glucitol; "GlcpA6Et" means ethyl glucopryanuronate; "Gul" means gulose; "Gul" means gulose; "Ido" means idose; "IdoA" means iduronic acid; "Kdo" means 3-deoxy-D-manno-oct-2-ulosonic acid; "Lyx" means lyxose; "Man" means mannose; "Mur" means muramic acid; "Neu" means neuraminic acid; "Neu2en5Ac" means N-acetyl-2-deoxyneur-2-enaminic acid; "Neu5Ac" means n-acetylneuraminic acid; "Neu5Gc" means N-glucoloylneuraminic acid; "Psi" means psicose; "Qui" means quinovose; "Rha" means rhamnose; "Rha3,4Me$_2$" means 3,4-di-O-methylrhamnose; "Rib" means ribose; "Rib5P" means ribose 5-phosphate; "Ribulo (or Rul)" means ribulose; "SA" means sialic acid; Sor" means sorbose; "Tag" means tagatose; "Tal" means talose; "Xyl" means xylose; "Xyl2CMe" means 2-C-methylxylose; "Xylulo (or Xul)" means xylulose and "β-D-Galp4S" means β-D-galactopyranose 4-sulfate.

The terms "first", "second", "third", etc. used with reference to elements, features or integers of the subject matter defined in the Statement of Invention and Claims, or when used with reference to alternative aspects or embodiments of the invention are not intended to imply an order of preference.

Where concentrations or ratios of reagents are specified the concentration or ratio specified is the initial concentration or ratio of the reagents. Where values are expressed to one or more decimal places standard rounding applies. For example, 1.7 encompasses the range 1.650 recurring to 1.749 recurring.

In the absence of further limitation the use of plain bonds in the representations of the structures of compounds encompasses the diastereomers, enantiomers and mixtures thereof of the compounds. In the representations of the structures, partial structures or substructures of constructs the repeat of a divalent radical is represented by:

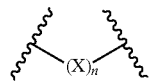

where —X— is the divalent radical repeated n times. Where the divalent radical is methylene (—CH$_2$—) the repeat of this divalent radical is represented by:

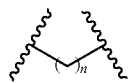

The invention will now be described with reference to embodiments or examples and the figures of the accompanying drawings pages.

DESCRIPTION OF EMBODIMENTS

Figure 1:
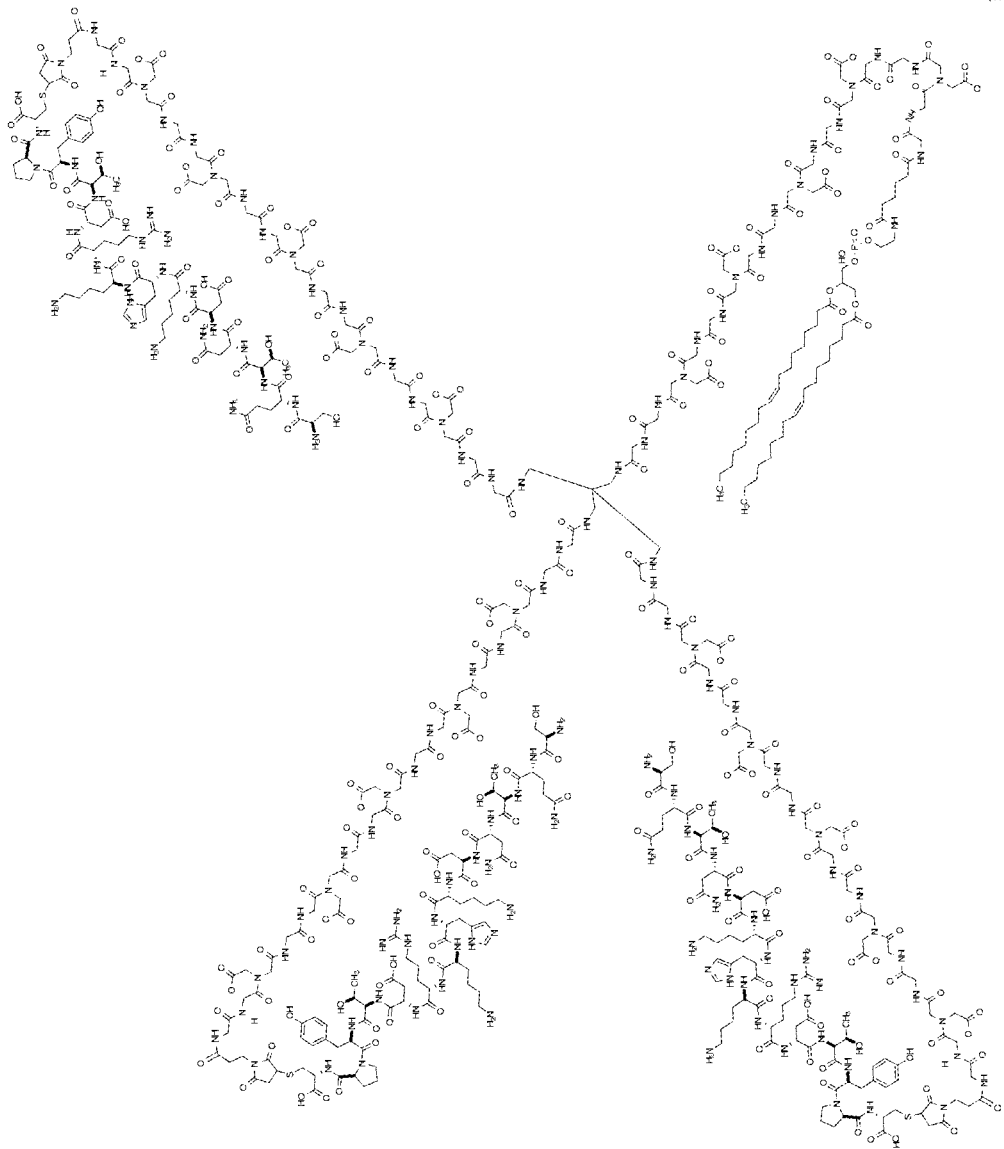
FIG. 1. Alternative representation of the construct designated (MUT21-Mal-βAla-CMG3-NHCH$_2$)$_3$CCH$_2$NH-CMG3-Ad-DOPE (26).

The multivalent presentation of ligands is particularly advantageous where the ligands are glycans. The affinities of glycan-binding proteins (GBPs) for glycan ligands in the monovalent state are generally very low. The multivalent presentation of glycan ligands permits GBPs such as antibodies to bind with increased avidity. In general, the multivalent presentation of glycan ligands amplifies differences in specificity of binding of GBPs relative to the low intrinsic affinities of GBPs for their glycan ligands. As a result the presence of GBPs in human sera may be detected using simple agglutination or cell lysis assays.

Chemistry

Preparation of (Boc-Gly$_2$-HNCH$_2$)$_4$C (3) (Step i of Scheme I)

Tetraamine (H$_2$N—CH$_2$)$_4$C (1) was synthesized according the method disclosed in the publication of Litherland et al (1938). To a stirred solution of the tetraamine 1 (500 mg, 1.52 mmol) in a mixture of 1M aqueous NaHCO$_3$ (18.2 ml) and i-PrOH (9 ml), Boc-GlyGlyNos (2) (4012 mg, 12.18 mmol) was added (CO$_2$ evolution, foaming). The reaction mixture was stirred for 30 min, then 6 ml of 1M aqueous NaHCO$_3$ was added and the mixture stirred overnight.

Precipitate of (Boc-Gly$_2$-HNCH$_2$)$_4$C (3) was filtered, washed thoroughly with methanol/water mixture (1:1, 20 ml) and dried in vacuum. Yield 1470 mg (98%), white solid.

$^1$H NMR (500 MHz, [D$_6$]DMSO, 30° C.) δ, ppm: 8.491 (t, J=5.6 Hz, 1H; NHCO), 7.784 (t, J=6.6 Hz, 1H; C—CH$_2$—NHCO), 6.858 (t, J=6 Hz, 1H; NHCOO), 3.696 (d, J=5.6 Hz, 2H; COCH$_2$NH), 3.675 (d, J=6 Hz, 2H; COCH$_2$NHCOO), 2.685 (d, J=6.6 Hz, 2H; C—CH$_2$NH), 1.375 (s, 9H; C(CH$_3$)$_3$).

Preparation of (CF$_3$COOH.H-Gly$_2$-NHCH$_2$)$_4$C (4) (Step ii of Scheme I)

The (Boc-Gly$_2$-HNCH$_2$)$_4$C (3) (1450 mg, 1.466 mmol) was dissolved in CF$_3$COOH (5 ml) and the solution was kept for 2 h at room temperature. Trifluoroacetic acid was removed under vacuum and the residue was three times extracted with (CH$_3$CH$_2$)$_2$O (slight agitation with 30 ml of (CH$_3$CH$_2$)$_2$O for 30 min., followed by decantation) to eliminate residual CF$_3$COOH. Solid residue was dried under vacuum, dissolved in a minimum volume of water and passed through a Sephadex LH-20 column and elutd with water. Fractions, containing product 4, were combined, evaporated to c. 5 ml and freeze dried. Yield 1424 mg (93%), white solid. TLC: R$_f$ 0.5 (ethanol/conc. NH$_3$; 2:1 (v/v)).

$^1$H NMR (500 MHz, [D$_2$]H$_2$O, 30° C.) δ, ppm: 4.028 (s, 2H; COCH$_2$NH), 3.972 (s, 2H; COCH$_2$NH), 2.960 (s, 2H; C—CH$_2$NH).

Preparation of ([2-(2-tert-butoxycarbonylamino-acetylamino)-acetyl]-methoxy-carbonylmethyl-amino)-acetic acid methyl ester (7) (Step i of Scheme II)

To a stirred solution of (methoxycarbonylmethyl-amino)-acetic acid methyl ester hydrochloride (5) (988 mg, 5 mmol) in DMF (15 ml) Boc-GlyGlyNos (2) (3293 mg, 10 mmol) and (CH$_3$CH$_2$)$_3$N (3475 μL, 25 mmol) were added. The mixture was stirred overnight at room temperature and then diluted with o-xylene (70 ml) and evaporated. Flash column chromatography on silica gel (packed in toluene, and eluted with ethyl acetate) resulted in a crude product. The crude product was dissolved in chloroform and washed sequentially with water, 0.5 M NaHCO$_3$ and saturated KCl. The chloroform extract was evaporated and the product purified on a silica gel column (packed in chloroform and eluted with 15:1 (v/v) chloroform/methanol). Evaporation of the fractions and drying under vacuum of the residue provided a colourless thick syrup of product 7. Yield 1785 mg, (95%). TLC: R$_f$=0.49 (7:1 (v/v) chloroform/methanol).

$^1$H NMR (500 MHz, [D$_6$]DMSO, 30° C.) δ, ppm: 7.826 (t, J=5.1 Hz, 1H; NHCO), 6.979 (t, J=5.9 Hz, 1H; NHCOO), 4.348 and 4.095 (s, 2H; NCH$_2$COO), 3.969 (d, J=5.1 Hz, 2H; COCH$_2$NH), 3.689 and 3.621 (s, 3H; OCH$_3$), 3.559 (d, J=5.9 Hz, 2H; COCH$_2$NHCOO), 1.380 (s, 9H; C(CH$_3$)$_3$).

Preparation of {[2-(2-tert-butoxycarbonylamino-acetylamino)-acetyl]-methoxycarbonylmethyl-amino}-acetic acid (8) (Step ii of Scheme II)

To a stirred solution of 7 (1760 mg, 4.69 mmol) in methanol (25 ml) 0.2 M aqueous NaOH (23.5 ml) was added and the solution kept for 5 min at room temperature. The solution was then acidified with acetic acid (0.6 ml) and evaporated to dryness. Column chromatography of the residue on silica gel (packed in ethyl acetate and eluted with 2:3:1 (v/v/v) i-PrOH/ethyl acetate/water) resulted in a recovered 7 (63 mg, 3.4%) and target compound 8 (1320 mg). The intermediate product was then dissolved in methanol/water/pyridine mixture (20:10:1, 30 ml) and passed through an ion exchange column (Dowex 50X4-400, pyridine form, 5 ml) to remove residual sodium cations. The column was then washed with the same solvent mixture, the eluant evaporated, the residue dissolved in chloroform/benzene mixture (1:1, 50 ml) and then evaporated and dried under vacuum. Yield of product 8 was 1250 mg (74%), white solid. TLC: R$_f$ 0.47 (4:3:1 (v/v/v) i-PrOH/ethyl acetate/water).

$^1$H NMR (500 MHz, [D$_6$]DMSO, 30° C.), mixture of cis- and trans-conformers of N-carboxymethylglycine unit c.3:1. Major conformer; δ, ppm: 7.717 (t, J=5 Hz, 1H; NHCO), 7.024 (t, J=5.9 Hz, 1H; NHCOO), 4.051 (s, 2H; NCH$_2$COOCH$_3$), 3.928 (d, J=5 Hz, 2H; COCH$_2$NH), 3.786 (s, 2H; NCH$_2$COOH), 3.616 (s, 3H; OCH$_3$), 3.563 (d, J=5.9 Hz, 2H; COCH$_2$NHCOO), 1.381 (s, 9H; C(CH$_3$)$_3$) ppm; minor conformer, δ=7.766 (t, J=5 Hz, 1H; NHCO), 7.015 (t, J=5.9 Hz, 1H; NHCOO), 4.288 (s, 2H; NCH$_2$COOCH$_3$), 3.928 (d, J=5 Hz, 2H; COCH$_2$NH), 3.858 (s, 2H; NCH$_2$COOH), 3.676 (s, 3H; OCH$_3$), 3.563 (d, J=5.9 Hz, 2H; COCH$_2$NHCOO), 1.381 (s, 9H; C(CH$_3$) 3).

SCHEME I

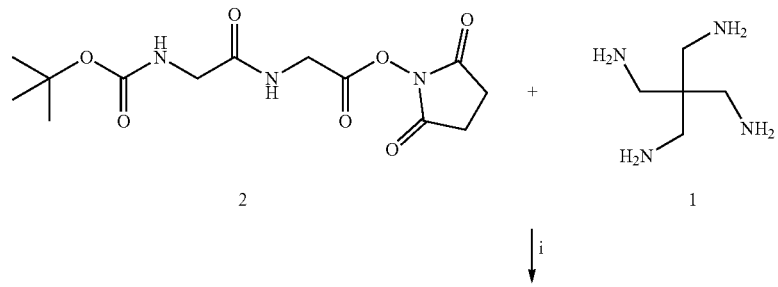

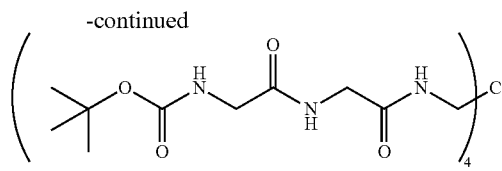

3

↓ ii

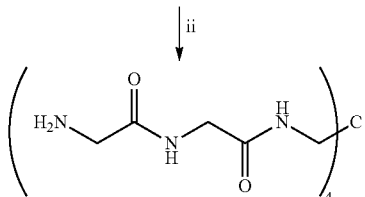

4

Preparation of ([2-(2-tert-Butoxycarbonylamino-acetylamino)-acetyl]-methoxycarbonylmethyl-amino)-acetic acid N-oxysuccinimide ester (Boc-Gly$_2$(MCMGly)Nos) (9) (Step iii of Scheme III)

To an ice-cooled stirred solution of 8 (1200 mg, 3.32 mmol) and N-hydroxysuccinimide (420 mg, 3.65 mmol) in DMF (10 ml) was added N,N'-dicyclohexylcarbodiimide (754 mg, 3.65 mmol). The mixture was stirred at 0° C. for 30 min, then for 2 hours at room temperature. The precipitate of N,N'-dicyclohexylurea was filtered off, washed with DMF (5 ml), and filtrates evaporated to a minimal volume. The residue was then agitated with (CH$_3$CH$_2$)$_2$O (50 ml) for 1 hour and an ether extract removed by decantation. The residue was dried under vacuum providing the ester 9 (1400 mg, 92%) as a white foam. TLC: R$_f$ 0.71 (40:1 (v/v) acetone/acetic acid).

$^1$H NMR (500 MHz, [D$_6$]DMSO, 30° C.), mixture of cis- and trans-conformers of N-carboxymethylglycine unit c. 3:2.

Major conformer; δ, ppm: 7.896 (t, J=5.1 Hz, 1H; NHCO), 6.972 (t, J=5.9 Hz, 1H; NHCOO), 4.533 (s, 2H; NCH$_2$COON), 4.399 (s, 2H; NCH$_2$COOCH$_3$), 3.997 (d, J=5.1 Hz, 2H; COCH$_2$NH), 3.695 (s, 3H; OCH$_3$), 3.566 (d, J=5.9 Hz, 2H; COCH$_2$NHCOO), 1.380 (s, 9H; C(CH$_3$)$_3$).

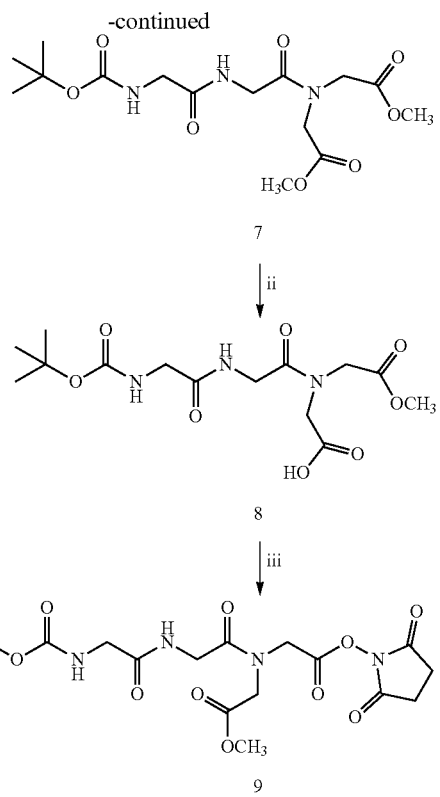

Minor conformer; δ, ppm: 7.882 (t, J=5.1 Hz, 1H; NHCO), 6.963 (t, J=5.9 Hz, 1H; NHCOO), 4.924 (s, 2H; NCH$_2$COON), 4.133 (s, 2H; NCH$_2$COOCH$_3$), 4.034 (d, J=5.1 Hz, 2H; COCH$_2$NH), 3.632 (s, 3H; OCH$_3$), 3.572 (d, J=5.9 Hz, 2H; COCH$_2$NHCOO), 1.380 (s, 9H; C(CH$_3$)$_3$).

The ester 9 (1380 mg) was dissolved in DMSO to provide a volume of 6 ml and used as a 0.5 M solution (stored at −18° C.).

Preparation of {Boc-[Gly$_2$(MCMGly)]Gly$_2$-NHCH$_2$}$_4$C (10) (Step i of Scheme III)

To a stirred solution of (CF$_3$COOH.H-Gly$_2$-HNCH$_2$)$_4$C (4) (277 mg, 0.265 mmol) in DMSO (2 ml) the ester 9 (1.591 mmol, 3.18 ml of 0.5 M solution in DMSO) and (CH$_3$CH$_2$)$_3$N (295 μL, 2.121 mmol) were added. The mixture was stirred overnight at room temperature, acidified with 150 μL

SCHEME II

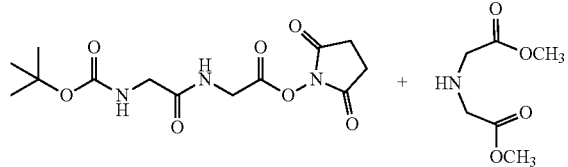

AcOH and solvent removed under vacuum (freeze drying). The residue was extracted three times with (CH$_3$CH$_2$)$_2$O (slight agitation with 20 ml of (CH$_3$CH$_2$)$_2$O for 30 min followed by decantation). The solid residue was dissolved in a minimal volume of acetone and fractionated on silica gel column (packed in acetone and eluted with acetone, 20:2:1 (v/v/v) acetone/methanol/water and 15:2:1 (v/v/v) acetone/methanol/water). Selected fractions were evaporated and the residue was dried under vacuum. The yield of pure {Boc-[Gly$_2$(MCMGly)]Gly$_2$-NHCH$_2$}$_4$C (10) was 351 mg (68%), white solid. TLC: R$_f$ 0.38 (15:2:1 (v/v/v) acetone/methanol/water).

$^1$H NMR (500 MHz, [D$_6$]DMSO, 30° C.), mixture of cis- and trans-conformers of N-carboxymethylglycine unit in chain c. 3:2.

Major conformer; δ, ppm: 8.593 (t, J=5 Hz, 1H; NHCO), 8.335 (t, J=5.4 Hz, 1H; NHCO), 7.821 (t, J=6.4 Hz, 1H; C—CH$_2$—NHCO), 7.786 (t, J=5.1 Hz, 1H; NHCO), 6.993 (t, J=6 Hz, 1H; NHCOO), 4.139 (s, 2H; NCH$_2$CO), 4.074 (s, 2H; NCH$_2$COO(CH$_3$)), 3.985 (d, J=5 Hz, 2H; COCH$_2$NH), 3.887 (d, J=5.4 Hz, 2H; COCH$_2$NH), 3.726 (d, J=5.1 Hz, 2H; COCH$_2$NH), 3.634 (s, 3H; OCH$_3$), 3.567 (d, J=6 Hz, 2H; COCH$_2$NHCOO), 2.686 (broad. d, J=6.4 Hz, 2H; C—CH$_2$NH), 1.379 (s, 9H; C(CH$_3$)$_3$).

Minor conformer; δ, ppm: 8.511 (t, J=5 Hz, 1H; NHCO), 8.158 (t, J=5.4 Hz, 1H; NHCO), 7.821 (t, J=6.4 Hz, 1H; C—CH$_2$—NHCO), 7.786 (t, J=5.1 Hz, 1H; NHCO), 6.993 (t, J=6 Hz, 1H; NHCOO), 4.292 (s, 2H; NCH$_2$CO), 3.998 (s, 2H; NCH$_2$COOCH$_3$), 3.954 (d, J=5 Hz, 2H; COCH$_2$NH), 3.826 (d, J=5.4 Hz, 2H; COCH$_2$NH), 3.715 (d, J=5.1 Hz, 2H; COCH$_2$NH), 3.692 (s, 3H; OCH$_3$), 3.567 (d, J=6 Hz, 2H; COCH$_2$NHCOO), 2.686 (broad. d, J=6.4 Hz, 2H; C—CH$_2$NH), 1.379 (s, 9H; C(CH$_3$)$_3$).

Preparation of (CF$_3$COOH*H-[Gly$_2$ (MCMGly)]Gly$_2$-NHCH$_2$)$_4$C (11) (Step ii of Scheme III)

The {Boc-[Gly$_2$(MCMGly)]Gly$_2$-NHCH$_2$}$_4$C (10) (330 mg, 0.168 mmol) was dissolved in CF$_3$COOH (2 ml) and the solution was kept for 40 min at room temperature. Trifluoroacetic acid was evaporated under vacuum, the residue extracted three times with (CH$_3$CH$_2$)$_2$O (slight agitation with 20 ml of (CH$_3$CH$_2$)$_2$O for 30 min followed by decantation) to eliminate residual CF$_3$COOH, and then dried under vacuum. The yield of {CF$_3$COOH.H-[Gly$_2$(MCMGly)]Gly$_2$-NHCH$_2$}$_4$C (11) was 337 mg (99%), white solid.

$^1$H NMR (500 MHz, [D$_2$]H$_2$O, 30° C.), mixture of cis- and trans-conformers of N-carboxymethylglycine unit in chain c. 11:10.

Major conformer; δ, ppm: 4.370 (s, 2H; NCH$_2$CO), 4.265 (s, 2H; NCH$_2$COOCH$_3$), 4.215 (s, 2H; COCH$_2$NH), 4.138 (s, 2H; COCH$_2$NH), 3.968 (s, 2H; COCH$_2$NH), 3.919 (s, 2H; COCH$_2$NH$_2^+$), 3.775 (s, 3H; OCH$_3$), 2.914 (s, 2H; C—CH$_2$NH).

Minor conformer; δ, ppm: 4.431 (s, 2H; NCH$_2$CO), 4.241 (s, 2H; NCH$_2$COOCH$_3$), 4.239 (s, 2H; COCH$_2$NH), 4.074 (s, 2H; COCH$_2$NH), 3.960 (s, 2H; COCH$_2$NH), 3.919 (s, 2H; COCH$_2$NH$_2$), 3.829 (s, 3H; OCH$_3$), 2.914 (s, 2H; C—CH$_2$NH).

Preparation of (CF$_3$COOH.H-[Gly$_2$(MCMGly)]$_2$Gly$_2$-NHCH$_2$)$_4$C (13) (Steps i and ii of Scheme IV)

To a stirred solution of (CF$_3$COOH.H-[Gly$_2$ (MCMGly)]Gly$_2$-HNCH$_2$)$_4$C (11) (272 mg, 0.135 mmol) in DMSO (2 ml) the ester 9 (0.809 mmol, 1.62 ml of 0.5 M solution in DMSO) and (CH$_3$CH$_2$)$_3$N (112 μL, 0.809 mmol) were added. The mixture was stirred overnight at room temperature, acidified with 70 μL AcOH and solvent removed under vacuum (freeze drying). The residue was extracted three times with (CH$_3$CH$_2$)$_2$O (slight agitation with 15 ml of (CH$_3$CH$_2$)$_2$O for 30 min followed by decantation). Solid residue was dissolved in a minimal volume of 7:1 (v/v) acetone/methanol mixture and fractionated on a silica gel column (packed in acetone and eluted with 7:1 (v/v) acetone/methanol, 10:2:1 (v/v/v), 9:2:1 (v/v/v), 8:2:1 (v/v/v) acetone/methanol/water). Selected fractions were evaporated and the residue was dried in vacuum. The yield of pure {Boc-[Gly$_2$(MCMGly)]$_2$Gly$_2$-NHCH$_2$}$_4$C (12) was 279 mg (71%), white solid. TLC: R$_f$ 0.42 (8:2:1 (v/v/v) acetone/methanol/water).

$^1$H NMR (500 MHz, [D$_6$]DMSO, 30° C.), mixture of conformers by two N-carboxymethyl-glycine units per chain, δ, ppm: 8.604, 8.519, 8.397, 8.388, 8.346, 8.211, 8.200, 8.167, 8.034, 8.024, 7.925, 7.912, 7.819 and 7.773 (t, 6H; 6 NHCO), 6.992 (t, J=5.9 Hz, 1H; NHCOO), 4.302-3.723 (18H; 2 NCH$_2$CO, 2 NCH$_2$COOCH$_3$, 5 COCH$_2$NH), 3.692, 3.689 and 3.632 (s, 6H; 2 OCH$_3$), 3.566 (d, J=5.9 Hz, 2H; COCH$_2$NHCOO), 2.686 (broad. d, 2H; C—CH$_2$NH), 1.380 (s, 9H; C(CH$_3$)$_3$).

The {Boc-[Gly$_2$(MCMGly)]$_2$Gly$_2$-NHCH$_2$}$_4$C (12) (269 mg, 91.65 μmol) was dissolved in CF$_3$COOH (2 ml) and the solution was kept for 40 min at room temperature. Trifluoroacetic acid was evaporated under vacuum, the residue extracted three times with (CH$_3$CH$_2$)$_2$O (slight agitation with 15 ml of (CH$_3$CH$_2$)$_2$O for 30 min followed by decantation) to remove residual CF$_3$COOH, and then dried under vacuum. The yield of {CF$_3$COOH.H-[Gly$_2$(MCMGly)]$_2$Gly$_2$-NHCH$_2$}$_4$C (13) was 270 mg (98%), white solid.

SCHEME III

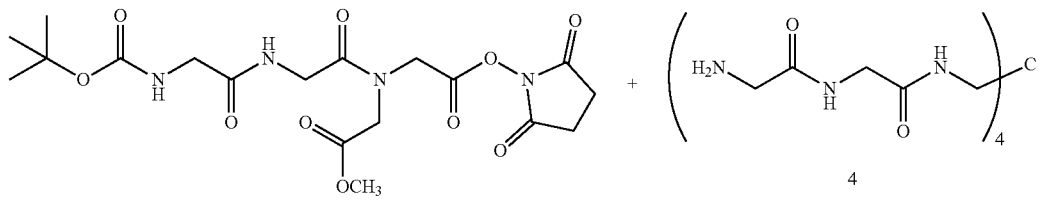

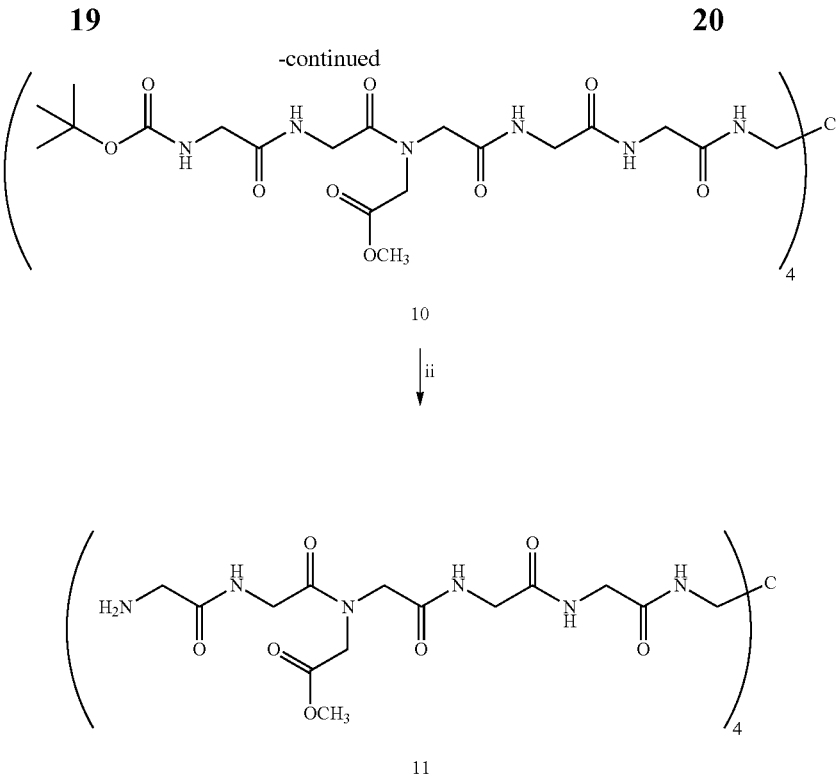

¹H NMR (500 MHz, [D₂]H₂O, 30° C.), mixture of conformers by two N-carboxymethyl-glycine units per chain, δ, ppm: 4.441-3.963 (singlets, 18H; 2 NC$\underline{H}_2$CO, 2 NC$\underline{H}_2$COOCH₃, 5 COC$\underline{H}_2$NH), 3.920 (s, 2H; COC$\underline{H}_2$NH₂⁺), 3.833, 3.824, 3.780 and 3.773 (s, 6H; 2 OC$\underline{H}_3$), 2.918 (s, 2H; C—C$\underline{H}_2$NH).

Preparation of {CF₃COOH.H-[Gly₂(MCMGly)]₃Gly-NHCH₂}₄C (15) (Steps iii and iv of Scheme IV)

To a stirred solution of (CF₃COOH H-[Gly₂(MCMGly)]₂Gly₂-HNCH₂)₄C (13) (175 mg, 58.5 μmol) in DMSO (2 ml) the ester 9 (0.351 mmol, 0.702 ml of 0.5 M solution in DMSO) and (CH₃CH₂)₃N (49 μL, 0.351 mmol) were added. The mixture was stirred overnight at room temperature, acidified with 30 μL AcOH and solvent removed under vacuum (freeze drying). The residue was dissolved in a minimal volume of a mixture of 1:1 (v/v) acetonitrile/water and fractionated on a Sephadex LH-20 column (eluted with 1:1 (v/v) acetonitrile/water). Selected fractions were evaporated and the residue was dried in vacuum. The yield of pure {Boc-[Gly₂ (MCMGly)]₃Gly₂-NHCH₂}₄C (14) was 279 mg (71%), white solid. TLC: R$_f$ 0.42 (8:2:1 (v/v/v) acetone/methanol/water). Fractions containing {Boc-[Gly₂(MCMGly)]₃Gly₂-NHCH₂}₄C (14) were combined, evaporated to c. 2 ml volume and freeze dried. The initial yield was 215 mg (94%). Additional purification on a silica gel column (packed in acetonitrile and eluted with 4:5:2 (v/v/v) i-PrOH/acetonitrile/water) resulted in 169 mg of Boc-[Gly₂(MCMGly)]₃Gly₂-NHCH₂)₄C (yield 74%, white solid). TLC: R$_f$ 0.45 (4:5:2 (v/v/v) i-PrOH/acetonitrile/water).

¹H NMR (500 MHz, [D₆]DMSO, 30° C.), mixture of conformers by three N-carboxymethyl-glycine units per chain, δ, ppm: 8.594-7.772 (triplets, together 8H; 8 N$\underline{H}$CO), 6.989 (t, J=5.6 Hz, 1H; N$\underline{H}$COO), 4.303-3.722 (26H; 3 NC$\underline{H}_2$CO, 3 NC$\underline{H}_2$COOCH₃, 7 COC$\underline{H}_2$NH), 3.692 and 3.632 (s, 9H; 3 OC$\underline{H}_3$), 3.565 (d, J=5.6 Hz, 2H; COC$\underline{H}_2$NHCOO), 2.687 (broad. d, 2H; C—C$\underline{H}_2$NH), 1.380 (s, 9H; C(CH₃)₃).

The {Boc-[Gly₂(MCMGly)]₃Gly₂-NHCH₂}₄C (146 mg, 37.36 μmol) (14) was dissolved in CF₃COOH (1 ml) and the solution was kept for 40 min at room temperature. Trifluoroacetic acid was evaporated under vacuum, the residue extracted three times with (CH₃CH₂)₂O (slight agitation with 10 ml of (CH₃CH₂)₂O for 30 min followed by decantation) to remove residual CF₃COOH, and then dried under vacuum. The yield of {CF₃COOH.H-[Gly₂(MCMGly)]₃Gly₂-NHCH₂}₄C (15) was 147 mg (99%), white solid.

¹H NMR (500 MHz, [D₂]H₂O, 30° C.), mixture of conformers by three N-carboxymethyl-glycine units per chain, δ, ppm: 4.446-3.964 (singlets, 26H; 3 NC$\underline{H}_2$CO, 3 NC$\underline{H}_2$COOCH₃, 7 COC$\underline{H}_2$NH), 3.924 (s, 2H; COC$\underline{H}_2$NH₂⁺), 3.836, 3.828, 3.824, 3.783, 3.778 and 3.773 (s, 9H; 3 OC$\underline{H}_3$), 2.919 (s, 2H; C—C$\underline{H}_2$NH).

Preparation of (CF₃COOH.H-[Gly₂(MCMGly)]₄Gly₂-NHCH₂)₄C (17) (Steps v and vi of Scheme IV)

To a stirred solution of (CF₃COOH.H-Gly₂(MCMGly)]₃-HNCH₂)₄C (15) (68 mg, 17.16 μmol) in DMSO (1 ml) the ester 9 (0.137 mmol, 0.275 ml of 0.5 M solution in DMSO) and (CH₃CH₂)₃N (14.3 μL, 0.103 mmol) were added. The mixture was stirred overnight at room temperature, acidified with 100 μL AcOH and solvent removed under vacuum (freeze drying). The residue was dissolved in a minimal volume of a mixture of 1:1 (v/v) acetonitrile/water (0.25% AcOH) and fractionated on a Sephadex LH-20 column (eluted with 1:1 (v/v) acetonitrile/water (0.25% AcOH)). Fractions containing {Boc-[Gly₂(MCMGly)]₄Gly₂-NHCH₂}₄C (16) were combined, evaporated to c. 2 ml volume and freeze dried. The yield was 81 mg (96%), white solid. TLC: R$_f$ 0.24 (4:5:2 (v/v/v) i-PrOH/acetonitrile/water).

SCHEME IV
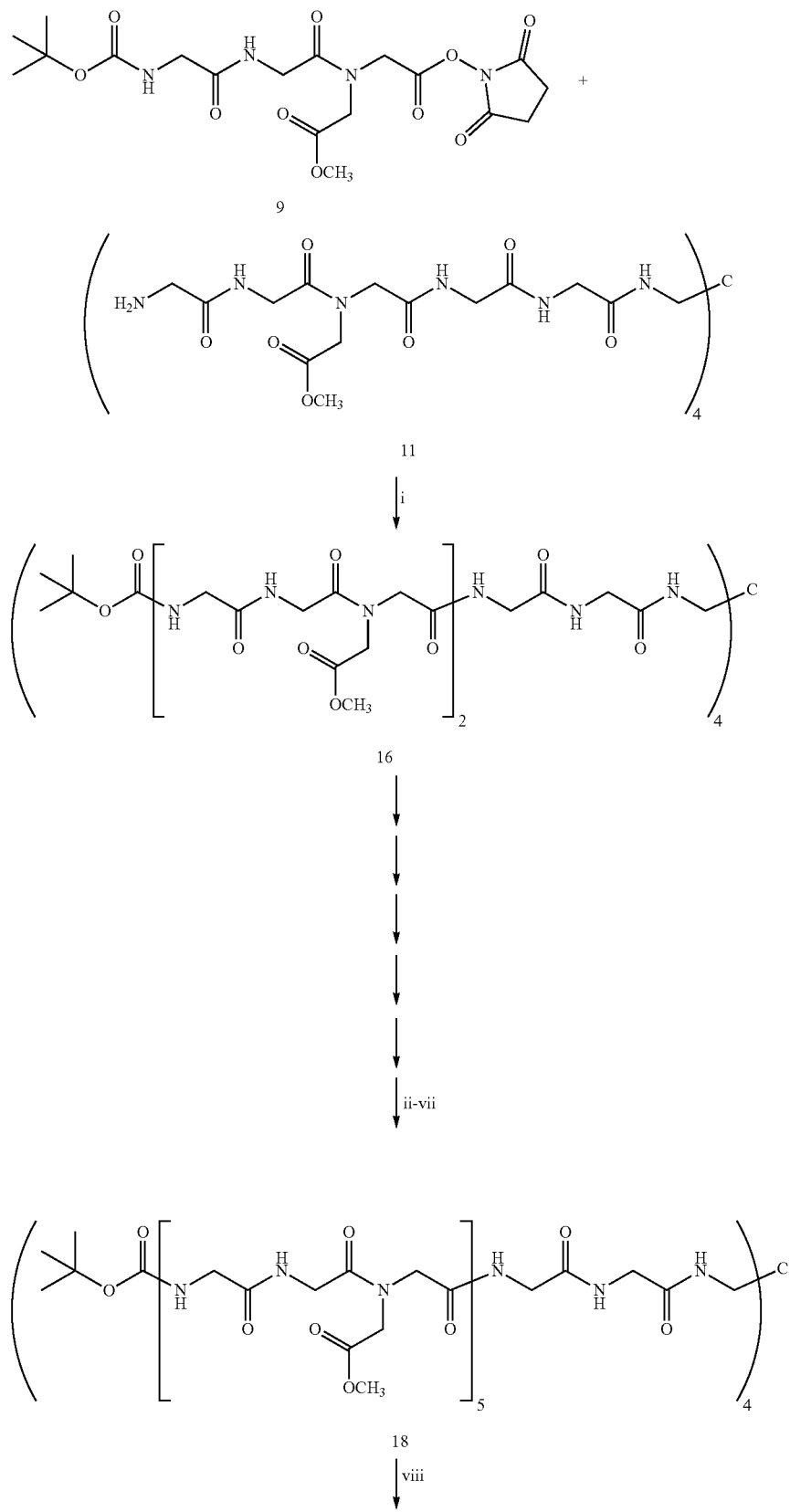

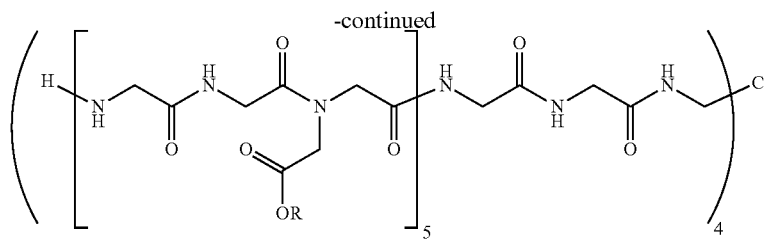

19 (R is CH₃); 20 (R is H)

¹H NMR (500 MHz, [D₆]DMSO, 30° C.), mixture of conformers by four N-carboxymethyl-glycine units per chain, δ, ppm: 8.590-7.773 (triplets, 10H; 10 NHCO), 6.989 (t, J=5.6 Hz, 1H; NHCOO), 4.303-3.722 (34H; 4 NCH₂CO, 4 NCH₂COOCH₃, 9 COCH₂NH), 3.691 and 3.631 (s, 12H; 4 OCH₃), 3.565 (d, J=5.6 Hz, 2H; COCH₂NHCOO), 2.684 (broad. d, 2H; C—CH₂NH), 1.379 (s, 9H; C(CH₃)₃).

The {Boc-[Gly₂(MCMGly)]₄Gly₂-NHCH₂}₄C (16) (74 mg, 15.16 μmol) was dissolved in CF₃COOH (1 ml) and the solution was kept for 40 min at room temperature. Trifluoroacetic acid was evaporated under vacuum, the residue extracted three times with (CH₃CH₂)₂O (slight agitation with 10 ml of (CH₃CH₂)₂O for 30 min followed by decantation) to remove residual CF₃COOH, and then dried under vacuum. The yield of {CF₃COOH.H-[Gly₂(MCMGly)]₄ Gly₂-NHCH₂}₄C (17) was 72 mg (96%), white solid.

¹H NMR (500 MHz, [D₂]H₂O, 30° C.), mixture of conformers by four N-carboxymethyl-glycine units per chain, δ, ppm: 4.446-3.964 (singlets, 34H; 4 NCH₂CO, 4 NCH₂COOCH₃, 9 COCH₂NH), 3.925 (s, 2H; COC H₂NH₂⁺), 3.836, 3.829, 3.827, 3.822, 3.783, 3.779, 3.777 and 3.772 (s, 12H; 4 OCH₃), 2.919 (s, 2H; C—CH₂NH).

Preparation of (CF₃COOH.H-[Gly₂(MCMGly)]₅ Gly₂-NHCH₂)₄C (19) (Steps vii and viii of Scheme IV)

To a stirred solution of (CF₃COOH H-Gly₂ (MCM Gly)]₄-HNCH₂)₄C (17) (16.8 mg, 3.403 μmol) in DMSO (1 ml) the ester 9 (27.2 μmol, 63 μl of 0.5 M solution in DMSO) and (CH₃CH₂)₃N (3 μl, 21.6 μmol) were added. The mixture was stirred overnight at room temperature, acidified with 100 μL AcOH and solvent removed under vacuum (freeze drying). The residue was dissolved in a minimal volume of a mixture of 1:1 (v/v) acetonitrile/water (0.25% AcOH) and fractionated on a Sephadex LH-20 column (eluted with 1:1 (v/v) acetonitrile/water (0.25% AcOH)). Fractions containing {Boc-[Gly₂(MCMGly)]Gly₂-NHCH₂}₄C (18) were combined, evaporated to c. 1 ml volume and freeze dried. The yield was 19 mg (95%), white solid. TLC: R$_f$ 0.15 (4:3:2 (v/v/v) i-PrOH/acetonitrile/water).

¹H NMR (500 MHz, [D₆]DMSO, 30° C.), mixture of conformers by five N-carboxymethyl-glycine units per chain, δ, ppm: 8.595-7.772 (triplets, 12H; 12 NHCO), 6.989 (t, J=5.6 Hz, 1H; NHCOO), 4.303-3.723 (42H; 5 NCH₂CO, 5 NCH₂COOCH₃, 11 COCH₂NH), 3.692 and 3.631 (s, 15H; 5 OCH₃), 3.565 (d, J=5.6 Hz, 2H; COCH₂NHCOO), 2.686 (broad. d, 2H; C—CH₂NH), 1.380 (s, 9H; C(CH₃)₃).

The {Boc-[Gly₂(MCMGly)]₅Gly₂-NHCH₂}₄C (18) (19 mg, 3.25 μmol) was dissolved in CF₃COOH (0.5 ml) and the solution was kept for 40 min at room temperature. Trifluoroacetic acid was evaporated under vacuum, the residue extracted three times with (CH₃CH₂)₂O (slight agitation with 5 ml of (CH₃CH₂)₂O for 30 min followed by decantation) to remove residual CF₃COOH, and then dried under vacuum. Yield of {CF₃COOH.H-[Gly₂(MCMGly)]₅Gly₂-NHCH₂}₄C (19) was 20 mg (99%), white solid.

¹H NMR (500 MHz, [D₂]H₂O, 30° C.), mixture of conformers by five N-carboxymethyl-glycine units per chain, δ, ppm: 4.446-3.965 (singlets, 42H; 5 NCH₂CO, 5 NCH₂COOCH₃, 11 COCH₂NH), 3.924 (s, 2H; COC H₂NH₂⁺), 3.835, 3.829, 3.827, 3.825, 3.823, 3.783, 3.779, 3.777 and 3.773 (s, 15H; 5 OCH₃), 2.919 (s, 2H; C—C H₂NH).

Preparation of [CF₃COOH.H-(Gly₂CMGly)₅Gly₂-NHCH₂]₄C, Et₃N-salt (20) (Scheme IV)

To a solution of product 19 (463 mg, 0.07835 mmol) in water (26 mL), Et₃N (523 μL, 3.761 mmol) was added and the solution kept for 18 h at r.t. After evaporation the residue was freeze-dried in vacuum. Yield of product 20 was 587 mg (98%), white solid. TLC: R$_f$ 0.39 (1:2:1 (v/v/v) CHCl₃/MeOH/water).

¹H NMR (600 MHz, [D₂]H₂O, 30° C.) δ, ppm: 4.309-3.919 (176H; 20 NCH₂CO, 20 NCH₂COOH, 48 COC H₂NH), 3.226 (q, 120H, J=7.3 Hz; 60 NCH₂CH₃), 2.964 (broad.s, 8H; 4 C—CH₂NH), 1.305 (t, 180H, J=7.3 Hz; 60 NCH₂CH₃).

MALDI TOF mass-spectrum, M/Z: 5174, M+H; 5196, M+Na.

Preparation of activated 1,2-O-dioleoyl-sn-glycero-3-phosphatidylethanolamine (DE-Ad-OSu) (23) (Step i of Scheme V)

To a solution of bis(N-hydroxysuccinimidyl) adipate (21) (70 mg, 205 μmol) in dry N,N-dimethylformamide (1.5 ml), 1,2-O-dioleoyl-sn-glycero-3-phosphatidylethanolamine (22) (40 μmol) in chloroform (1.5 ml) was added, followed by triethylamine (7 μl). The mixture was kept for 2 h at room temperature, then neutralized with acetic acid and partially concentrated under vacuum. Column chromatography (Sephadex LH-20, 1:1 chloroform-methanol, 0.2% acetic acid) of the residue yielded the product 23 (37 mg, 95%) as a colorless syrup.

¹H NMR (CDCl₃/CD₃OD, 2:1) 5.5 (m, 4H, 2×(—CH═C H—), 5.39 (m, 1H, —OCH₂—CHO—CH₂O—), 4.58 (dd, 1H, J=3.67, J=11.98, —CCOOHCH—CHO—CH₂O—), 4.34 (dd, 1H, J=6.61, J=11.98, —CCOO HCH—CHO—CH₂O—), 4.26 (m, 2H, PO—C H₂—CH₂—NH₂), 4.18 (m, 2H, —CH₂—OP), 3.62 (m, 2H, PO—CH₂—CH₂—NH₂), 3.00 (s, 4H, ONSuc), 2.8 (m, 2H, —CH₂—CO (Ad), 2.50 (m, 4H, 2×(—CH₂—CO), 2.42 (m, 2H, —CH₂—CO (Ad), 2.17 (m, 8H, 2×(—C H₂—CH═CH—CH₂—), 1.93 (m, 4H, COCH₂CH₂C H₂CH₂CO), 1.78 (m, 4H, 2×(COCH₂CH₂—), 1.43, 1.47 (2 bs, 40H, 20 CH₂), 1.04 (m, 6H, 2CH₃). R$_f$ 0.5 (chloroform-methanol-water, 6:3:0.5.

Preparation of [H-(Gly₂CMGly)₅Gly₂-NHCH₂]₃ [DE-CO(CH₂)₄CO-(Gly₂CMGly)₅Gly₂-NHCH₂]C, Na, Et₃N-salt (24) (Step ii of Scheme V)

To a stirred solution of product 20 (522 mg, 0.06821 mmol) in water/2-propanol mixture (16 mL, 2:3) 1M NaHCO₃ (547 μL, 0.547 mmol) and a solution of DE-Ad-OSu (23) (66.1 mg, 0.06821 mmol) in dichloroethane (368 μL) were added, and the solution was stirred for 1.5 h at r.t. After acidification with AcOH (94 μL) the solution was evaporated and the residue was dried in vacuum. Dried mixture was dissolved in 3 mL of water/MeOH (15:1) and put on a C18 reverse phase column (~45 mL of phase washed with 75% MeOH and then with water/MeOH 15:1). Substances were eluted sequentially with water/MeOH (15: 1-50 mL; 9:1-50 mL; 7.5:2.5-50 mL; 1:1-50 mL; 2.5:7.5-100 mL). Unreacted 20 was eluted with water/MeOH 15:1 (Na salt by NMR data, 116 mg, 30.8% of recovery) and with water/MeOH 9:1 (Et₃N salt by NMR data, 63 mg, 13.6% of recovery). Target (H-CMG₅)₃C(CMG₅-Ad-DE) (24) was eluted with water/MeOH 1:1. Yield of pure freeze-dried product 24 was 135 mg (25.5% on (24)), white solid. TLC (1:2:1 (v/v/v) MeOH/ethyl acetate/water): 20 $R_f$ 0.06; 24 $R_f$ 0.17.

(H-CMG₅)₃C(CMG₅-Ad-DE) Na₁(Et₃N)₂₀(24): ¹H NMR (700 MHz, [D₂]H₂O/[D₄]CH₃OH 2:1 (v/v), 30° C.) δ, ppm: 5.561 (m, 4H; 2 cis C$\underline{H}$=C$\underline{H}$ of DE), 5.454 (m, 1H; OC$\underline{H}_2$—CH(OCO)CH₂O of DE), 4.629 (dd, 1H, J=12.3 Hz/2 Hz; OCH₂—CH(OCO)C$\underline{H}$OCO of DE), 4.462-4.057 (181H; 20 NC$\underline{H}_2$CO, 20 NC$\underline{H}_2$COOH, 48 COC$\underline{H}_2$NH, OC$\underline{H}_2$—CH(OCO)C$\underline{H}$OCO of DE, OC$\underline{H}_2$CH₂NH of DE), 3.597 (t, 2H, J=5 Hz; OCH₂C$\underline{H}_2$NH of DE), 3.226 (q, 102H, J=7.3 Hz; 51 NC$\underline{H}_2$CH₃), 3.099 (broad.s, 8H; 4 C—C$\underline{H}_2$NH), 2.557, 2.532, 2.522 and 2.456 (triplets, total 8H; 4 CO—C$\underline{H}_2$CH₂), 2.203 (~dd, 8H, J=12 Hz/5.8 Hz; 2 C$\underline{H}_2$—CH=CH—C$\underline{H}_2$ of DE), 1.807 and 1.783 (multiplets, 8H; 4 CO—CH₂C$\underline{H}_2$), 1.526 and 1.475 (overlapping m and t, total 193H; m, 20 CH₂ of DE; t, J=7.3 Hz, 51 NCH₂C$\underline{H}_3$), 1.063 (t, 6H, J=7 Hz; 2 CH₃ of DE).

MALDI TOF mass-spectrum, M/Z: 6028, M+H; 6050, M+Na.

Preparation of 3-trifluoroacetamidopropyl-3,4-di-O-acetyl-2,6-di-O-benzyl-α-D-galactopyranosyl-(1→3)-2,4-di-O-acetyl-6-O-benzyl-β-D-galactopyranosyl-(1→4)-2-acetamido-3-O-acetyl-6-O-benzyl-2-deoxy-β-D-glucopyranoside (27) (Step i of Scheme VI)

The glycosyl acceptor (3-trifluoroacetamidopropyl)-2-acetamido-3-O-acetyl-6-O-benzyl-2-deoxy-4-O-(2,4-di-O-acetyl-6-O-benzyl-β-D-galactopyranosyl)-β-D-glucopyranoside (25) was prepared according to the method disclosed in the publication of Pazynina et al (2008). A mixture of the glycosyl acceptor 25 (500 mg, 0.59 mmol), thiogalactopyranoside 26 (576 mg, 1.18 mmol), NIS (267 mg, 1.18 mmol), anhydrous CH₂Cl₂ (25 ml) and molecular sieves 4 Å (500 mg) was stirred at −45° C. for 30 min under an atmosphere of Ar. A solution of TfOH (21 μl, 0.236 mmol) in anhydrous CH₂Cl₂ (0.5 ml) was then added. The reaction mixture was stirred for 2 h at −45° C. and the temperature was then increased to −20° C. over 4 h. The mixture was kept at −20° C. overnight. Then extra amounts of thiogalactopyranoside 26 (144 mg, 0.295 mmol), NIS (66 mg, 0.295 mmol) and TfOH (5 μl, 0.06 mmol) were added and the stirring maintained at −20° C. for 2 h before being allowed to slowly warm up to r.t. (1 h). A saturated aqueous solution of Na₂S₂O₃ was then added and the mixture filtered. The filtrate was diluted with CHCl₃ (300 ml), washed with H₂O (2×100 ml), dried by filtration through cotton wool, and concentrated. Gel filtration on LH-20 (CHCl₃-MeOH) afforded the product 27 (600 mg, 80%), as a white foam.

¹H NMR (700 MHz, CDCl₃, characteristic signals), δ, ppm: 1.78-1.82 (m, 4H, CHCHC, OC(O)CH₃), 1.84-1.90 (m, 1H, CHCHC), 1.91, 1.94, 1.97, 1.98, 2.06 (5 s, 5×3H, 4 OC(O)CH₃, NH(O)CH₃), 3.23-3.30 (m, 1H, NCHH), 3.59-3.65 (m, 1H, NCHH), 4.05 (m, 1H, H-2$^I$), 4.33 (d, 1H, $J_{1,2}$ 7.55, H-1$^I$), 4.40 (d, 1H, J 12.04, PhCHH), 4.42 (d, 1H, $J_{1,2}$ 8.07, H-1$^{II}$), 4.45 (d, 1H, J 11.92, PhCHH), 4.48 (d, 1H, J 12.00, PhCHH), 4.50 (d, 1H, J 12.00, PhCHH), 4.52 (d, 1H, J 12.04, PhCHH), 4.54 (d, 1H, J 12.00, PhCHH), 4.57 (d, 1H, J 12.00, PhCHH), 4.64 (d, 1H, J 11.92, PhCHH), 4.99 (dd~t, 1H, J 8.24, H-2$^{II}$), 5.08-5.13 (m, 2H, H-3$^I$, H-3$^{III}$), 5.23 (d, 1H, $J_{1,2}$ 3.31, H-1$^{III}$), 5.46 (d, 1H, $J_{3,4}$ 2.25, H-4$^{II}$), 5.54 (d, 1H, $J_{3,4}$ 3.11, H-4$^{III}$), 7.20-7.40 (m, 20H, ArH); 7.49-7.54 (m, 1H, NHC(O)CF₃). $R_f$ 0.4 (PhCH₃—AcOEt, 1:2).

Preparation of 3-aminopropyl-α-D-galactopyranosyl-(1→3)-β-D-galactopyranosyl-(1→4)-2-acetamido-2-deoxy-β-D-glucopyranoside (29) (Steps ii and iii of Scheme VI)

The product 27 (252 mg, 0.198 mmol) was deacetylated according to Zemplen (8 h, 40° C.), neutralized with AcOH and concentrated. The TLC (CH₃Cl-MeOH, 10:1) analysis of the obtained product showed two spots: the main spot with $R_f$ 0.45, and another one on the start line (ninhydrin positive spot) that was an indication of partial loss of trifluoroacetyl. Therefore, the product was N-trifluoroacetylated by treatment with CF₃COOMe (0.1 ml) and Et₃N (0.01 ml) in MeOH (10 ml) for 1 h, concentrated and subjected to column chromatography on silica gel (CHCl₃-MeOH, 15:1) to afford the product 28 as a white foam (163 mg, 77%), $R_f$ 0.45 (CH₃Cl-MeOH, 10:1). The product 28 was subjected to hydrogenolysis (200 mg Pd/C, 10 ml MeOH, 2 h), filtered, N-defluoroacetylated (5% Et₃N/H₂O, 3 h) and concentrated. Cation-exchange chromatography on Dowex 50X4-400 (H⁺) (elution with 5% aqueous ammonia) gave the product 29 (90 mg, 98%) as a white foam.

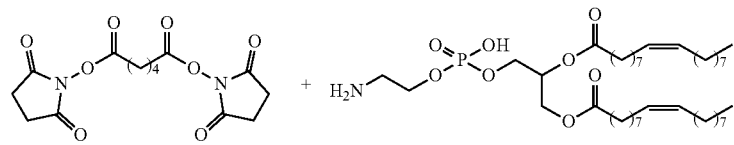

21    22

↓i

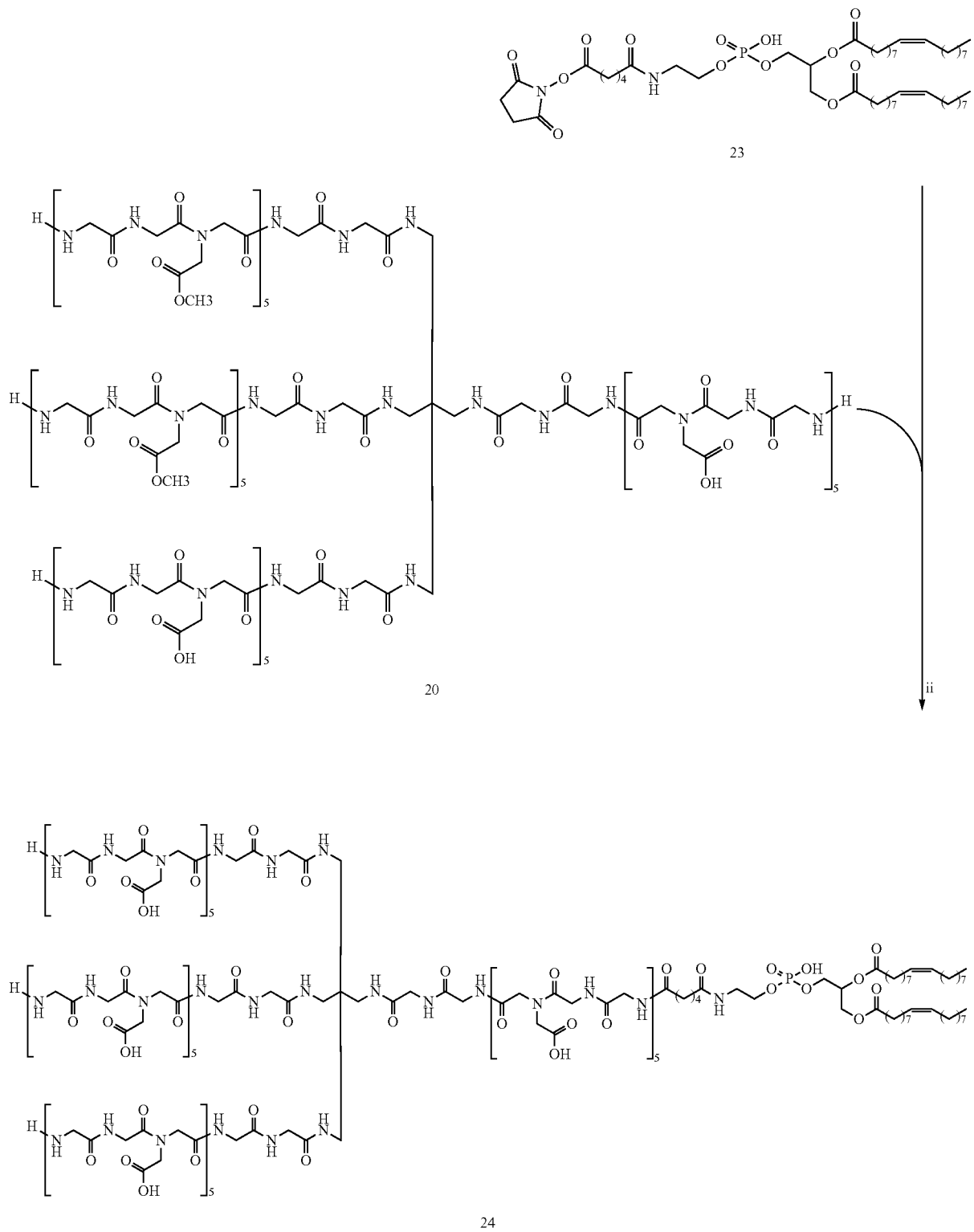

SCHEME VI

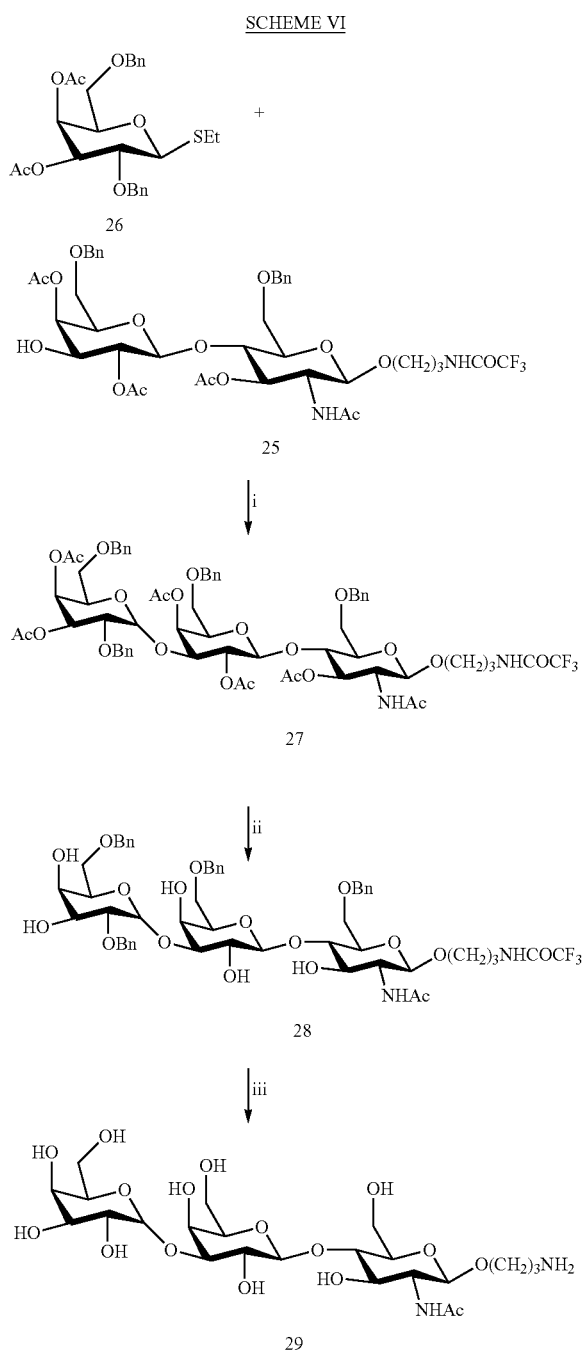

$^1$H NMR (D$_2$O, characteristic signals), δ, ppm: 1.94-1.98 (m, 2H, CCH$_2$C), 2.07 (s, 3H, NHC(O)CH$_3$), 3.11 (m, J 6.92, 2H, NCH$_2$), 4.54 and 4.56 (2d, 2H, J$_{1,2}$ 8.06, J$_{1,2}$ 7.87, H-1$^I$ and H-1$^{II}$), 5.16 (d, 1H, J$_{1,2}$ 3.87, H-1$^{III}$). R$_f$ 0.3 (EtOH-BuOH-Py-H$_2$O—AcOH; 100:10:10:10:3).

Preparation of 3-aminopropyl 2-acetamido-2-deoxy-α-D-galactopyranosyl-(1→3)-β-D-galactopyranosyl-(1→4)-2-acetamido-2-deoxy-β-D-glucopyranoside (33) (Steps i to iii of Scheme VII)

The glycosyl chloride 3,4,6-tri-O-acetyl-2-azido-2-desoxy-β-D-galactopyranosylchloride (30) was prepared according to the method disclosed in the publication of Paulsen et al (1978). A solution of the glycosyl acceptor 25 (420 mg, 0.5 mmol), silver triflate (257 mg, 1.0 mmol), tetramethylurea (120 μl, 1.0 mmol) and freshly calcinated molecular sieves 4 Å in dry dichloromethane (20 ml), were stirred at room temperature in darkness for 30 min. Another portion of sieves 4 Å was added, and a solution of glycosyl chloride 30 (350 mg, 1.0 mmol) in dry dichloromethane (3 ml) was added. The mixture was stirred for 20 h at room temperature. The resin was filtered and washed with methanol (4×10 ml), then solvent was evaporated. Chromatography on silica gel (elution with 5-7% isopropanol in chloroform) yielded 407 mg (70%) of the product 31 as a mixture of anomers (α/β=3.0 as determined by $^1$H-NMR spectroscopy).

A solution of the product 31 (407 mg, 0.352 mmol) in methanol (30 ml) was subjected to hydrogenolysis over 400 mg 10% Pd/C for 16 h. Then the resin was filtered off, washed with methanol (4×10 ml) and the product concentrated in vacuum. The dry residue was acetylated with 2:1 pyridine-acetic anhydride mixture (6 ml) at 20° C. for 16 h, the reagents being co-evaporated with toluene. Two chromatography steps on silica gel (elution with 10% isopropanol in ethyl acetate and with 5-10% methanol in chloroform) resulted in 160 mg (42%) of the product 32 and 39 mg (10%) of the product 32β.

A solution of 2 M sodium methylate in methanol (200 μl) was added to a solution of the product 32 (160 mg, 0.149 mmol) in dry methanol (4 ml). The solution was evaporated after 1 h, 4 ml water added and the solution kept for 16 h before being chromatographed on a Dowex-H$^+$ column (elution with 1 M ammonia). The eluate was evaporated, lyophilized to yield 87.2 mg (91%) of the 3-aminopropyl-trisaccharide (33).

$^1$H NMR spectra were recorded on a Bruker BioSpin nGbH spectrometer at 303K. Chemical shifts (δ) for characteristic protons are provided in ppm with the use of HOD (4.750), CHCl$_3$ (δ 7.270) as reference. Coupling constants (J) are provide in Hz. The signals in $^1$H NMR spectra were assigned using a technique of spin-spin decoupling (double resonance) and 2D-$^1$H,$^1$H-COSY experiments.

The values of optical rotation were measured on a digital polarimeter Perkin Elmer 341 at 25° C.

Mass spectra were registered on a MALDI-TOF Vision-2000 spectrometer using dihydroxybenzoic acid as a matrix.

32: $^1$H-NMR (700 MHz, CDCl$_3$): 1.759-1.834 (m, 1H, CH sp); 1.853-1.927 (m, 1H, CH sp); 1.972, 1.986, 1.996, 2.046, 2.053, 2.087, 2.106, 2.115, 2.130, 2.224 (10s, 10×3H, COCH$_3$); 3.222-3.276 (m, 1H, NCH sp); 3.544-3.583 (m, 1H, OCH sp); 3.591-3.661 (m, 2H, NCH sp, H-5a); 3.764 (dd≈t, 1H, H-4a, J 8.8); 3.787 (dd, 1H, H-3b, J$_{3,4}$ 3.7, J$_{2,3}$ 9.9); 3.836 (br. t, 1H, H-5b, J 7.3); 3.882-3.920 (m, 1H, OCH sp); 3.950 (dd, 1H, H-6'c, J$_{6',6''}$ 10.6, J$_{5,6'}$ 5.2); 4.009 (ddd, 1H, H-2a, J$_{1,2}$ 7.9, J$_{2,3}$ 10.0, J$_{2,NH}$ 9.0); 4.076-4.188 (m, 5H, H-6'a, H-6'b, H-6''b, H-5c, H-6''c); 4.415 (d, 1H, H-1a, J$_{1,2}$ 7.9); 4.443 (d, 1H, H-1b, J$_{1,2}$ 7.9); 4.529 (dd, 1H, H-6''a, J$_{6',6''}$ 12.0, J$_{5,6'}$ 2.5); 4.548 (ddd, 1H, H-2c, J$_{1,2}$ 3.4, J$_{2,3}$ 11.6, J$_{2,NH}$ 9.4); 4.893 (dd, 1H, H-3c, J$_{3,4}$ 3.1, J$_{2,3}$ 11.6); 5.021 (d, 1H, H-1c, J$_{1,2}$ 3.4); 5.039-5.075 (m, 2H, H-3a, H-2b); 5.339 (dd≈d, 1H, H-4b, J 2.9); 5.359 (dd, 1H, H-4c, J$_{3,4}$ 2.7, J$_{4,5}$ 0.9); 5.810 (d, 1H, NHAc a, J$_{2,NH}$ 9.0); 6.184 (d, 1H, NHAc c, J$_{2,NH}$ 9.4); 7.310-7.413 (m, 1H, NHCOCF$_3$ sp). R$_f$ 0.31 (EtOAc-iPrOH, 10:1). MS, m/z calculated for [C$_{43}$H$_{60}$N$_3$F$_3$O$_{25}$]H$^+$: 1076.35, found 1076.

32β: $^1$H-NMR (700 MHz, CDCl$_3$): 1.766-1.832 (m, 1H, CH sp); 1.850-1.908 (m, 1H, CH sp); 1.923, 1.969, 1.982, 2.059, 2.071, 2.099 (2), 2.120, 2.136, 2.148 (10s, 10×3H, COCH$_3$); 3.230-3.289 (m, 1H, NCH sp); 3.521 (ddd, 1H, H-2c, J$_{1,2}$ 8.2, J$_{2,3}$ 11.2, J$_{2,NH}$ 7.8); 3.548-3.591 (m, 1H, OCH sp); 3.591-3.648 (m, 2H, NCH sp, H-5a); 3.743 (dd≈t, 1H, H-4a, J 8.6); 3.795 (br. t, 1H, H-5b, J 6.5); 3.852 (dd, 1H, H-3b, J$_{3,4}$ 3.6, J$_{2,3}$ 9.9); 3.873-3.923 (m, 2H, H-5c, OCH sp); 4.002 (ddd, 1H, H-2a, J$_{1,2}$ 8.0, J$_{2,3}$ 9.5, J$_{2,NH}$ 8.9); 4.039 (dd, 1H, H-6'b, J$_{6',6''}$ 11.6, J$_{5,6'}$ 6.9); 4.087-4.144 (m, 3H, H-6'a, H-6''b, H-6'c); 4.160 (dd, 1H, H-6''c, J$_{6',6''}$ 11.2, J$_{5,6''}$ 6.0);

4.409, 4.417 (2d≈t, 2×1H, H-1a, H-1b, J 7.6); 4.519 (dd, 1H, H-6"a, $J_{6',6''}$ 11.8, $J_{5,6''}$ 2.5); 4.992 (d, 1H, H-1c, $J_{1,2}$ 8.2); 5.043 (dd, 1H, H-3a, $J_{3,4}$ 8.6, $J_{2,3}$ 9.5); 5.066 (dd, 1H, H-2b, $J_{1,2}$ 8.0, $J_{2,3}$ 9.8); 5.350 (dd≈d, 1H, H-4c, J 3.2); 5.372 (dd≈d, 1H, H-4b, J 3.4); 5.399 (d, 1H, NHAc c, $J_{2,NH}$ 7.8); 5.449 (dd, 1H, H-3c, $J_{3,4}$ 3.4, $J_{2,3}$ 11.3); 5.856 (d, 1H, NHAc a, $J_{2,NH}$ 8.9); 7.361-7.466 (m, 1H, NHCOCF$_3$ sp). $R_f$ 0.24 (EtOAc-iPrOH, 10:1). MS, m/z calculated for $[C_{43}H_{60}N_3F_3O_{25}]H^+$: 1076.35, found 1076.

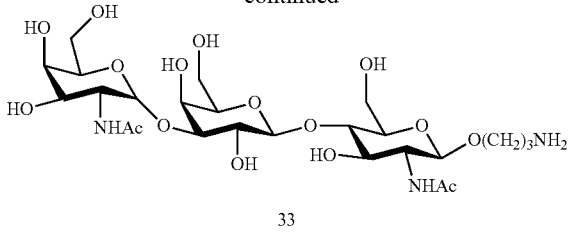

33: $^1$H-NMR (700 MHz, D$_2$O): 1.924-2.002 (m, 2H, CH$_2$ sp); 2.060, 2.064 (2s, 2×3H, NCOCH$_3$); 3.102 (m≈t, 2H, NCH$_2$ sp, J 6.8); 3.592-3.644 (m, 1H, H-5a); 3.655 (dd, 1H, H-2b, $J_{1,2}$ 7.9, $J_{2,3}$ 9.9); 3.702 (br. dd, 1H, H-5b, $J_{5,6'}$ 3.8, $J_{5,6''}$ 8.2, $J_{4,5}$≤1); 3.713-3.815 (m, 9H); 3.846 (dd, 1H, H-6'a, $J_{6',6''}$ 12.3, $J_{5,6'}$ 5.3); 3.984-4.062 (m, 4H, OCH sp, H-6"a, H-4b, H-3c); 4.123 (dd≈d, 1H, H-4c, J 2.9); 4.206 (br. t, 1H, H-5c, J 6.3); 4.248 (dd, 1H, H-2c, $J_{1,2}$ 3.6, $J_{2,3}$ 11.0); 4.542 (2d≈t, 2H, H-1a, H-1b, J 7.4); 5.100 (d, 1H, H-1c, $J_{1,2}$ 3.5). $R_f$ 0.55 (MeOH-1M aq. Py.AcOH, 5:1). MS, m/z calculated for $[C_{25}H_{45}N_3O_{16}]H^+$: 644.28; found 644. $[\alpha]_{546\ nm}$ +128 (c 0.3; MeCN—H$_2$O, 1:1).

33β: 1H-NMR (700 MHz, D$_2$O): 1.938-1.991 (m, 2H, CH$_2$ sp); 2.055, 2.062 (2s, 2×3H, NCOCH$_3$); 3.100 (m≈t, 2H, NCH$_2$ sp, J 6.9); 3.610 (dd, 1H, H-2b, $J_{1,2}$ 7.9, $J_{2,3}$ 9.9); 3.603-3.636 (m, 1H, H-5a); 3.682 (br. dd, 1H, H-5b, $J_{5,6'}$ 4.9, $J_{5,6''}$ 7.8, $J_{4,5}$≤1); 3.693-3.826 (m, 11H); 3.842 (dd, 1H, H-6'a, $J_{6',6''}$ 12.1, $J_{5,6'}$ 5.2); 3.934-3.972 (m, 2H, H-4b, H-2c); 4.012 (dd, 1H, H-6"a, $J_{6',6''}$ 12.2, $J_{5,6''}$ 2.0); 4.023-4.057 (m, 1H, OCH sp); 4.175 (dd≈d, 1H, H-4c, J 2.9); 4.478 (d, 1H, H-1b, $J_{1,2}$ 7.9); 4.531 (d, 1H, H-1a, $J_{1,2}$ 8.1); 4.638 (d, 1H, H-1c, $J_{1,2}$ 8.4). $R_f$ 0.48 (MeOH-1M aq. Py.AcOH, 5:1). MS, m/z calculated for $[C_{25}H_{45}N_3O_{16}]H^+$: 644.28; found 644. $[\alpha]_{546\ nm}$ +6 (c 0.3; MeCN—H$_2$O, 1:1).

Preparation of Galili-T-17-DE (35) (Step ii of Scheme VIII)

Compound 24 (4.3 mg, 5 μmol) and Et$_3$N (0.5 μl) in H$_2$O (0.75 ml) was added to a stirred solution of compound 34 (5 mg, 6 μmol) in dry DMSO (0.3 mL) in 3 portions during 1.5 h. The mixture was stirred for 24 h at room temperature and then subjected to column chromatography (Sephadex LH-20, MeOH—H$_2$O, 3:7) to yield the crude product 35. The product was lyophilized from water, the residue was dissolved in 3 ml of water, aqueous solution of NaHCO$_3$ (10 mM) was added to pH 6.5 and the solution was lyophilized to provide 3.7 mg of the compound 35 as Na-salt.

$^1$H NMR (700 MHz, D$_2$O/CD$_3$OD, 2:1 (v/v), selected chemical shifts) δ, ppm: 1.06 (t, J 7.03 Hz, C$\underline{H}_3$ of DE), 1.28-1.61 (m, C$\underline{H}_2$ of DE), 1.71-1.88 (m, —COCH$_2$CH$_2$CH$_2$CH$_2$CO and —COCH$_2$C$\underline{H}_2$—), 1.90-1.99 (m, OCH$_2$C$\underline{H}_2$CH$_2$N), 2.13-2.27 (m, —C$\underline{H}_2$CH=CHC$\underline{H}_2$—, NHC(O)C$\underline{H}_3$), 2.35-2.58 (m, COCH$_2$C$\underline{H}_2$CH$_2$CH$_2$CO— and —COCH$_2$C$\underline{H}_2$—), 2.93-3.24 (broad.s, 8H; 4 C—C$\underline{H}_2$NH), 4.63 (dd, J 2.49, J 12.32, C(O)OC$\underline{H}$HCHOCH$_2$O—), 4.67 and 4.70 (2d, $J_{1,2}$ 7.81, $J_{1,2}$ 7.95, H-1$^I$, H-1$^{II}$), 5.30 (d, $J_{1,2}$ 3.92, H-1$^{III}$), 5.42-5.47 (m, —OCH$_2$—C$\underline{H}$O—CH$_2$O—), 5.52-5.58 (m, 4H, 2×—C$\underline{H}$=C$\underline{H}$—). MALDI TOF mass-spectrum, M/Z: 8188 (M+Na); 8204 (M+K); 8226 (MNa+ K).

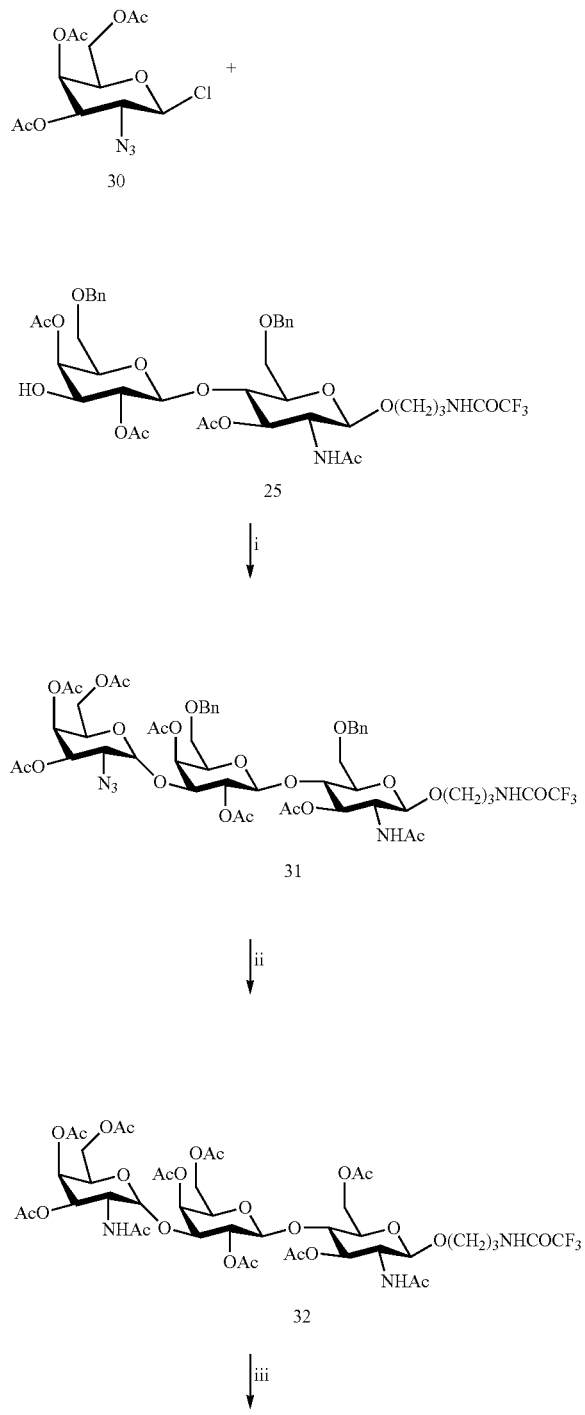

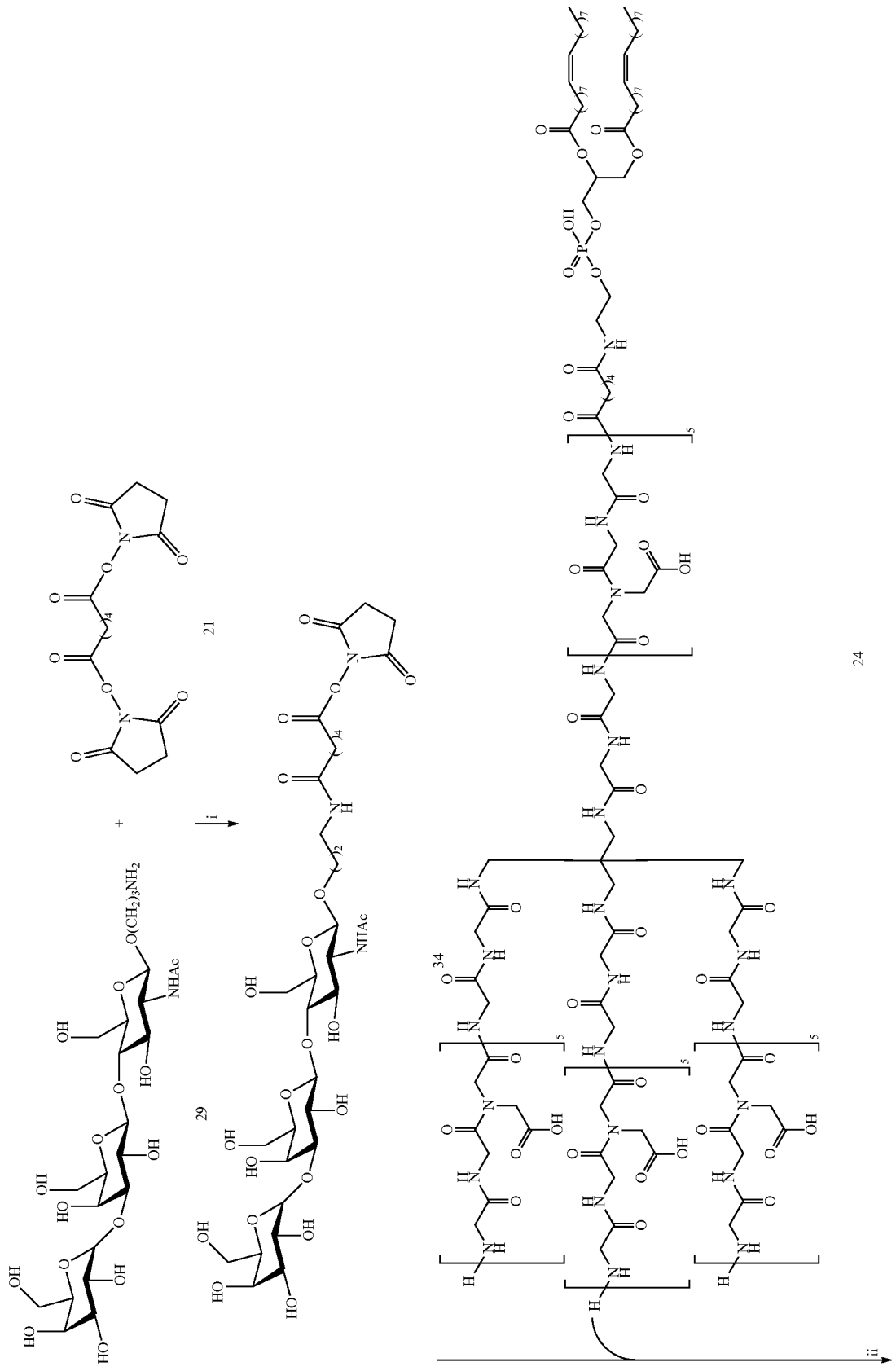

-continued
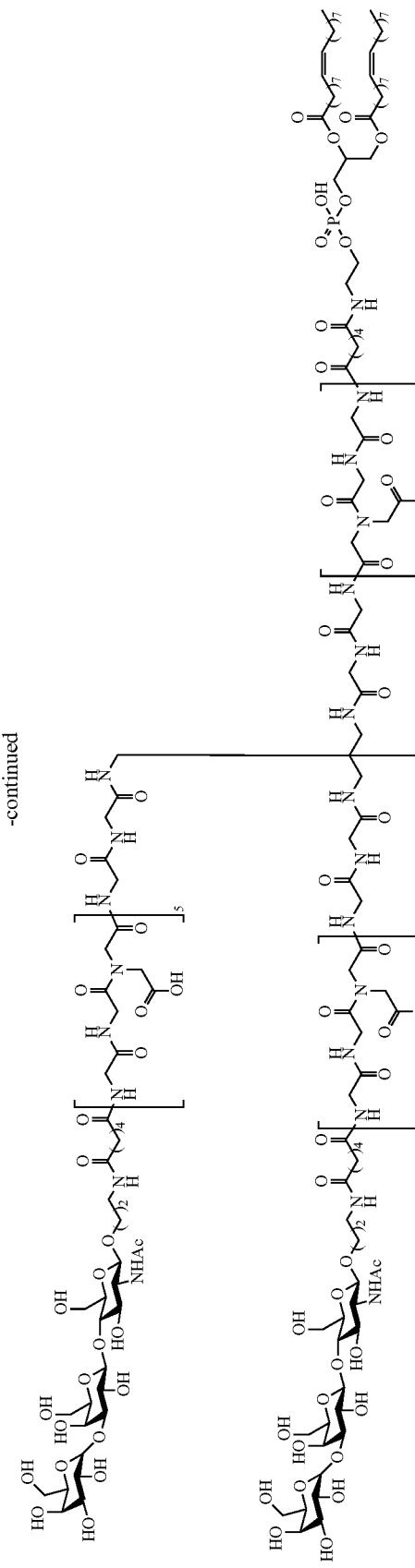

Preparation of (Mal-βAla-(Gly₂CMGly)₅Gly₂-NHCH₂)₃[DE-CO(CH₂)₄CO-(Gly₂CMGly)₅Gly₂-NHCH₂]C (37) (Scheme IX)

A solution of N-maleoyl-β-alanine N'-hydroxysuccinimide ester (36) (5.3 mg, 20 μmol) in MeCN (500 μL) is added in a single portion to a solution of 25.3 mg (3.3 μmol) of compound 24 in 4 mL of 25% aqueous isopropyl alcohol (IPA). The pH of the reaction mixture is adjusted to 7 to 8 with addition of NMM (1:10 (v/v) in IPA, circa 20 μL). The clear solution is kept overnight at room temperature, and the reaction endpoint checked by qualitative spot ninhydrin test. (A negative result in the test indicates the amino component has been consumed). The solvents are removed in vacuum using a rotary evaporator, the oily residue triturated with MeCN (500 μL) and the mixture sonicated for 10 minutes. The slurry obtained is transferred into an Eppendorf tube and centrifuged. The solid is washed repeatedly with absolute ether and MeCN (3×400 μL) with sonication followed by centrifugation until no starting reagent (Mal-βAla-ONSu) is detected by TLC (CHCl₃-MeOh—AcOH, 90:8:2 v/v). The precipitate after final ether wash is dried to constant weight in vacuum over 4 Å molecular sieves. A quantity of 18.9 mg (70%) of (Mal-βAla-CMG3-NHCH₂)₃CCH₂NH-CMG3-Ad-DOPE (37) was obtained as an amorphous white powder. The isolated substance may contain circa 17 moles of tertiary amines and a mole of sodium ion (Na) per mole of 37.

$R_f$ 0.4-0.5, (CHCl₃-MeOH—H₂O, 1:3:1 (v/v/v) plus 0.5% pyridine).

¹H NMR (700 MHz, [D₂]H₂O/[D₄]CH₃OH 1:1 (v/v), 30° C.) of Na/Et₃N salt (~7.3 M/M Et₃N) δ, ppm: 7.038 (s, 6H; 3 CH=CH), 5.542 (m, 4H; 2 cis C$\underline{H}$=C$\underline{H}$ of DE), 5.446 (m, 1H; OCH₂—C$\underline{H}$(OCO)CH₂O of DE), 4.635 (dd, 1H, J=12.2 Hz/2.3 Hz; OCH₂—CH(OCO)C$\underline{H}$OCO of DE), 4.516-4.041 (181H; 20 NC$\underline{H}$₂CO, 20 NC$\underline{H}$₂COOH, 48 COC$\underline{H}$₂NH, OC$\underline{H}$₂—CH(OCO)C$\underline{H}$HOCO of DE, OC$\underline{H}$₂CH₂NH of DE), 3.985 (t, J=6.8 Hz, 6H; 3 NCH₂ of Ala), 3.594 (t, 2H, J=4.5 Hz; OCH₂C$\underline{H}$₂NH of DE), 3.384 (q, 44H, J=7.3 Hz; 22 NC$\underline{H}$₂CH₃), 3.079 (broad.s, 8H; 4 C—C$\underline{H}$₂NH), 2.777 (t, 6H, J=6.8 Hz; 3 CH₂CO of Ala), 2.548, 2.522, 2.515 and 2.449 (triplets, total 8H; 4 CO—C$\underline{H}$₂CH₂), 2.195 (~dd, 8H, J=11.5 Hz/5.8 Hz; 2 C$\underline{H}$₂—CH=CH—C$\underline{H}$₂ of DE), 1.812 and 1.776 (multiplets, 8H; 4 CO—CH₂C$\underline{H}$₂), 1.484 and 1.454 (overlapping t and m, total 106H; t, J=7.3 Hz, 22 NCH₂C$\underline{H}$₃; m, 20 CH₂ of DE), 1.061 (t, 6H, J=7.1 Hz; 2 CH₃ of DE).

SCHEME IX
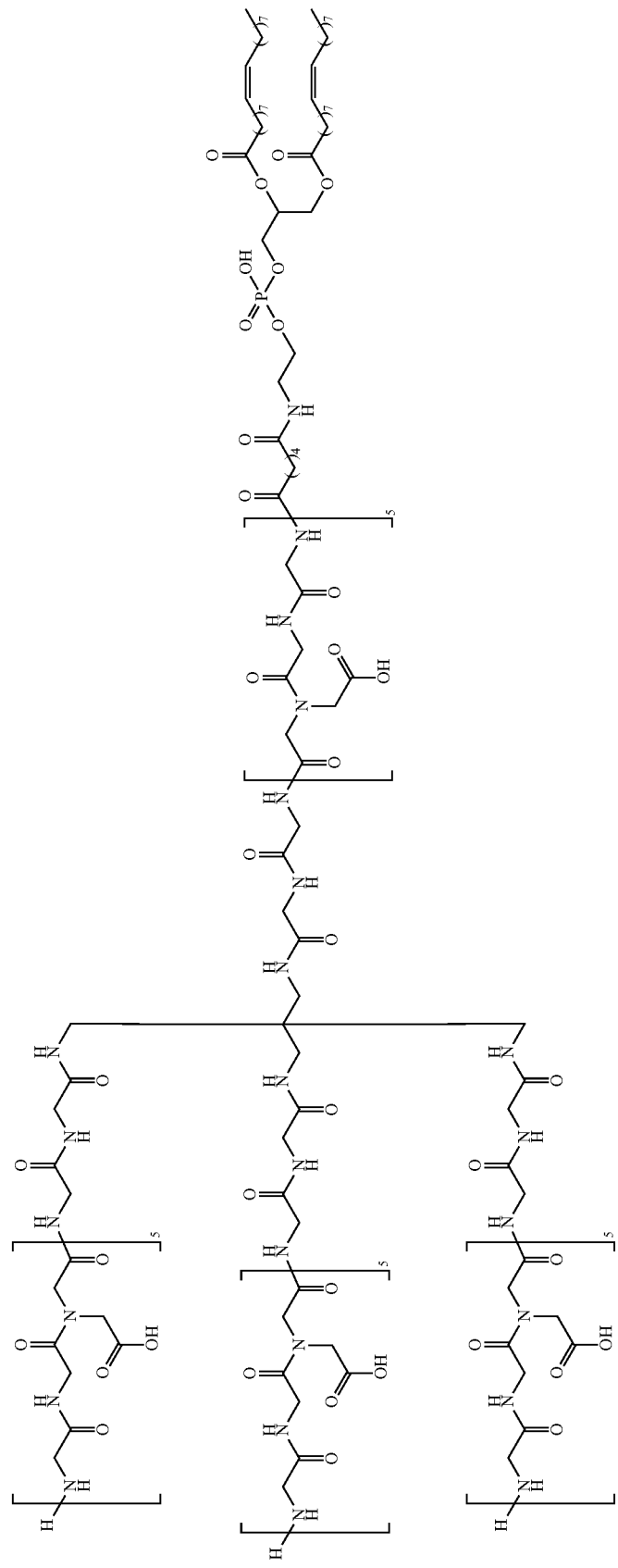
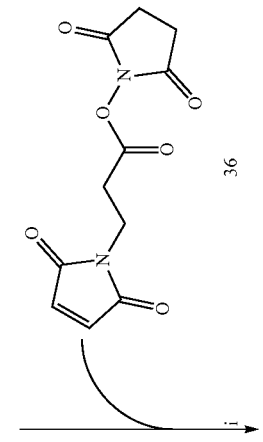

-continued
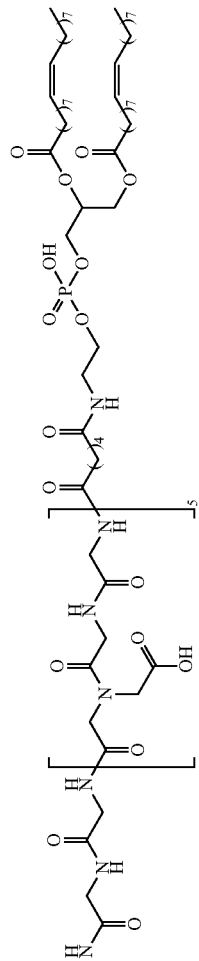
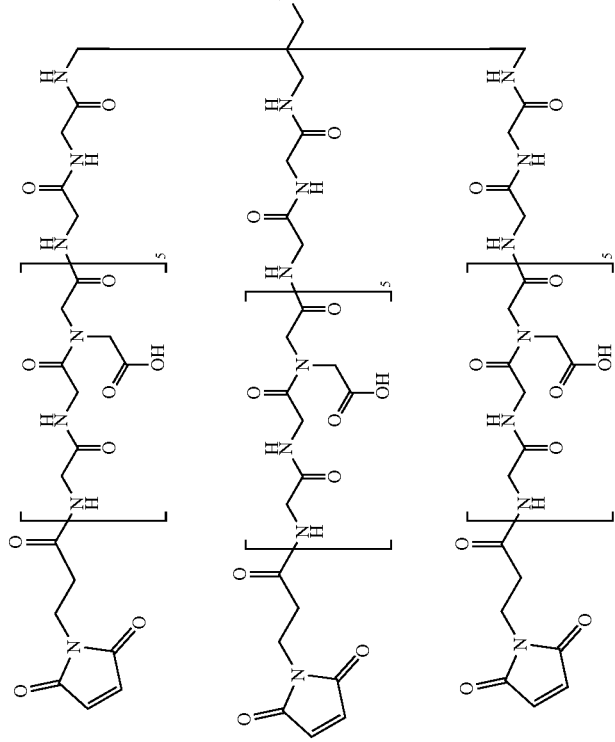

SCHEME X
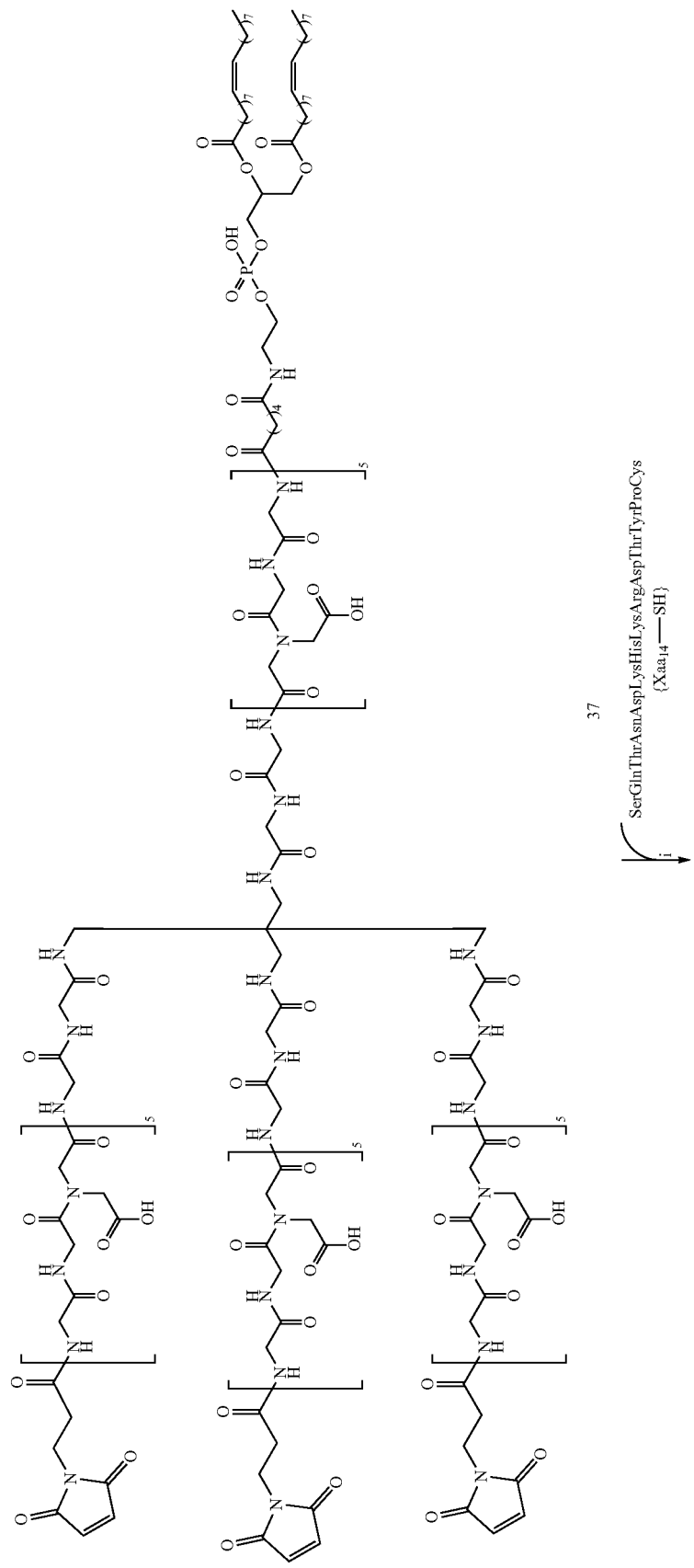

-continued
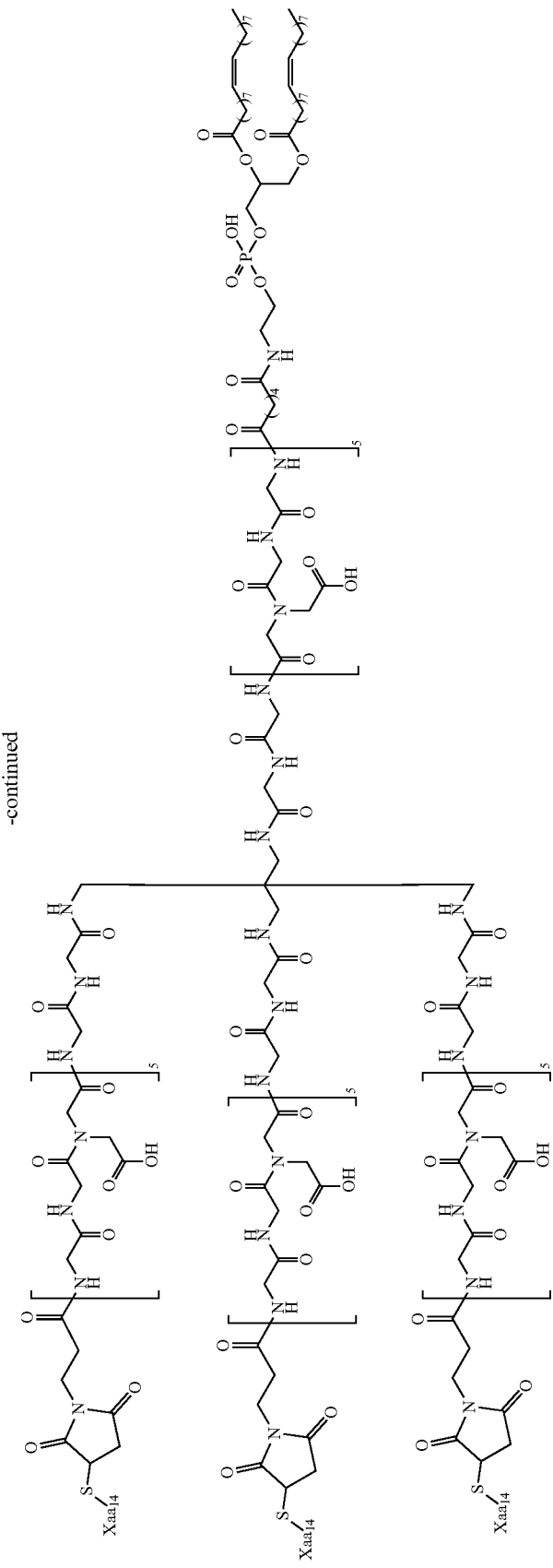

Preparation of (MUT21-Mal-βAla-(Gly₂CMGly)₅ Gly₂-NHCH₂)₃[DE-CO(CH₂)₄CO-(Gly₂CMGly)₅ Gly₂-NHCH₂]C (38) (Scheme X)

A quantity (12.5 mg, 7.4 μmol) of the 14-mer oligopeptide designated MUT21 (m.w. 1693.17Da):

SerGlnThrAsnAspLysHisLysArgAspThrTyrProCys
(SEQ ID NO: 01)

is prepared as a solution in 4 mL 0.1 M NMM in 30% aqueous isopropyl alcohol, pH 6.6. The solution is combined with 5 mL of the same buffer, in which a quantity (13.5 mg, 1.64 μmol) of 37 has been dissolved. The reaction mixture is stirred overnight at room temperature and centrifuged. The supernatant is dialyzed against unbuffered 30% (v/v) IPA-water for 24 hours and Milli-Q water using a dialysis bag with a cutoff molecular weight of 3.5 kDa (Spectra/Por 3) to remove residual oligopeptide material. The slurry obtained is then transferred into a lyophilization flask and freeze-dried to a constant weight. A quantity of 18.4 mg (84%) of construct 38 is obtained as an amorphous white powder. The expected signals ratio of low-field protons characteristic of peptide and lipid parts of the construct is revealed in $^1$H NMR (3 mg/mL in $D_2O/CD_3OD$ 2:1, 303 K, 700 MHz) (FIG. 8).

Comparative Chemistry

Preparation of {[2-(2-tert-butoxycarbonylamino-acetylamino)-acetyl]-methoxycarbonylmethyl-amino}-acetic acid methyl ester (7) (Step i of Comparative Scheme I)

An alternative method of preparing compound 7 was employed. N-Methylmorpholine (11.0 ml, 0.1 mol) was added to a stirred suspension of Boc-glycyl-glycine (23.2 g, 0.1 mol) in 150 ml methylene chloride, the solution was cooled to −15° C. and isobutyl chloroformate (13.64 g, 0.1 mol) was added for 10 min. Then 1-hydroxybenzotriazole and the solution of (methoxycarbonylmethylamino)-acetic acid methyl ester (7) (16.1 g, 0.1 mol) in 50 ml DMF were added to the compound 39 containing reaction mixture at the same temperature. The resulting mixture was stirred for 30 min at 0° C. then for 2 h at ambient temperature and evaporated to dryness. The residue was dissolved in 200 ml of methylene chloride and washed with 100 ml 0.5 M HCl and 200 ml 2% aq. NaHCO₃. Solvents were evaporated in vacuum and the residue was purified with column chromatography on silica gel (3% MeOH in CHCl₃) to give pure compound 7 (34.08 g, 91%) as a colourless glass. TLC: $R_f$=0.40 (5% MeOH in CHCl₃), $R_f$=0.49 (7:1 (v/v) chloroform/methanol).

$^1$H NMR (500 MHz, [$D_6$]DMSO, 30° C.) δ, ppm: 7.826 (t, J=5.1 Hz, 1H; NHCO), 6.979 (t, J=5.9 Hz, 1H; NHCOO), 4.348 and 4.095 (s, 2H; NCH₂COO), 3.969 (d, J=5.1 Hz, 2H; COCH₂NH), 3.689 and 3.621 (s, 3H; OCH₃), 3.559 (d, J=5.9 Hz, 2H; COCH₂NHCOO), 1.380 (s, 9H; C(CH₃)₃). $R_f$ 0.49 (7:1 (v/v) chloroform/methanol).

Preparation of {[2-(2-tert-butoxycarbonylamino-acetylamino)-acetyl]-methoxycarbonylmethyl-amino}-acetic acid (8) (Step ii of Comparative Scheme I)

0.2 M aqueous NaOH (325 ml) was added to a stirred solution of {[2-(2-tert-butoxycarbonylamino-acetylamino)-acetyl]-methoxycarbonylmethyl-amino}-acetic acid methyl ester (8) (24.42 g, 65.12 mmol) in methanol (325 ml), reaction mixture was kept for 15 min at ambient temperature, acidified with acetic acid (5 ml) and evaporated to dryness. Column chromatography of the residue on silica gel (methanol-ethyl acetate 1:1) gave the target compound as Na-salt (20.44 g) which was dissolved in methanol/water/pyridine mixture (20:10:1, 350 ml) and passed through ion-exchange column (Dowex 50X4-400, pyridine form, 300 ml) to remove Na cations. Column was washed with the same mixture, eluate evaporated and dried in vacuum to give pure compound 8 (20.15 g, 86%) as a white solid. TLC: $R_f$=0.47 (iPrOH/ethyl acetate/water 4:3:1).

$^1$H NMR (500 MHz, [$D_6$]DMSO, 30° C.), mixture of cis- and trans-conformers of N-carboxymethylglycine unit c.3:1. Major conformer; δ, ppm: 7.717 (t, J=5 Hz, 1H; NHCO), 7.024 (t, J=5.9 Hz, 1H; NHCOO), 4.051 (s, 2H; NCH₂COOCH₃), 3.928 (d, J=5 Hz, 2H; COCH₂NH), 3.786 (s, 2H; NCH₂COOH), 3.616 (s, 3H; OCH₃), 3.563 (d, J=5.9 Hz, 2H; COCH₂NHCOO), 1.381 (s, 9H; C(CH₃)₃) ppm; minor conformer, δ=7.766 (t, J=5 Hz, 1H; NHCO), 7.015 (t, J=5.9 Hz, 1H; NHCOO), 4.288 (s, 2H; NCH₂COOCH₃), 3.928 (d, J=5 Hz, 2H; COCH₂NH), 3.858 (s, 2H; NCH₂COOH), 3.676 (s, 3H; OCH₃), 3.563 (d, J=5.9 Hz, 2H; COCH₂NHCOO), 1.381 (s, 9H; C(CH₃)₃). $R_f$ 0.47 (4:3:1 (v/v/v) i-PrOH/ethyl acetate/water).

Preparation of {[2-(2-tert-butoxycarbonylamino-acetylamino)-acetyl]-methoxycarbonylmethyl-amino}-acetic acid N-oxysuccinimide ester (Boc-Gly₂(MCM)GlyOSu) (9) (Step iii of Comparative Scheme I)

N,N'-Dicyclohexylcarbodiimide (14.03 g, 68.10 mmol) was added to an ice-cooled stirred solution of {[2-(2-tert-butoxycarbonylamino-acetylamino)-acetyl]-methoxycarbonylmethyl-amino}-acetic acid (26.40 g, 73.13 mmol) and N-hydroxysuccinimide (8.70 g, 75.65 mmol) in DMF (210 ml). The mixture was stirred for 30 min at 0° C. then for 2 h at ambient temperature. Precipitated N,N'-dicyclohexylurea was filtered off, washed with DMF (80 ml). The filtrate and washings were concentrated and the residue was stirred with Et₂O (500 ml) for 1 h. Ether extract was decanted and the residue was concentrated to give

COMPARATIVE SCHEME I

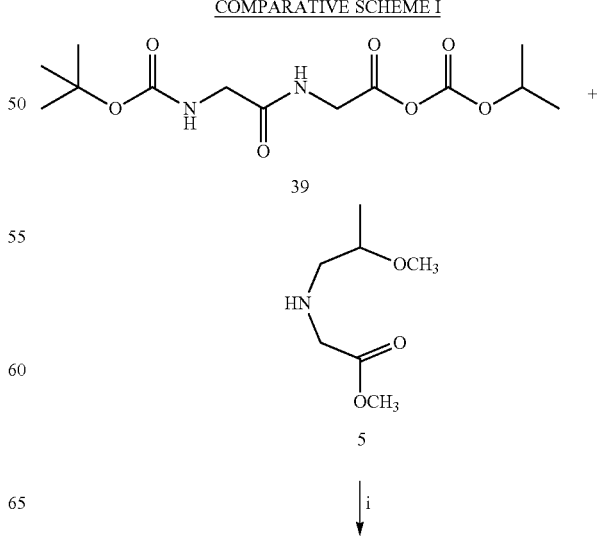

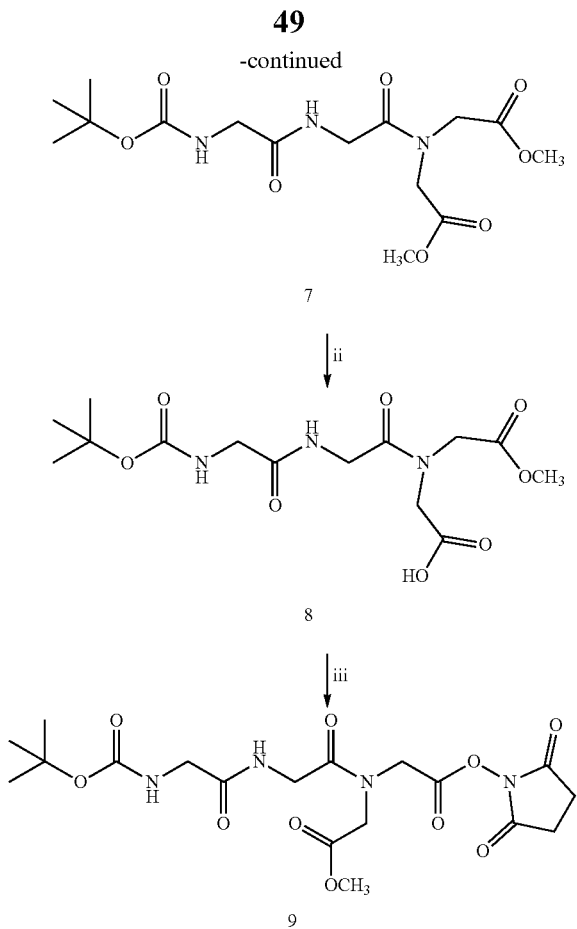

compound 9 as a white foam (32.57 g, 97%). TLC: R$_f$=0.71 (acetone/acetic acid 40:1). $^1$H NMR (500 MHz, DMSO[D$_6$], 30° C.), mixture of cis- and trans-conformers of N-carboxymethylglycine unit c. 3:2.

Major conformer; δ, ppm: 7.896 (t, J=5.1 Hz, 1H; NHCO), 6.972 (t, J=5.9 Hz, 1H; NHCOO), 4.533 (s, 2H; NCH$_2$COON), 4.399 (s, 2H; NCH$_2$COOCH$_3$), 3.997 (d, J=5.1 Hz, 2H; COCH$_2$NH), 3.695 (s, 3H; OCH$_3$), 3.566 (d, J=5.9 Hz, 2H; COCH$_2$NHCOO), 1.380 (s, 9H; C(CH$_3$)$_3$).

Minor conformer; δ, ppm: 7.882 (t, J=5.1 Hz, 1H; NHCO), 6.963 (t, J=5.9 Hz, 1H; NHCOO), 4.924 (s, 2H; NCH$_2$COON), 4.133 (s, 2H; NCH$_2$COOCH$_3$), 4.034 (d, J=5.1 Hz, 2H; COCH$_2$NH), 3.632 (s, 3H; OCH$_3$), 3.572 (d, J=5.9 Hz, 2H; COCH$_2$NHCOO), 1.380 (s, 9H; C(CH$_3$)$_3$).

R$_f$ 0.71 (40:1 (v/v) acetone/acetic acid).

Preparation of H$_2$N-CMG2-NH$_2$ (45) (Comparative Schemes II and III)

A solution of ethylenediamine (40) (808 mg, 13.47 mmol) and Et$_3$N (1.87 ml, 13.5 mmol) in DMSO (5 ml) was added to a stirred solution of Boc-Gly$_2$-(MCM)Gly-OSu (9) (15.42 g, 33.68 mmol) in DMSO (50 ml). The reaction mixture was stirred for 30 min at ambient temperature and acidified with acetic acid (1.2 ml), then fractionated with Sephadex LH-20 column (column volume 1200 ml, eluent—MeOH/water 2:1+0.2% AcOH). Fractions containing compound Boc$_2$MCMG (41) were combined, solvents evaporated and the residue was concentrated in vacuum. The product was additionally purified by silica gel column chromatography using 2-propanol/ethyl acetate/water (2:6:1) as eluent. Fractions containing pure Boc$_2$MCMG (41) were combined, solvents evaporated and a residue was dried in vacuum to give target Boc$_2$MCMG (41) as colourless foam (8.41 g, 84%). TLC: R$_f$=0.48 ($^i$PrOH/ethyl acetate/water 2:3:1).

$^1$H NMR (500 MHz, [D$_6$]DMSO, 30° C.), mixture of conformers~3:2: 8.166, 8.125, 7.917 and 7.895 (m, total 2H; 2 CONHCH$_2$), 7.793 (m, 2H; NHCH$_2$CH$_2$NH), 7.001 (br. t, 2H; 2 NHCOO), 4.277-3.893 (total 12H; 2 CH$_2$COO, 4NCH$_2$CO), 3.690 and 3.635 (s, total 6H; 2 COOCH$_3$), 3.567 (d, J=5.8 Hz, 4H; 2 CH$_2$NHCOO), 3.131 (m, 4H; NHCH$_2$CH$_2$NH), 1.379 (s, 18H; 2C(CH$_3$)$_3$) ppm.

MS, m/z: 769 [M+Na], 785 [M+K].

Trifluoroacetic acid (25 ml) was added to a stirred solution of Boc$_2$MCMG (41) (4.88 g, 6.535 mmol) in methylene chloride (25 ml) and the solution was kept for 1 h at ambient temperature. Then a reaction mixture was concentrated and the residue was evaporated three times with anhydrous MeOH (50 ml), then a residue was extracted three times with Et$_2$O (100 ml) to remove traces of trifluoroacetic acid. The resulted precipitate (as a white solid) was dried to give 5.06 g (~100%) of MCMG (42) as bis-trifluoroacetic salt. TLC: R$_f$=0.23 (ethanol/water/pyridine/acetic acid 5:1:1:1).

$^1$H NMR (500 MHz, D$_2$O, 30° C.), mixture of conformers~5:4: 4.400-4.098 (total 12H; 2 CH$_2$COO, 4 NCH$_2$CO), 3.917 (s, 4H; 2 COCH$_2$NH$_2$), 3.829 and 3.781 (s, total 6H; 2 COOCH$_3$), 3.394 (m, 4H; NHCH$_2$CH$_2$NH) ppm.

MS, m/z: 547 [M+H], 569 [M+Na], 585 [M+K].

A solution of Boc-Gly$_2$-(MCM)Gly-OSu (9) (7.79 g, 16.994 mmol) in DMSO (17 ml) and Et$_3$N (2.83 ml, 20.4 mmol) was added to the stirred solution of H$_2$N-MCMG-NH$_2$ (42) (5.06 g, 6.796 mmol) in DMSO (13 ml). The reaction mixture after stirring for 2 h at ambient temperature was acidified with acetic acid (4.0 ml) and fractionated with Sephadex LH-20 column chromatography (column volume 1200 ml, eluent—MeOH/water 2:1+0.2% AcOH). Fractions containing pure Boc$_2$MCMG2 (43) were combined, solvents evaporated and the residue was dried in vacuum to give target Boc$_2$MCMG2 (43) as colourless foam (8.14 g, 97%). TLC: R$_f$=0.25 ($^i$PrOH/ethyl acetate/water 2:3:1).

$^1$H NMR (500 MHz, [D$_6$]DMSO, 30° C.), mixture of conformers: 8.393-7.887 (total 6H; 6 CONHCH$_2$), 7.775 (m, 2H; NHCH$_2$CH$_2$NH), 6.996 (br. t, 2H; 2 NHCOO), 4.299-3.730 (total 28H; 4 CH$_2$COO, 10 NCH$_2$CO), 3.691 and 3.633 (s, total 12H; 4 COOCH$_3$), 3.564 (d, J=5.8 Hz, 4H; 2 CH$_2$NHCOO), 3.129 (m, 4H; NHCH$_2$CH$_2$NH), 1.380 (s, 18H; 2 C(CH$_3$)$_3$) ppm.

MS, m/z: 1256 [M+Na], 1271 [M+K].

Boc$_2$MCMG2 (43) (606 mg, 0.491 mmol) was dissolved in CF$_3$COOH (2 ml) and the solution was kept for 30 min at r.t. Trifluoroacetic acid was evaporated in vacuum and the residue was extracted three times with Et$_2$O (trituration with 25 ml of Et$_2$O followed by filtration) to remove residual CF$_3$COOH and the obtained white powder was dried in vacuum. The powder was dissolved in 4 mL of water and then was freeze-dried. Yield of H$_2$N-MCMG2-NH$_2$ (44) (TFA salt) was estimated as quantitative (actual weight was larger than theoretical by ~10% due to stability of hydrates). TLC: R$_f$=0.21 (ethanol/water/pyridine/acetic acid 5:1:1:1).

$^1$H NMR (500 MHz, [D$_2$]H$_2$O, 30° C.), mixture of conformers: 4.430-4.014 (total 28H; 4 CH$_2$COO, 10 NCH$_2$CO), 3.911 (s, 4H; 2 COCH$_2$NH$_2$), 3.823 and 3.772 (s, total 12H; 4 COOCH$_3$), 3.386 (m, 4H; NHCH$_2$CH$_2$NH) ppm.

MS, m/z: 1034 [M+H], 1056 [M+Na].

To the solution of H$_2$N-MCMG2-NH$_2$ (44) (~0.49 mmol) in water (20 mL) Et$_3$N (0.5 mL) was added, and the solution was kept for 15 h at r.t. The reaction mixture was evaporated to dryness and the residue was desalted on Sephadex LH-20 column (two methods): Method A. The residue was dissolved in water (3 ml) and the solution was desalted on Sephadex LH-20 column (column volume 250 mL, eluent—MeOH/water 1:1+0.05 M pyridine acetate). Fractions, containing H$_2$N-CMG2-NH$_2$ (45) contaminated with salts were combined separately, evaporated and the residue was desalted again. Combined fractions, containing pure H$_2$N-CMG2-NH$_2$ (45), were evaporated to ~4 ml volume and freeze dried. Yield of H$_2$N-CMG2-NH$_2$ (45) (internal salt) was 431 mg (90%). Method B. The residue was dissolved in water (3 ml) and the solution was desalted on Sephadex LH-20 column (column volume 250 mL, eluent—MeOH/water 1:1+1% conc. aq. NH$_3$). Fractions, containing pure H$_2$N-CMG2-NH$_2$ (45), were evaporated to ~4 ml volume and freeze dried. The residue (ammonia salt of H$_2$N-CMG2-NH$_2$ (45)) was dissolved in $^i$PrOH/water 1:1 mixture (10 mL), Et$_3$N (0.2 mL) was added, and the solution was evaporated to dryness. This procedure was repeated twice; the residue was dissolved in 4 mL of water and freeze-dried. Yield of the di-Et$_3$N salt of H$_2$N-CMG2-NH$_2$ (45) was 549 mg (95%).

TLC: R$_f$=0.50 ($^i$PrOH/MeOH/acetonitrile/water 4:3:3:4+3% conc. aq. NH$_3$), or R$_f$=0.43 ($^i$PrOH/EtOH/MeOH/water 1:1:1:1, 0.75M NH$_3$).

$^1$H NMR of H$_2$N-CMG2-NH$_2$ (45) internal salt (500 MHz, [D$_2$]H$_2$O, 30° C.), mixture of conformers: 4.328-4.006 (total 28H; 4 CH$_2$COO, 10 NCH$_2$CO), 3.907 (s, 4H; 2 COCH$_2$NH$_2$), 3.381 (m, 4H; NHCH$_2$CH$_2$NH) ppm.

MS, m/z: 977 [M+H], 999 [M+Na], 1015 [M+K].

Preparation of H$_2$N-CMG2-Ad-DOPE (46) (Comparative Scheme IV)

To the intensively stirred solution of H$_2$N-CMG2-NH$_2$ (45) (425 mg, 0.435 mmol of internal salt) in i-PrOH/water mixture (i-PrOH/water 3:2, 10 mL) the 1 M aq. solution of NaHCO$_3$ (0.435 mL, 0.435 mmol) and then the solution of DOPE-Ad-OSu (23) (211 mg, 0.218 mmol) in dichloroethane (0.4 mL) were added. The reaction mixture was stirred for 2 h and then acidified with 0.2 mL of AcOH and evaporated to minimal volume at 35° C. The solid residue was dried in vacuum (solid foam) and then thoroughly extracted with CHCl$_3$/MeOH mixture (CHCl$_3$/MeOH 4:1, several times with 10 mL, TLC control). The extracted residue consisted of unreacted H$_2$N-CMG2-NH$_2$ (45) and salts (about 50% of H$_2$N-CMG2-NH$_2$ (45) was recovered by desalting of combined the residue and a fractions after chromatography on silica gel according to procedure described in the H$_2$N-CMG2-NH$_2$ (45) synthesis). The combined CHCl$_3$/MeOH extracts (solution of H$_2$N-CMG2-Ad-DOPE (46), DOPE-Ad-CMG2-Ad-DOPE, N-oxysuccinimide and some H$_2$N-CMG2-NH$_2$ (45)) were evaporated in vacuum and dried. The obtained mixture was separated on silica gel column (2.8×33 cm, ~200 mL of silica gel in CHCl$_3$/MeOH 5:1). The mixture was placed on column in MeOH/CHCl$_3$/water mixture (MeOH/CHCl$_3$/water 6:3:1+0.5% of pyridine) and the components were eluted in a stepwise ternary gradient: MeOH/CHCl$_3$/water composition from 6:3:1 to 6:2:1 and then to 6:2:2 (all with 0.5% of pyridine). DOPE-Ad-CMG2-Ad-DOPE was eluted first (R$_f$=0.75, MeOH/CHCl$_3$/water 3:1:1), followed by desired H$_2$N-CMG2-Ad-DOPE (46) (R$_f$=0.63, MeOH/CHCl$_3$/water 3:1:1), last eluted was H$_2$N-CMG2-NH$_2$ (45) (R$_f$=0.31, MeOH/CHCl$_3$/water 3:1:1). Fractions, containing pure H$_2$N-CMG2-Ad-DOPE (46) were combined and evaporated to dryness. To remove any low molecular weight

COMPARATIVE SCHEME II

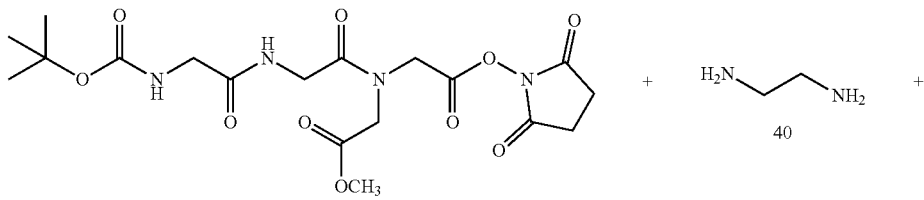

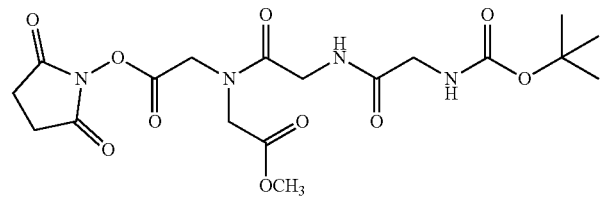

53 54
-continued
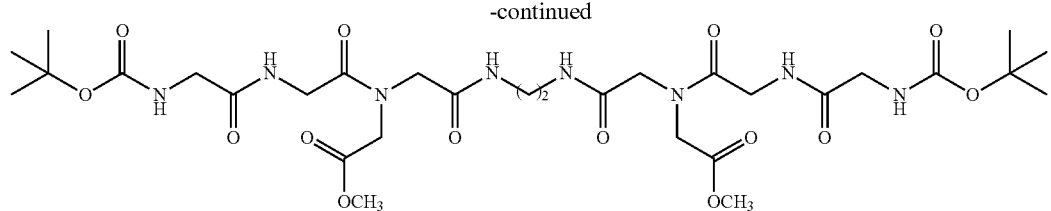
41
↓ ii
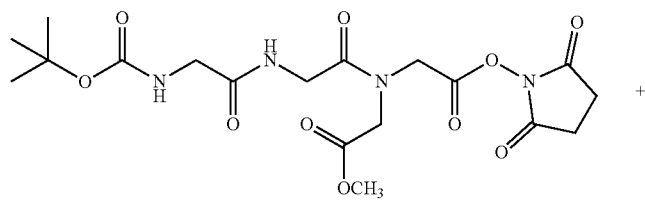
42
COMPARATIVE SCHEME III
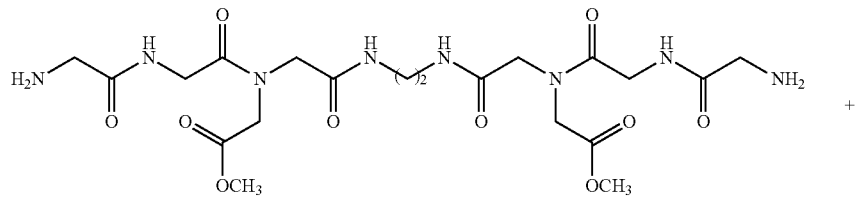
9 +
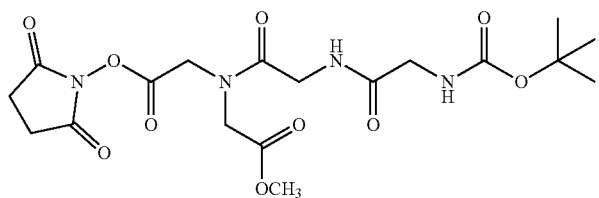
42 +
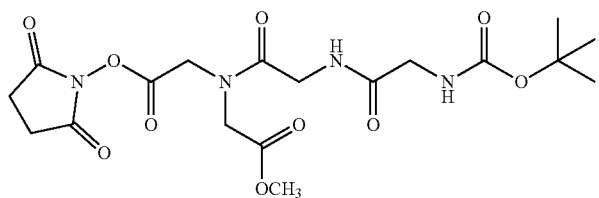
9
↓ i

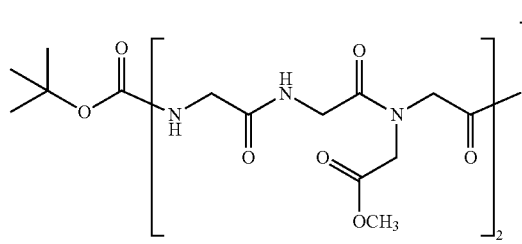
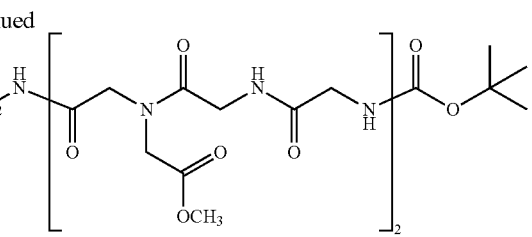

43

↓ ii

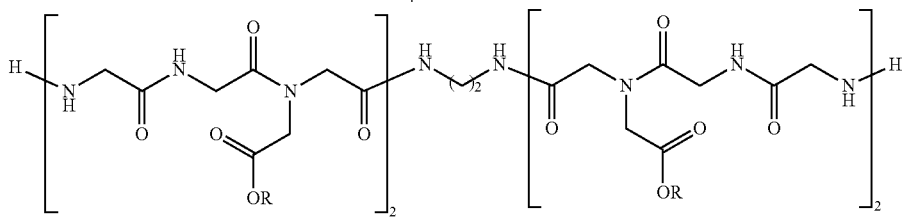

44 (R is CH₃); 45 (R is H)

impurities and solubilised silica gel the residue was dissolved in $^i$PrOH/water 1:2 mixture (2 mL), and was passed through Sephadex LH-20 column (column volume 130 mL, eluent—$^i$PrOH/water 1:2+0.25% of pyridine). Fractions containing pure H₂N-CMG2-Ad-DOPE (46) were combined and evaporated (~20% of 2-propanol was added to prevent foaming) to dryness, the residue was dissolved in water (~4 mL) and freeze-dried. Yield of H₂N-CMG2-Ad-DOPE (46) was 270 mg (68% on DOPE-Ad-OSu or 34% on H₂N-CMG2-NH₂ (45)).

$^1$H NMR (500 MHz, [D₂]H₂O/[D₄]CH₃OH 2:1, 30° C.): 5.505 (m, 4H; 2 CH₂C$\underline{H}$=C$\underline{H}$CH₂), 5.476 (m, 1H; OCH₂C$\underline{H}$CH₂O), 4.626 (dd, $J_{gem}$=11.6 Hz, 1H; OC$\underline{H}$CHCH₂O), 4.461-4.084 (total 37H; 4 CH₂COO, 11 NCH₂CO, OC$\underline{H}$CHCH₂O, OCH₂CH₂N), 4.002 (s, 2H; COC$\underline{H}_2$NH₂), 3.573 (m, 4H; NHC$\underline{H}_2$C$\underline{H}_2$NH), 2.536-2.463 (m, total 8H; 4 CH₂CO), 2.197 (m, 8$\underline{H}$; 2 C$\underline{H}_2$CH=CHC$\underline{H}_2$), 1.807 (m, 8H; 4 C$\underline{H}_2$CH₂CO), 1.480 (m, 40H; 20 CH₂), 1.063 (~t, J≈6 Hz, 6H; 2 CH₃) ppm.

MS, m/z: 1831 [M+H].

Preparation of Galili-CMG2-Ad-DOPE (47) (Comparative Scheme V)

To a stirred solution of compound 34 (66 mg, 0.079 mmol) in dry DMSO (6 mL) were added 15 μl Et₃N and powdered H₂N-CMG2-Ad-DOPE (46) (95 mg, 0.0495 mmol) in 3 portions. The mixture was stirred for 24 h at room temperature and then subjected to column chromatography (Sephadex LH-20, i-PrOH—H₂O, 1:2, 0.5 v % Py, 0.25 v % AcOH) to yield the crude compound 47 in a form of Py-salt; The compound was lyophilized from water two times, then dissolved again in 10 ml of water, aqueous solution of NaHCO₃ (50 mM) was added to pH 6.5 for obtaining the compound 47 in a form of Na-salt and the solution was subjected to lyophilization. The yield of compound 47 (Na-salt) was 114 mg (86% based on NH₂—CMG₂-DE), $R_f$ 0.6 (i-PrOH-MeOH-MeCN—H₂O, 4:3:6:4).

$^1$H NMR (700 MHz, D₂O—CD₃OD, 1:1 (v/v), 40° C.; selected signals) δ, ppm: 1.05 (t, J 7.03 Hz, 6H; 2 C$\underline{H}_3$), 1.40-1.58 (m, 40H; 20 C$\underline{H}_2$), 1.73-1.87 (m, 12H; 2×—COCH₂C$\underline{H}_2$CH₂CH₂CO and 2×—COCH₂C$\underline{H}_2$—), 1.90-1.99 (m, 2H; OCH₂C$\underline{H}_2$CH₂N), 2.15-2.25 (m, 11H; 2×—C$\underline{H}_2$CH=CHCH₂—, NHC(O)C$\underline{H}_3$), 2.39-2.59 (2m, total 12H, 2×—COCH₂C$\underline{H}_2$CH₂CH₂CO— and 2×—COCH₂C$\underline{H}_2$—) 4.63 (dd, 1H, J 2.51, J 12.20, C(O)OC$\underline{H}$HCHOCH₂O—), 4.67 and 4.69 (2d×1H, $J_{1,2}$ 7.81, $J_{1,2}$ 7.95, H-1$^I$, H-1$^{II}$), 5.30 (d, 1H, $J_{1,2}$ 3.88, H-1$^{III}$), 5.42-5.46 (m, 1H, —OCH₂—C$\underline{H}$O—CH₂O—), 5.49-5.59 (m, 4H, 2×—C$\underline{H}$=C$\underline{H}$—); MALDI TOF mass-spectrum, M/Z: 2567 (M+Na); 2583 (M+K); 2589 (MNa+Na); 2605 (MNa+K); 2611 (MNa₂+Na).

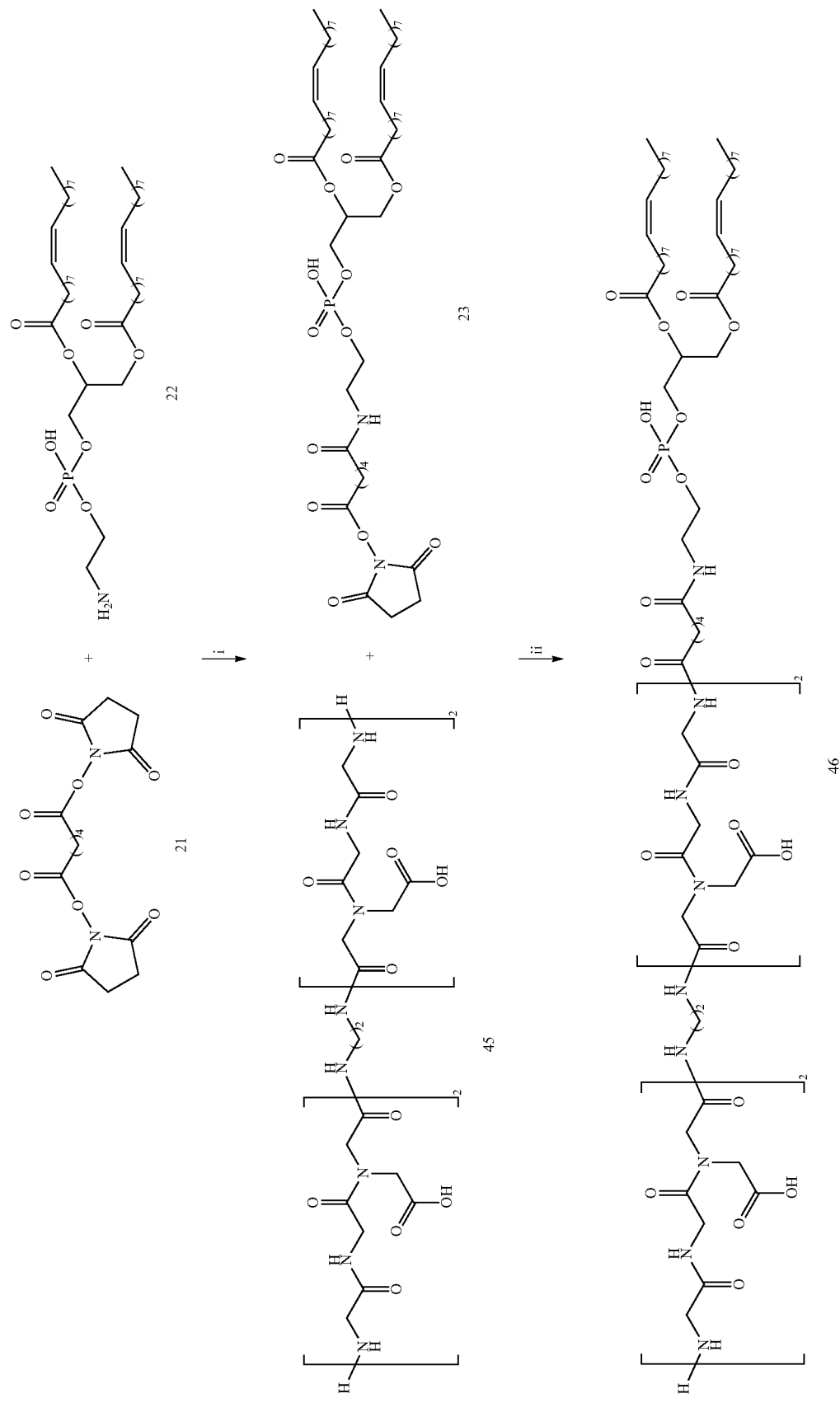

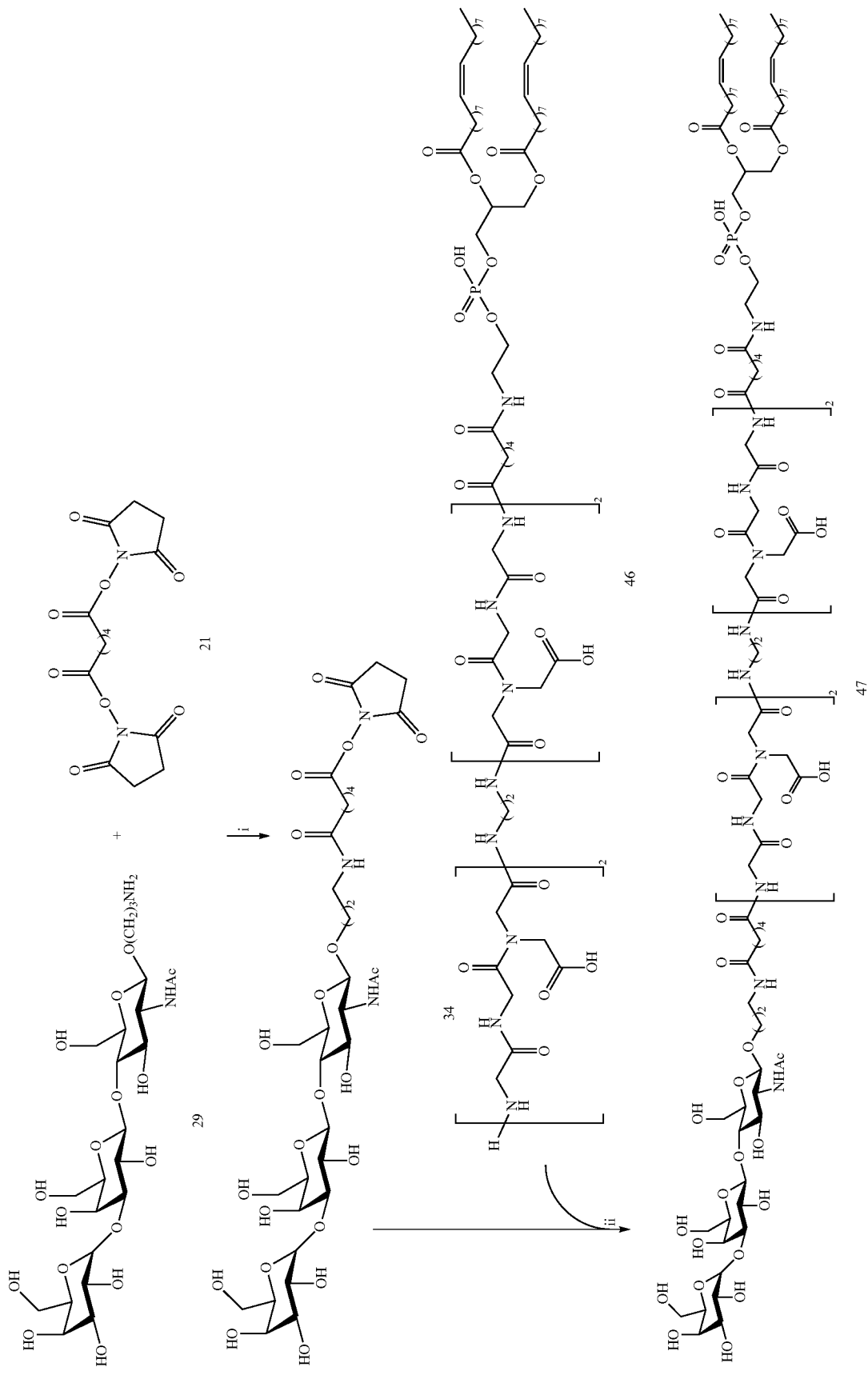

Preparation of GalNAcα1-3Galβ1-4GlcNAc-Ad-DOPE (33) (Comparative Scheme VI)

To a solution of the product 23 (33 μmol) in N,N-dimethylformamide (1 ml), 30 μmol of the 3-aminopropyltrisaccharide 33 and 5 μl of triethylamine (Et$_3$N) were added. The mixture was stirred for 2 h at room temperature. Column chromatography on silica gel (CH$_2$Cl$_2$-EtOH—H$_2$O; 6:5:1) provided an 81% yield of the construct 48.

48: $^1$H NMR (700 MHz, CDCl$_3$—CD$_3$OD, 1:1 v/v, selected), δ, ppm: 1.05 (t, 6H, J 7.05, 2CH$_3$), 1.39-1.55 (m, 40H, 20CH$_2$), 1.75-1.84 (m, 8H, COCH$_2$CH$_2$CH$_2$CH$_2$CO and 2×COCH$_2$CH$_2$—), 1.84-1.96 (m, 2H, O—CH$_2$CH$_2$CH$_2$—NH), 2.15-2.22 (m, 14H, 2×(—CH$_2$—CH=CH—CH$_2$—), 2×NHC(O)CH$_3$), 2.34-2.46 (m, 4H, 2×—CH$_2$—CO), 2.36-2.44 (m, 4H, 2×—CH$_2$—CO), 3.29-3.34 (m, 1H, —CH$_2$—CHH—NH), 4.17-4.20 (m, 2H, —CHO—CH$_2$OP—), 4.34-4.39 (m, 2H, —CH$_2$OPO—CH$_2$—CH$_2$), 4.57 (d, 1H, J$_{1,2}$ 8.39, H-1$^I$), 4.50 (dd, 1H, J 3.78, J 10.82, —C(O)OCHHCHOCH$_2$O—), 4.58-4.61 (m, 2H, H-1$^{II}$, C(O)OCHHCHOCH$_2$O—), 5.15 (d, 1H, J$_{1,2}$ 3.76, H-1$^{III}$), 5.38-5.42 (m, 1H, —OCH$_2$—CHO—CH$_2$O—), 5.47-5.53 (m, 4H, 2×—CH=CH—). R$_f$ 0.5 (CH$_2$Cl$_2$-EtOH—H$_2$O; 6:5:1).

Preparation of Galα1-3Galβ1-4GlcNAc-Ad-DOPE (49) (Comparative Scheme VII)

Construct 49 was prepared according to the same method employed for the preparation of construct 48. Eluent for column chromatography on silica gel: CH$_2$Cl$_2$-EtOH—H$_2$O; 6:5:1, yield of construct 49-84%;

49: $^1$H NMR (700 MHz, CDCl$_3$—CD$_3$OD, 1:1 v/v, selected signals), δ, ppm: 1.05 (t, 6H, J 6.98, 2 CH$_3$), 1.36-1.55 (m, 40H, 20 CH$_2$), 1.73-1.84 (m, 8H, COCH$_2$CH$_2$CH$_2$CH$_2$CO and 2×(COCH$_2$CH$_2$—), 1.85-1.96 (m, 2H, O—CH$_2$CH$_2$CH$_2$—NH), 2.14-2.22 (m, 11H, 2×(—CH$_2$—CH=CH—CH$_2$—), NHC(O)CH$_3$), 2.45-2.52 (m, 4H, 2×—CH$_2$—CO), 2.36-2.45 (m, 4H, 2×—CH$_2$—CO), 3.29-3.35 (m, 1H, —CH$_2$—CHH—NH), 3.52-3.62 (m, 3H, PO—CH$_2$—CH$_2$—NH, —CH$_2$—CHH—NH), 4.13-4.18 (m, 2H, —CHO—CH$_2$OP—), 4.19 (d, 1H, J$_{3,4}$ 2.48, H-4$^{II}$), 4.36 (dd, 1H, J 6.8, J 12.00, —C(O)OCHHCHOCH$_2$O—), 4.56 (d, 1H, J$_{1,2}$ 8.39, H-1$^I$), 4.60 (dd, 1H, J 2.87, J 12.00, C(O)OCHHCHOCH$_2$O—), 4.61 (d, 1H, J$_{1,2}$ 7.57, H-1$^{II}$), 5.18 (d, 1H, J$_{1,2}$ 2.52, H-1$^{III}$), 5.34-5.43 (m, 1H, —OCH$_2$—CHO—CH$_2$O—), 5.45-5.54 (m, 4H, 2×—CH=CH—). R$_f$ 0.45 (CH$_2$Cl$_2$-EtOH—H$_2$O; 6:5:1).

COMPARATIVE SCHEME VI

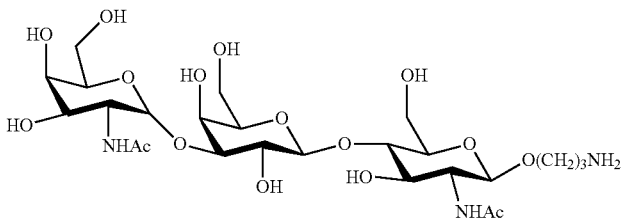

33

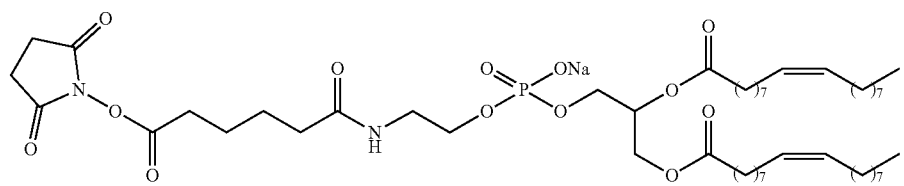

23

↓ i

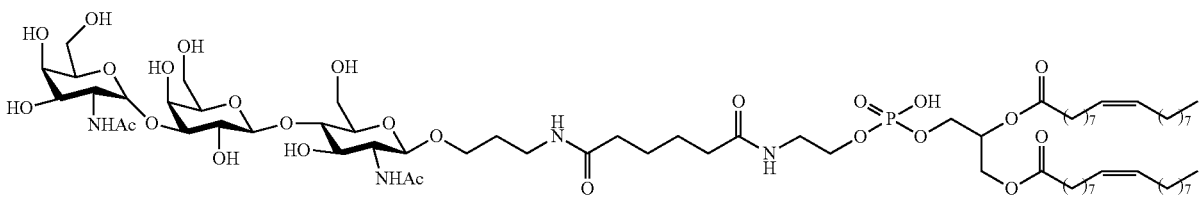

48

COMPARATIVE SCHEME VII

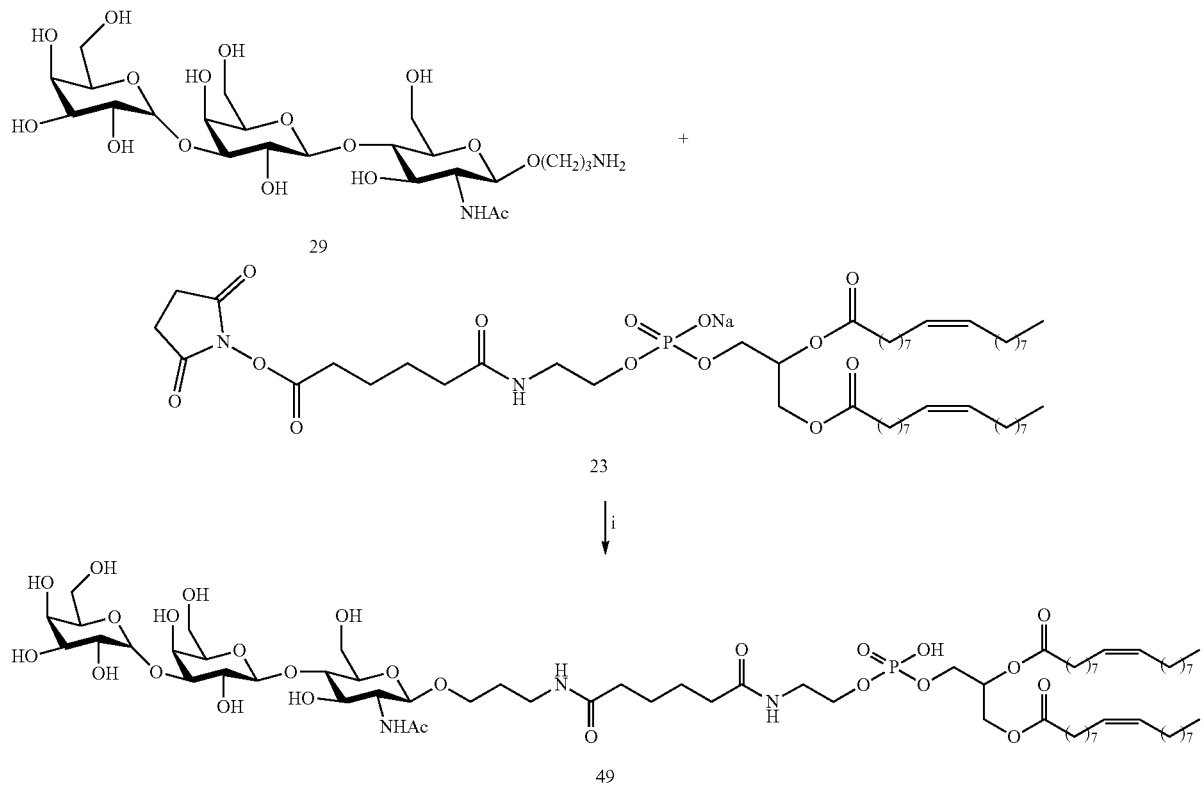

Biology

Preparation of Kodecytes

Stock solutions of constructs (35, 47, 48 and 49) were prepared at a concentration of 1 mg/mL in a red blood cell (RBC) preservative solution (CELPRESOL™, CSL Limited). Prior to dilution each stock solution was vortexed for 45 seconds at room temperature (r.t.). A volume of 100 μL of diluted stock solution was added to a volume of 100 μL centrifugally packed RBCs (packed cell volume; PCV). The total volume of 200 μL suspended RBCs was incubated at 37° C. for 2 hours before washing with CELPRESOL™ and re-suspending the modified RBCs ("kodecytes") at a concentration of 5% PCV in CELPRESOL™.

Preparation of Drabkins Solution

Amounts of 200 mg potassium ferricyanide ($K_3Fe(CN)_6$), 50 mg potassium cyanide (KCN) and 140 mg potassium dihydrogen phosphate ($KH_2PO_4$) and a volume of 1 mL nonionic surfactant (Triton X-100) were dissolved in deionised water and made up to a volume of 1 L. The solution was stored in glass bottles in the dark and pH confirmed to be in the range 7.0 to 7.4 before use.

Preparation of EDTA solution

Amounts of 4.45 g ethylenediaminetetraacetic acid (EDTA) as its dipotassium salt ($K_2H_2EDTA$) and 0.3 g sodium hydroxide (NaOH) were dissolved in deionised water and made up to a volume of 100 mL.

Detection of Antibodies in Patient Plasma

The ability of kodecytes prepared using different constructs to detect the presence of antibodies in samples of plasma was compared by a method analogous to that described in Bovin et al (2009). The results are presented in Table 1 and are consistent with an increased avidity for MUT21 binding antibodies (if present) in the sera of subjects.

Complement Induced Cell Lysis

Prior to use kodecytes were washed and re-suspended 5% PCV in phosphate buffered saline (PBS). Uniformity of concentration of RBCs was confirmed by adding a volume of 40 μL of kodecyte suspension to a volume of 1 mL of Drabkins solution and the absorbance measured at 540 nm against Drabkins solution (blank). Variations in measured absorbances was reduced to less than 10% by adjustment of suspending volume.

The ability of constructs to induce complement mediated autolysis was evaluated by a method analogous to that described in the publication of Henry and Komarraju (2012). For the present studies kodecytes prepared using construct 49 were used as a 100% lysis control. A volume of 200 μL pooled AB serum and a volume of 100 μL kodecytes prepared using construct 49 at a concentration of 750 μg/mL was used as the 100% lysis control. A volume of 200 μL pooled AB serum and a volume of 100 μL O group RBCs (prepared as kodecytes without the addition of construct) was used as the 0% lysis control. To measure the ability of constructs to induce complement mediated autolysis of kodecytes volumes of 200 μL of pooled AB serum were dispensed into duplicate sets of test tubes. A volumes of 100 μL kodecytes was added to the tubes before incubation at 37° C. for 1 hour. Following incubation a volume of 1 μL ethylenediaminetetraacetic acid (EDTA) as its dipotassium salt

TABLE 1

Agglutination scores determined using samples of: naturally occurring Mia RBCs ("positive" control), kodecytes prepared using the construct 38 and its monomeric counterpart at the concentrations indicated, and unmodified RBCs (negative control). [1]the construct 'monomeric MUT21' was prepared according to the method disclosed in the publication of Bovin et al (2009) using construct 46.

| | | Concentration and construct used in the preparation of kodecytes | | | | |
|---|---|---|---|---|---|---|
| | | Trimeric MUT21 (38) | | Monomeric MUT21[1] | | |
| Plasma sample No. | 0.8% Natural Mia RBCs | 0.01 mg/mL 0.00098 mM/L | 0.03 mg/mL 0.00293 mM/L | 0.03 mg/mL 0.00879 mM/L | 0.01 mg/mL 0.00293 mM/L | 0.8% PCV unmodified RBCs |
| 3 | 8 | 0 | 0 | 0 | 0 | 0 |
| 4 | 10 | 8 | 10 | 8 | 3 | 0 |
| 8 | 8 | 0 | 0 | 0 | 0 | 0 |
| 9 | 8 | 0 | 0 | 0 | 0 | 0 |
| 11 | 10 | 0 | 0 | 0 | 0 | 0 |
| 12 | 10 | 0 | 0 | 0 | 0 | 0 |
| 14 | 8 | 0 | 0 | 0 | 0 | 0 |
| 17 | 10 | 0 | 0 | 0 | 0 | 0 |
| 18 | 10 | 0 | 0 | 0 | 0 | 0 |
| 19 | 10 | 0 | 0 | 0 | 0 | 0 |
| 20 | 8 | 0 | 0 | 0 | 0 | 0 |
| 22 | 10 | 0 | 0 | 0 | 0 | 0 |
| 24 | 10 | 0 | 0 | 0 | 0 | 0 |
| 25 | 10 | 0 | 0 | 0 | 0 | 0 |
| 26 | 8 | 0 | 0 | 0 | 0 | 0 |
| 27 | 8 | 0 | 0 | 0 | 0 | 0 |
| 29 | 10 | 0 | 0 | 0 | 0 | 0 |
| 32 | 10 | 3 | 5 | 0 | 0 | 0 |
| 33 | 8 | 0 | 0 | 0 | 0 | 0 |
| 34 | 8 | 5 | 8 | 8 | 0 | 0 |
| 35 | 10 | 0 | 0 | 0 | 0 | 0 |
| 36 | 12 | 8 | 8 | 3 | 0 | 0 |

TABLE 2

Construct used in the preparation of kodecytes and the observed degree of cell lysis (qualitative).

| Construct | Degree of lysis |
|---|---|
| 49 | Partial |
| 35 (0.66 μM) | Complete |
| 35 (0.33 μM) | Complete |
| 47 | Partial |
| 48 | Complete |
| 100% lysis control | Complete |
| 0% lysis control | None |

TABLE 3

Construct used in the preparation of kodecytes, absorbance (abs, 540 nm) measured for duplicate samples, percentage of cells lysed relative to 100% control and calculated percentage of cells lysed using standard curve.

Figure 2:
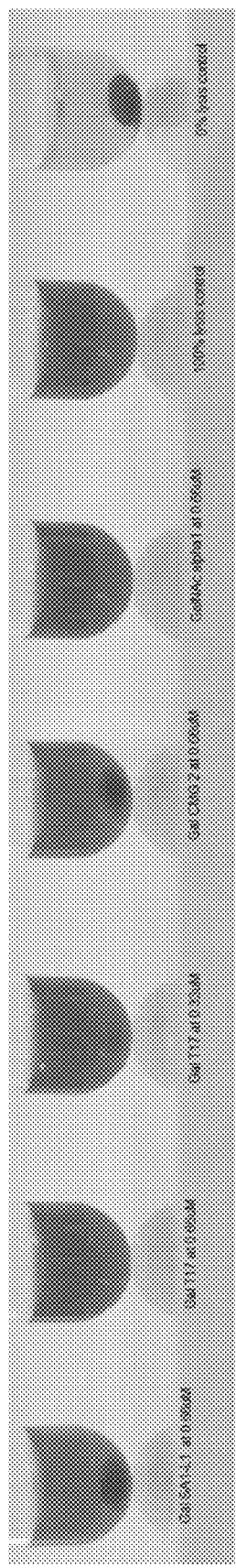
FIG. 2. Photograph of test tubes following complement induced lysis. The notations in the photograph correspond to the use of the following constructs in the preparation of the kodecytes (at the concentrations indicated): Gal SA1-L1 (49), Gal T17 (35), Gal CMG 2 (47) and GalNAc alpha1 (48).

| Construct | Abs 1 | Abs 2 | (A1 and A2) | Measured % | Calculated % |
|---|---|---|---|---|---|
| 49 | .178 | .187 | .183 | Set as 100 | 51 |
| 30 (0.66 μM) | .351 | .358 | .355 | 194 | 97 |
| 30 (0.33 μM) | .358 | .326 | .342 | 187 | 93 |
| 47 | .224 | .243 | .234 | 128 | 65 |
| 48 | .349 | .345 | .347 | 190 | 95 |
| 100% lysis control | .303 | .310 | .307 | Not applicable | 85 |
| 0% lysis control | .027 | .005 | .016 | Not applicable | 7 | was added to each to each test tube to provide a final concentration of 0.1 mM EDTA. The test tubes were then centrifuged and the characteristics of the sedimented RBCs and supernatant observed (Table 2 and FIG. 2). In addition a volume of 160 μL of the cell free supernatant was removed and added to a volume of 1 mL of Drabkins solution. The absorbance of the solution was then measured at 540 nm against a volume of 160 μL pooled AB serum added to a volume of 1 mL of Drabkins solution (blank). The absorbance of the supernatant was calculated as a percentage of the initial absorbance of the suspension of kodecytes. The percentage of cells lysed was calculated against a standard curve.

Kodecytes prepared using the multivalent ligand construct 35 appear to be approximately twice as sensitive to autolysis as kodecytes prepared using the construct 49. The half molar and molar equivalents produced approximately equal degrees of cell lysis. Kodecytes prepared using the construct 47 were somewhat more sensitive to lysis than kodecytes prepared using the construct designated 49. (This observation is consistent with the observations for antibody induced agglutination with kodecytes prepared using construct 38.) Kodecytes prepared using the construct 48 appear to be approximately twice as sensitive to lysis as kodecytes prepared using the construct 49. These observations are submitted to be predictive of the efficacy of the constructs when employed in the method of treating patients with tumours as disclosed in the publication of Galili et al (2015).

Although the invention has been described with reference to embodiments or examples it should be appreciated that variations and modifications may be made to these embodiments or examples without departing from the scope of the invention. For example, it is anticipated that bis(N-hydroxysuccinimidyl) succinate, bis(N-hydroxysuccinimidyl) glutarate, bis(N-hydroxysuccinimidyl) pimelate and bis(N-hydroxysuccinimidyl) suberate may each be substituted for the use of bis(N-hydroxysuccinimidyl) adipate (21) in the preparation of the compounds 23 and 34.

Where known equivalents exist to specific elements, features or integers, such equivalents are incorporated as if specifically referred to in this specification. For example, the preparation of 3-aminopropylglycosides other than those specifically described in here are disclosed in the publications of Audibert et al (1987), Bovin et al (1993), Galanina et al (1997), Karelin et al (2010), Korchagina and Bovin (1992), Korchagina et al (2009), Krylov et al (2007), Nifant'ev et al (1996), Pazynina et al (2003), Pazynina et al (2014), Ryzhov et al (2012), Sherman et al (2001), Vodovozova et al (2000) and Yashunsky et al (2016). In particular, variations and modifications to the embodiments or examples that include elements, features or integers disclosed in and selected from the referenced publications are within the scope of the invention unless specifically disclaimed. It is anticipated that the 3-aminopropylglycosides disclosed elsewhere may be substituted for the compounds 29 and 33 in the synthetic schemes described here.

The advantages provided by the invention and discussed in the description may be provided in the alternative or in combination in these different embodiments of the invention.

REFERENCED PUBLICATIONS

Audibert et al (1987) Conjugates of haptenes and muramyl-peptides, endowed with immunogenic activity and compositions containing them U.S. Pat. No. 4,639,512.

Barr et al (2014) *Mapping the fine specificity of ABO monoclonal reagents with A and B type-specific FSL constructs in kodecytes and inkjet printed on paper* Transfusion, 54, 2477-2484.

Barr et al (2015) *Monoclonal anti-A activity against the FORS1 (Forssman) antigen* Transfusion, 55, 129-136.

Blake et al (2011) *FSL constructs: a simple method for modifying cell/virion surfaces with a range of biological markers without affecting their viability* J. Vis. Exp., 54, e3289; DOI: 10.3791/3289.

Bovin et al (1993) *Synthesis of polymeric neoglycoconjugates based on N-substituted polyacrylamides* Glycoconjugate Journal 10, 142-151.

Bovin et al (2005) Synthetic membrane anchors International application no. PCT/NZ2005/000052 (publ. no. WO 2005/090368).

Bovin et al (2009) Functional lipid constructs International application no. PCT/NZ2008/000266 (publ. no. WO 2009/048343).

Bovin et al (2010) Multiligand constructs International application no. PCT/EA2008/000006 (publ. no. WO 2010/043230).

Carter et al (2006) Cell Surface Coating with Hyaluronic Acid Oligomer Derivative US Patent WO/2007/035116.

Carter et al (2007) Cell Surface Coating with Hyaluronic Acid Oligomer Derivative International application no. PCT/NZ2006/000245 [publ. no. WO 2007/035116].

Frame et al (2007) *Synthetic glycolipid modification of red blood cell membranes* Transfusion, 47, 876-882.

Galanina et al (1997) *Further refinement of the description of the ligand-binding characteristics for the galactoside-binding mistletoe lectin, a plant agglutin with immunomodulatory potency* Journal of Molecular Recognition, 10, 139-147.

Galili et al (2015) Glycolipid containing compositions for use in the treatment of tumours International application no. PCT/GB2015/051368 [publ. no. WO 2015/170121].

Georgakopoulos et al (2012) *An improved Fc function assay utilizing CMV antigen coated red blood cells generated with synthetic function-spacer-lipid constructs* Vox Sanguinis, 102, 72-78.

Harrison et al (2010) *A synthetic globotriaosylceramide analogue inhibits HIV-1 infection in vitro by two mechanisms* Glycoconj. J., 27, 515-524.

Henry (2009) *Modification of red blood cells for laboratory quality control use* Curr. Opin. Hematol., 16, 467-472.

Henry and Komarraju (2012) Peptide-lipid constructs and their use in a Fc-function assay International application no. PCT/2012/000029 (publ. no. WO 2012/118388).

Hult et al (2012) *Flow cytometry evaluation of red blood cells mimicking naturally occurring ABO subgroups following modification with variable amounts of FSL_A and B constructs* Transfusion, 52, 247-251.

Karelin et al (2010) *Synthesis of* 3,6-*branched oligomannoside fragments of the mannan from Candida albicans cell wall corresponding to the antigenic factor* 4 Carbohydrate Research 345, 1283-1290.

Korchagina and Henry (2015) *Synthetic glycolipid-like constructs as tools for glycobiology research, diagnostics, and as potential therapeutics* Biochemistry (Moscow), Vol. 80, No 7, 857-871.

Korchagina et al (2009) *Block synthesis of blood group tetrasaccharides B (types* 1, 3 *and* 4) Mendeleev Commun., 19, 152-154.

Korchagina et al (2012) *Toward creating cell membrane glycolandscapes with glycan lipid constructs* Carbohydr. Res., 356, 238-246.

Lee and Lee (1997) *Facile Synthesis of a High-Affinity Ligand for Mammalian Hepatic Lectin Containing Three Terminal N-Acetylgalactosamine Residues* Bioconjugate Chem., 8, 762-765.

Litherland and Mann (1938) *The amino-derivatives of pentaerythritol Part I. Preparation* Journal of the Chemical Society, 1588-95.

McNaught (1996) *Nomenclature of carbohydrates* Pure & App. Chem., 68, No. 10, 1919-2008.

Nifant'ev et al (1996) *Selectin-receptors* 4*: synthesis of tetrasaccharides sialyl Lewis A and sialyl Lewis X containing a spacer group*[1, 2] J. Carbohydrate Chemistry, 15(8), 939-953.

Oliver et al (2011) *In vivo neutralization of anti-A and successful transfusion of A antigen incompatible red cells in an animal model* Transfusion, 51, 2664-2675.

Oliver et al (2011) *Modeling transfusion reactions and predicting in vivo cell survival with kodecytes* Transfusion, 51, 1723-1730.

Paulsen et al (1978) *Darstellung selektiv blockierter* 2-*azido-*2-*desoxy-$_D$-gluco-und-$_D$-galactophyranosylhalogenide: Reaktivitat und* $^{13}$*C-NMR-Spektren* Carbohydrate Research, 64, 339-364.

Pazynina et al (2003) *Synthesis of complex* 2-3 *sialooligosaccharides, including sulfated and fucosylated ones, using Neu*5*Ac*α2-3*Gal as a building block* Mendeleev Commun, 13(6), 245-248.

Pazynina et al (2008) *The synthesis of linear trilactosamine* Russian Journal of Bioorganic Chemistry, Vol. 34, No. 5, 625-631.

Perry and Henry (2013) *Teaching the recognition of hemolysis by controlling antibody mediated in vitro hemolysis with kodecytes* Transfusion, 53 (Suppl.), 182A.

Perry and Henry (2015) *Training students in serologic reaction grading increased perceptions of self-efficacy and ability to recognize serologic reactions but decreased grading accuracy* Transfusion, January 7, DOI: 10.1111/trf.12985 [Epub ahead of print].

Rhyzhov et al (2012) *Block synthesis of A tetrasaccharides (types* 1, 3 *and* 4) *related to the human ABO blood group system* Carbohydrate Research 351, 17-25.

Sherman et al (2001) *Synthesis of Neu*5*Ac-and Neu*5*Gc-*α-(2→6')*-lactosamine* 3*-aminopropyl glycosides* Carbohydrate research 330, 445-458.

Svensson et al (2013) *Forssman expression on human erythrocytes: biochemical and genetic evidence of a new histo-blood group system* Blood, 121, 1459-1468.

Vodovozova et al (2000) *Antitumour activity of cytotoxic liposomes equipped with s electin ligand SiaLe$_x$*, in a mouse mammary adenocarcinoma model European Journal of Cancer, 36, 942-949.

Yashunsky et al (2016) *Synthesis of* 3*-aminopropyl glycosides of linear* β-(1→3)*-D-glucooligosaccharides* Carbohydrate Research 419, 1-10.

The invention claimed is:

1. A construct of the structure:

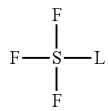

where F is an oligopeptide comprising an N-maleoyl-β-alanine conjugated Cys residue, L is a conjugated phosphatidylethanolamide and S is a tetraantennary spacer of the structure:

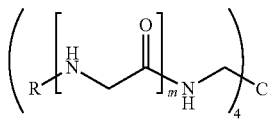

where m is the integer 1, 2 or 3 and R is of the structure:

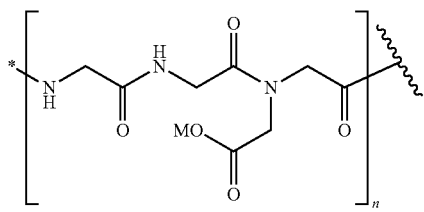

where M is a monovalent cation or substituent, n is the integer 2, 3, 4, 5, 6 or 7, and * is the point of attachment of F or L.

2. The construct of claim 1 where M is H.

3. The construct of claim 2 where L is a conjugated phosphatidylethanolamide of the structure:

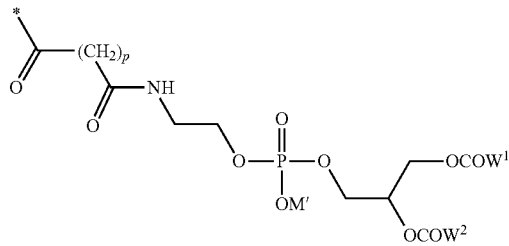

where p is the integer 3, 4 or 5, $W^1$ and $W^2$ are independently selected from $C_{16-20}$-alkyl or mono- or di-unsaturated $C_{16-20}$-alkenyl groups and * is the point of attachment of S.

4. The construct of claim 3 where the construct comprises the partial structure:

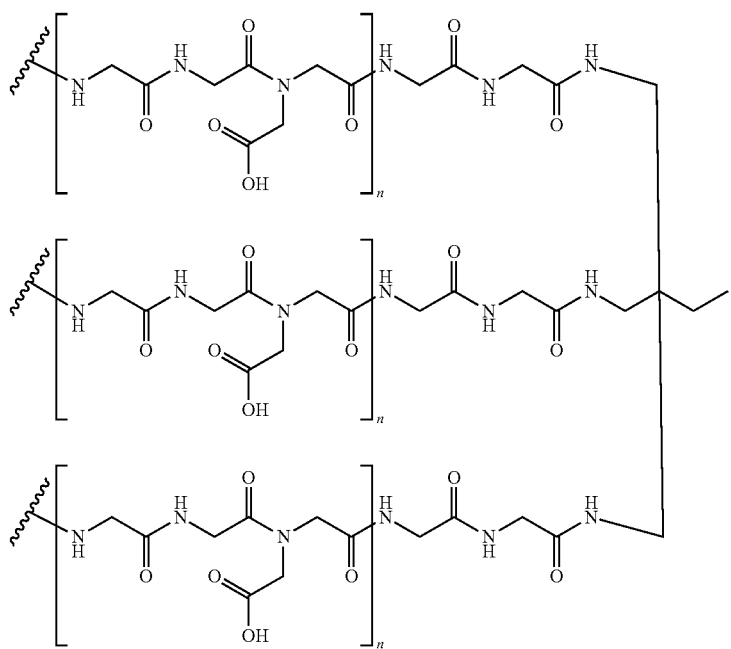
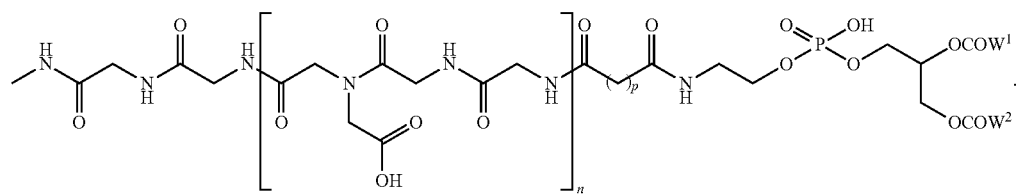
5. The construct of claim 4 where the construct is of the structure:
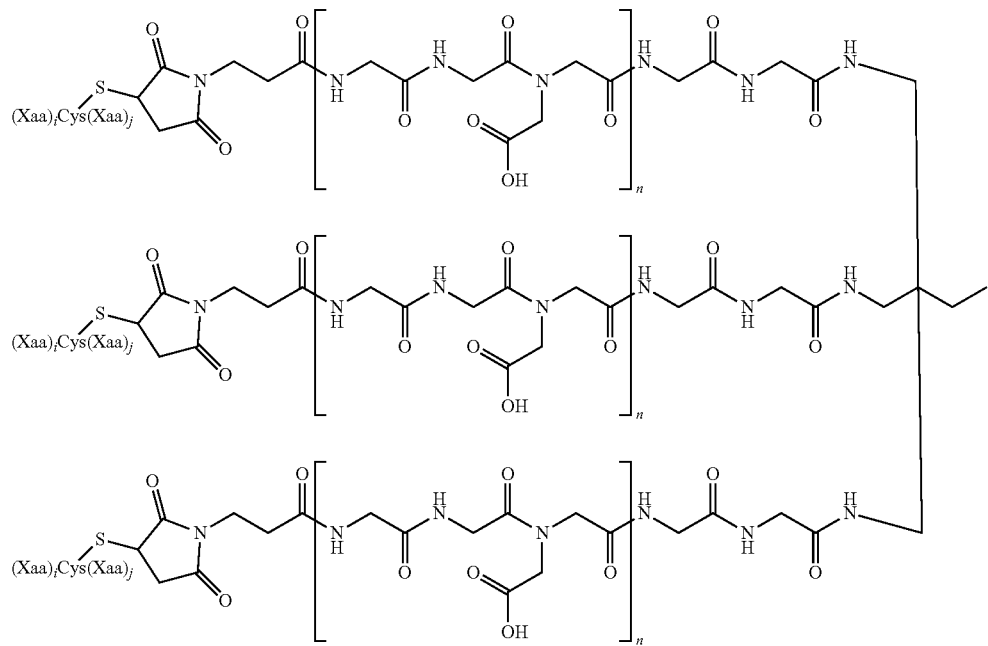

-continued
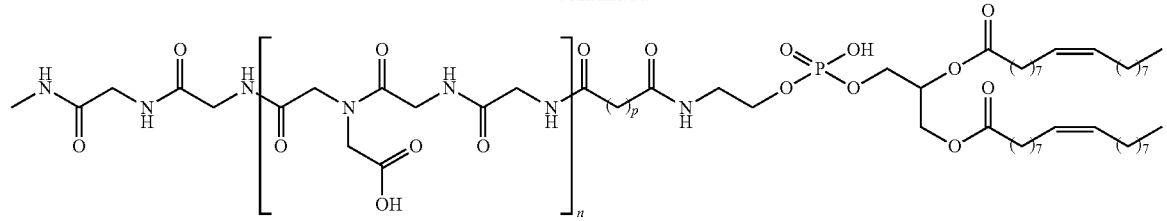
where Xaa is an amino acid residue and i and j are independently either zero or integers the sum of which is in the range 5 to 30 inclusive.
6. The construct of claim 5 where i is an integer in the range 5 to 30 inclusive and j is zero.
7. The construct of claim 6 where i is the integer 13 and j is zero.
8. The construct of claim 7 where the oligopeptide is the peptide of SEQ ID NO: 01.
* * * * *